United States Patent
Kellogg et al.

(10) Patent No.: US 7,476,361 B2
(45) Date of Patent: Jan. 13, 2009

(54) MICROFLUIDICS DEVICES AND METHODS OF DILUTING SAMPLES AND REAGENTS

(75) Inventors: Gregory Kellogg, Cambridge, MA (US); Timothy Johnson, Andover, MA (US); Eric Schilling, Cambridge, MA (US)

(73) Assignee: Tecan Trading AG, Mannedorf (CH)

( * ) Notice: Subject to any disclaimer, the term of this patent is extended or adjusted under 35 U.S.C. 154(b) by 862 days.

(21) Appl. No.: 10/746,821

(22) Filed: Dec. 24, 2003

(65) Prior Publication Data
US 2004/0203136 A1    Oct. 14, 2004

Related U.S. Application Data

(60) Provisional application No. 60/436,335, filed on Dec. 24, 2002, provisional application No. 60/436,384, filed on Dec. 24, 2002.

(51) Int. Cl.
*G01N 1/18* (2006.01)
*G01N 1/38* (2006.01)
*G01N 9/30* (2006.01)

(52) U.S. Cl. .............. 422/72; 422/63; 422/64; 422/99; 422/100; 436/45; 436/179; 436/180

(58) Field of Classification Search .......... 422/63, 422/64, 72, 99, 100, 103; 436/45, 179, 180; 435/287.2
See application file for complete search history.

(56) References Cited

U.S. PATENT DOCUMENTS

| 6,063,589 | A | 5/2000 | Kellogg et al. |
| 6,319,468 | B1* | 11/2001 | Sheppard et al. ............. 422/63 |
| 6,319,469 | B1* | 11/2001 | Mian et al. .................... 422/64 |
| 6,582,662 | B1* | 6/2003 | Kellogg et al. ................ 422/72 |
| 2002/0106786 | A1 | 8/2002 | Carvalho et al. |
| 2002/0137218 | A1 | 9/2002 | Mian et al. |
| 2002/0151078 | A1 | 10/2002 | Kellogg et al. |

FOREIGN PATENT DOCUMENTS

WO    WO 02/075312 A1    9/2002

* cited by examiner

*Primary Examiner*—Maureen M Wallenhorst
(74) *Attorney, Agent, or Firm*—Frommer Lawrence & Haug LLP; Thomas J. Kowalski; Deborah L. Lu

(57) ABSTRACT

This invention relates to methods and apparatus for performing microanalytic and microsynthetic analyses and procedures. The invention provides a microsystem platform and a micromanipulation device for manipulating the platform that utilizes the centripetal force resulting from rotation of the platform to motivate fluid movement through microchannels. These assays may be performed for a variety of purposes, including but not limited to screening of drug candidate compounds, life sciences research, and clinical and molecular diagnostics. Methods specific for the apparatus of the invention for performing any of a wide variety of microanalytical or microsynthetic processes are provided.

16 Claims, 72 Drawing Sheets

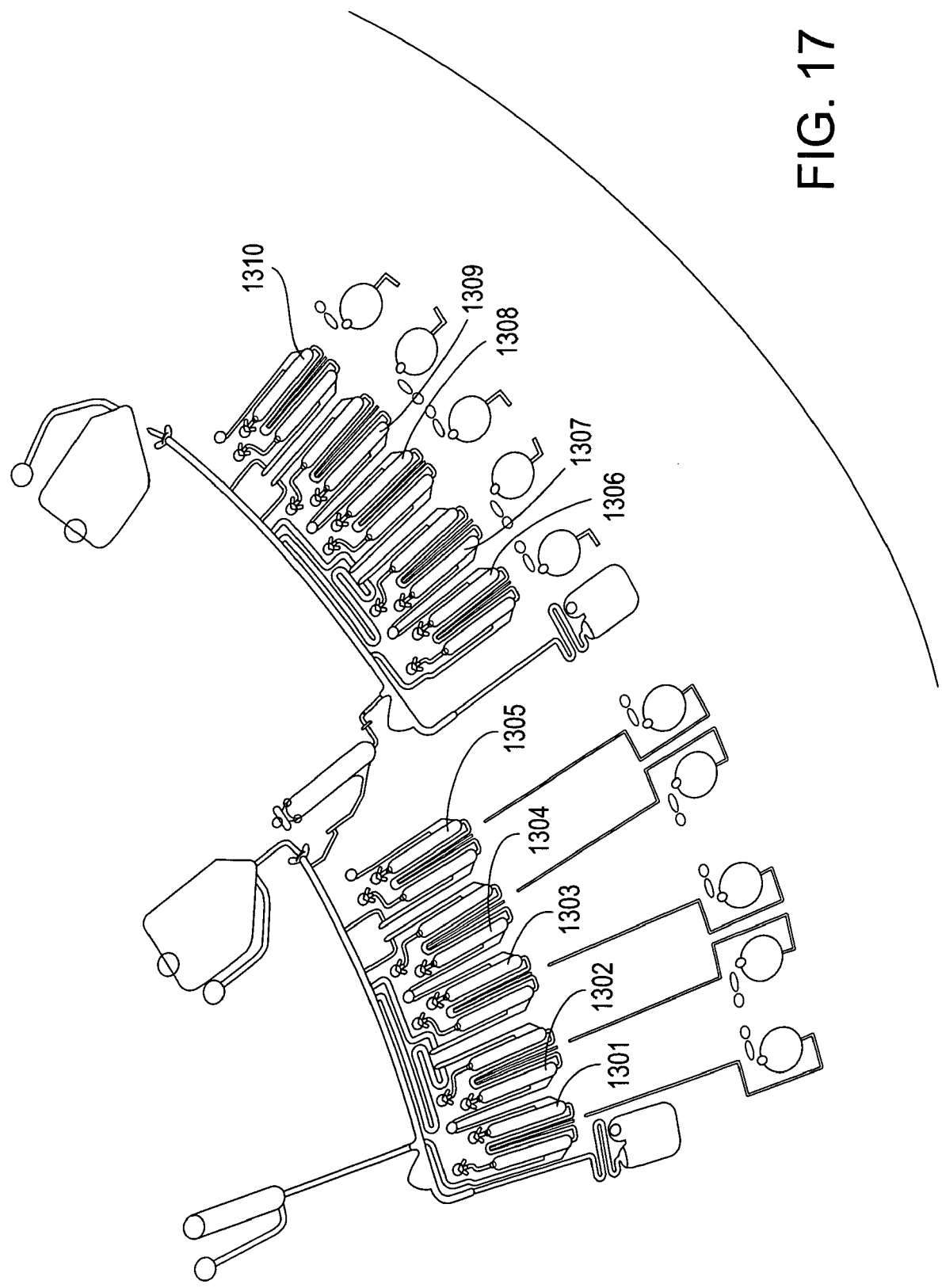

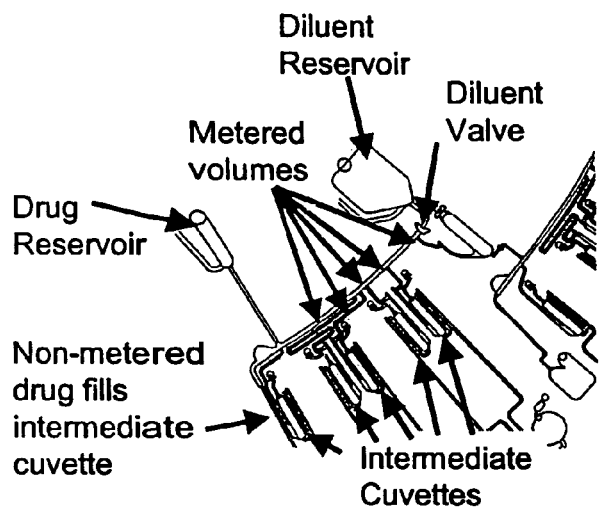
(a)
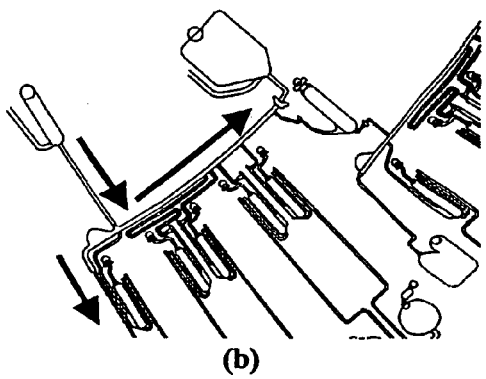
(b)
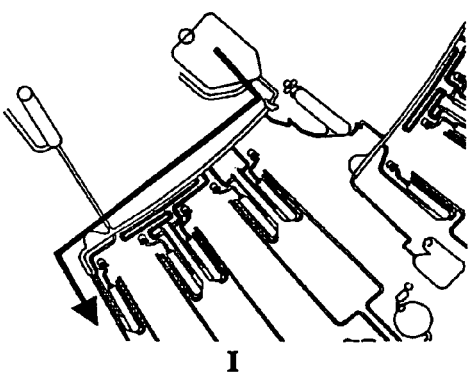
I
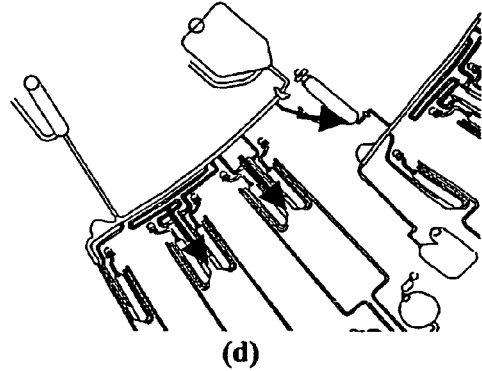
(d)
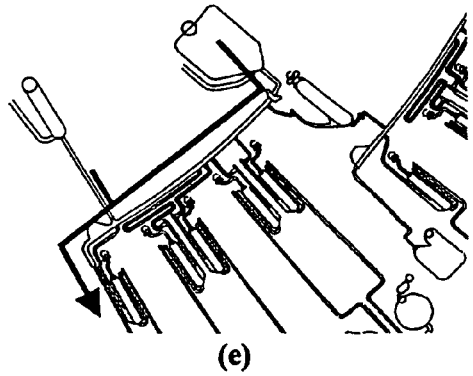
(e)
Fig 78

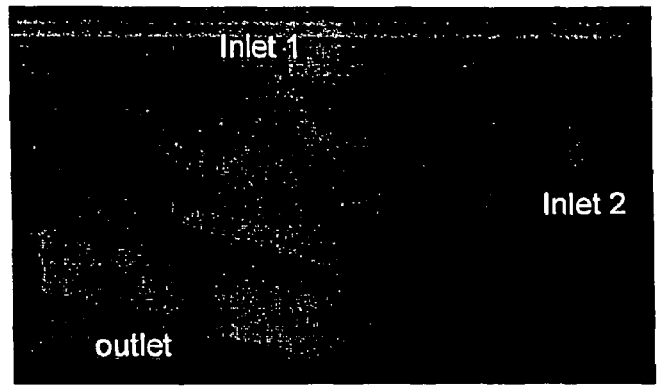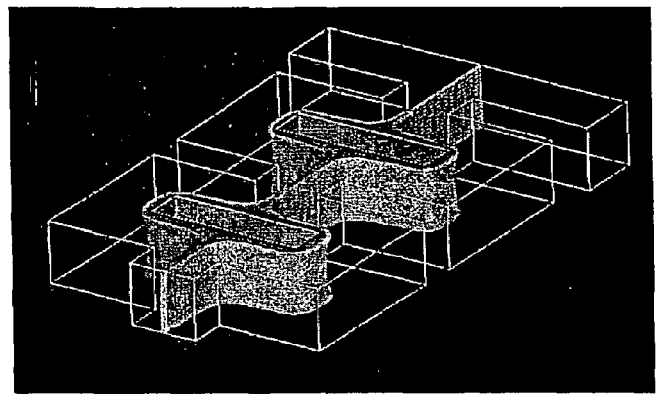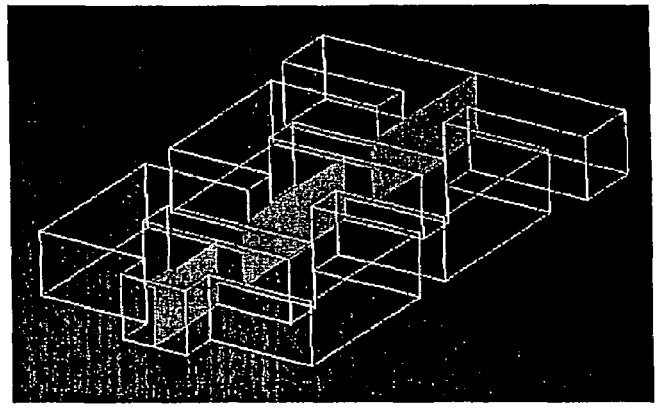
Fig. 22

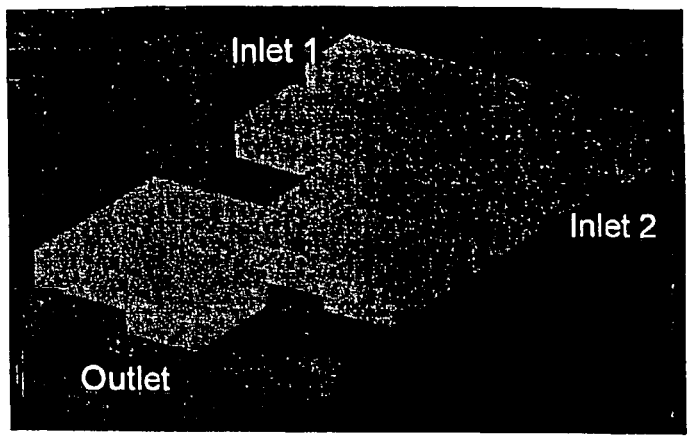
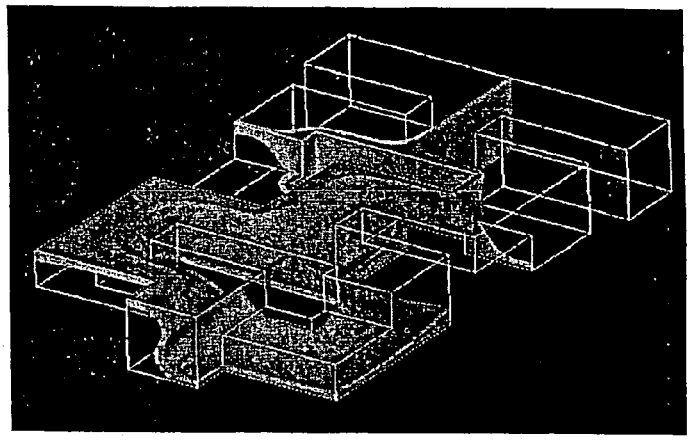
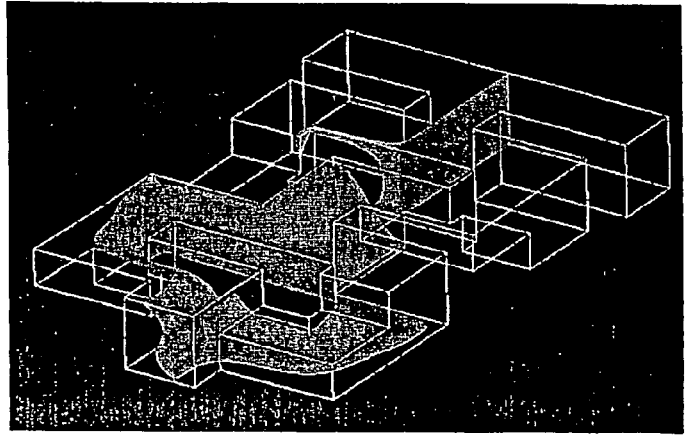
Fig. 23

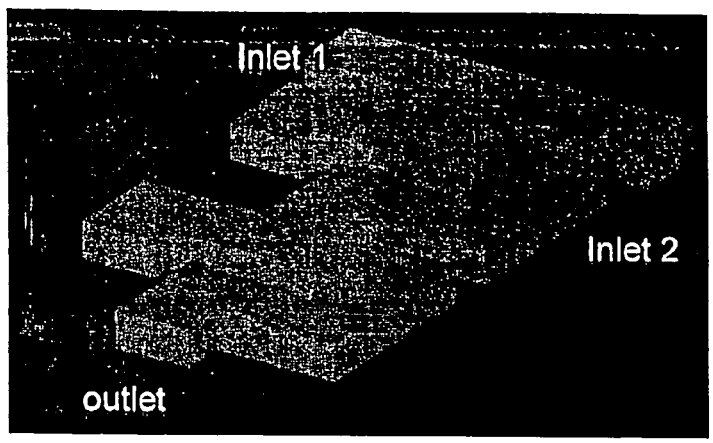
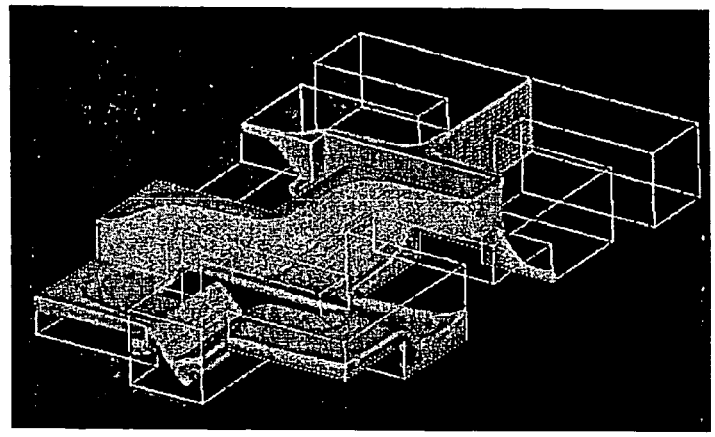
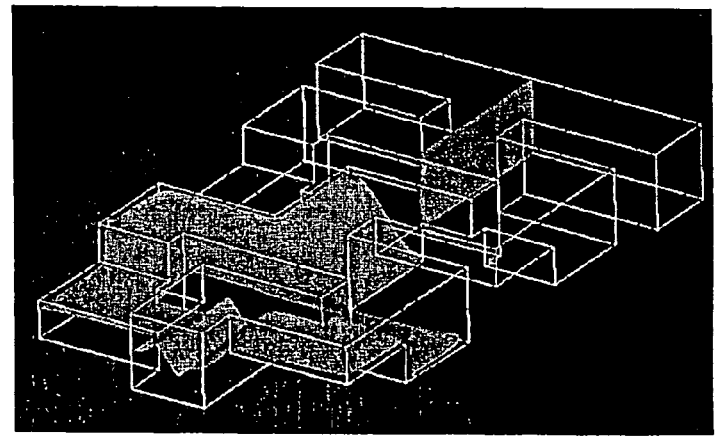
Fig. 24

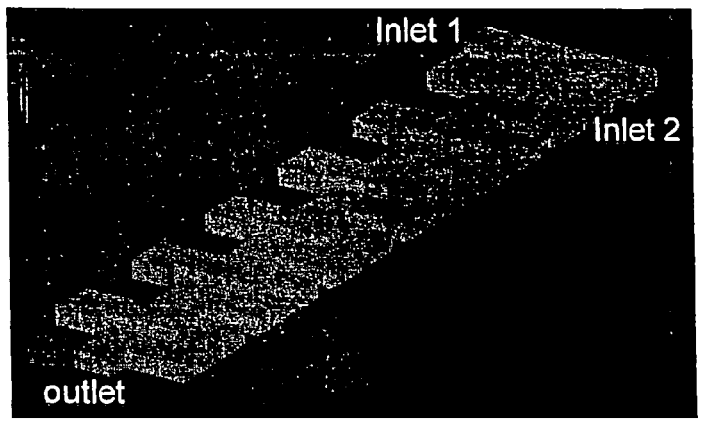
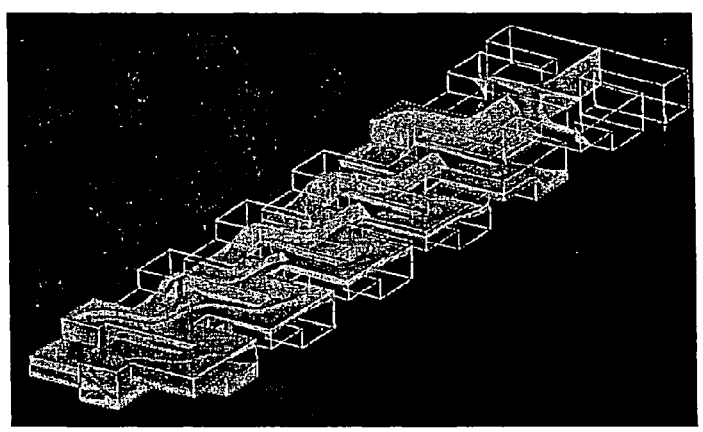
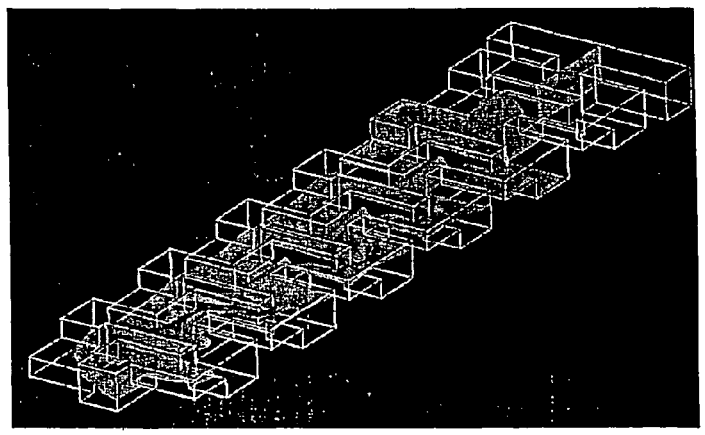
Fig. 25

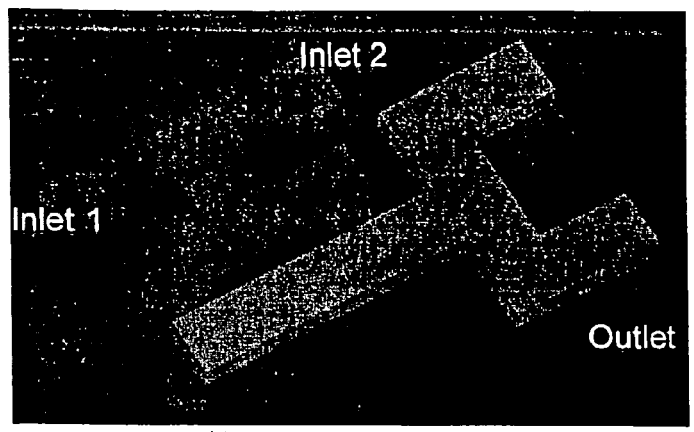
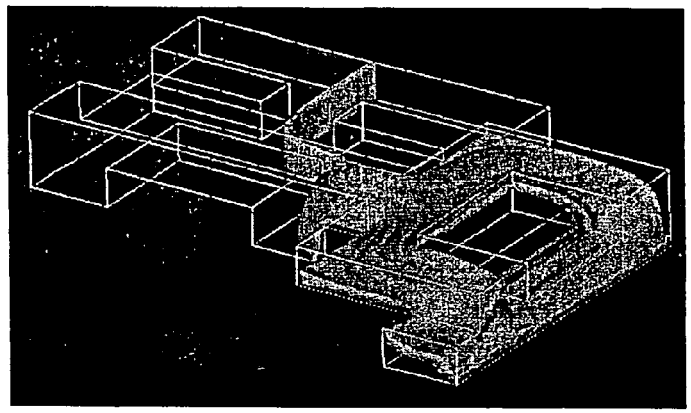
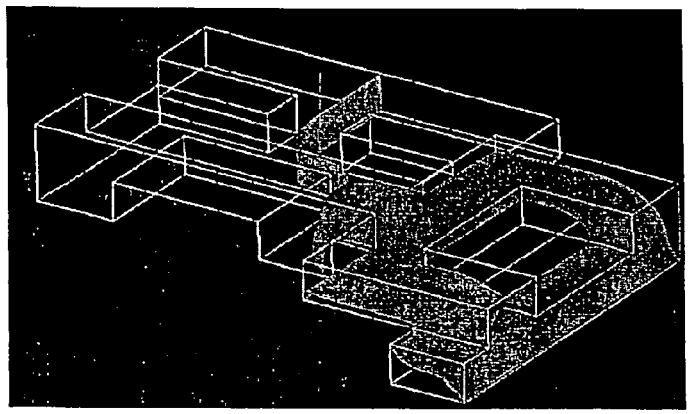
Fig. 26

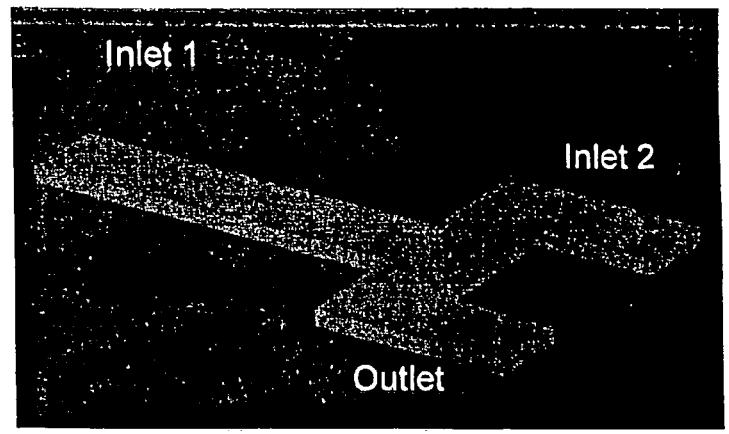
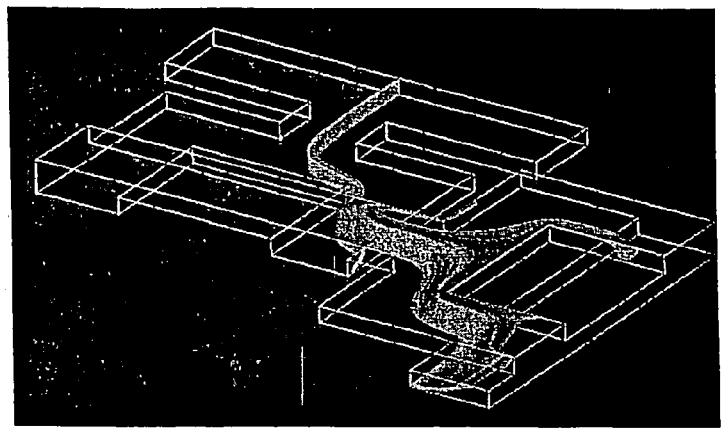
Fig. 27
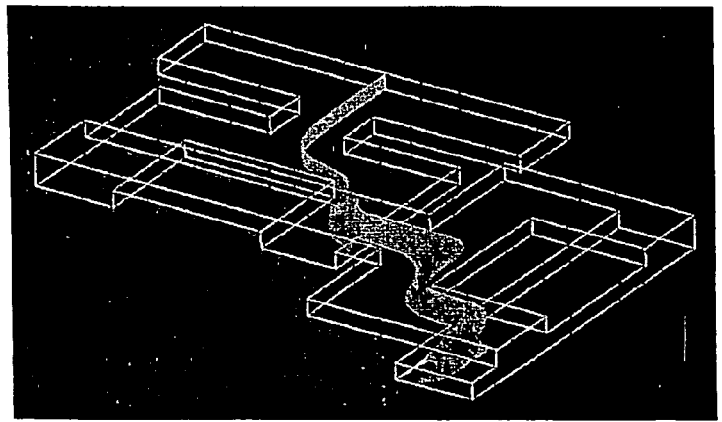

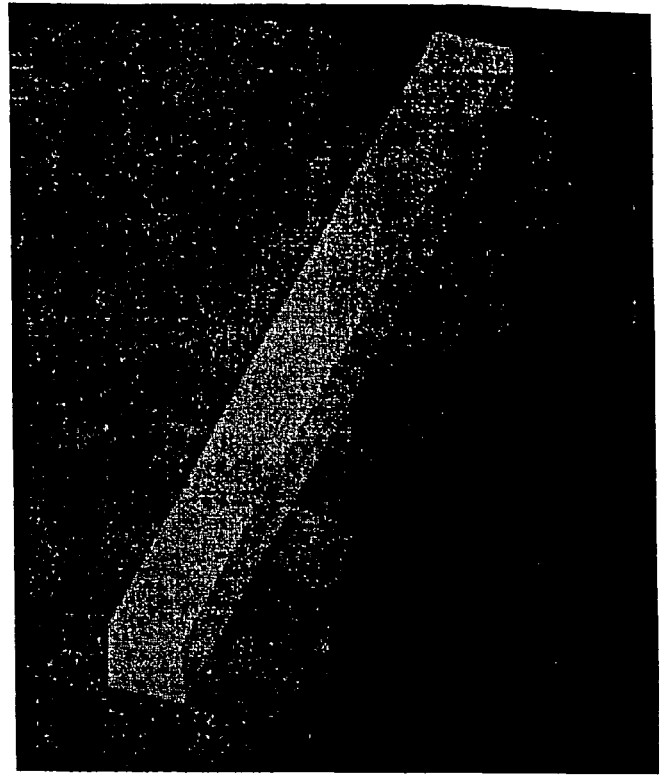
Fig. 32
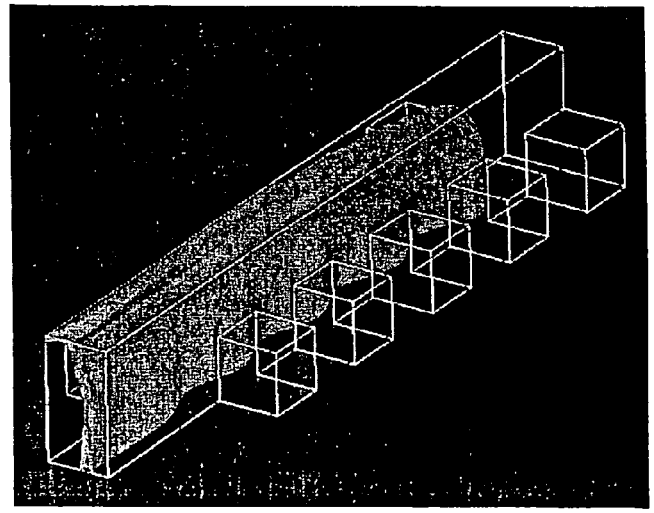

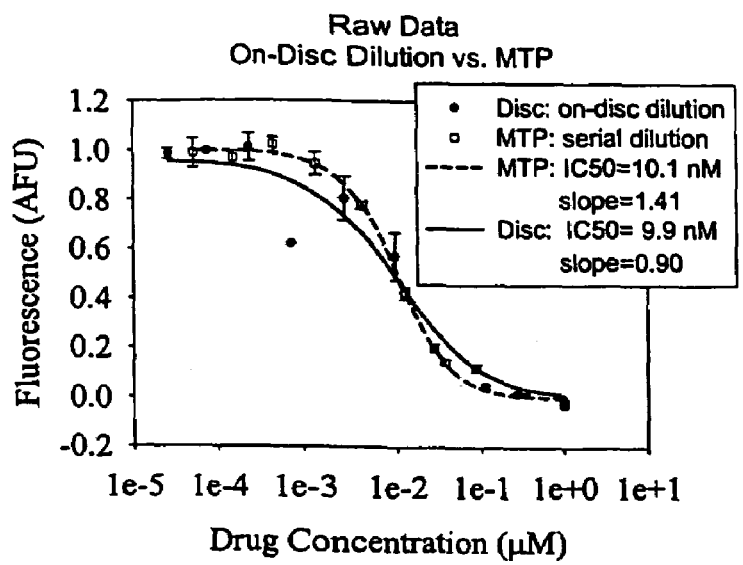
Figure 35A. Assay results from the combination of three dilution structures along with MTP results.
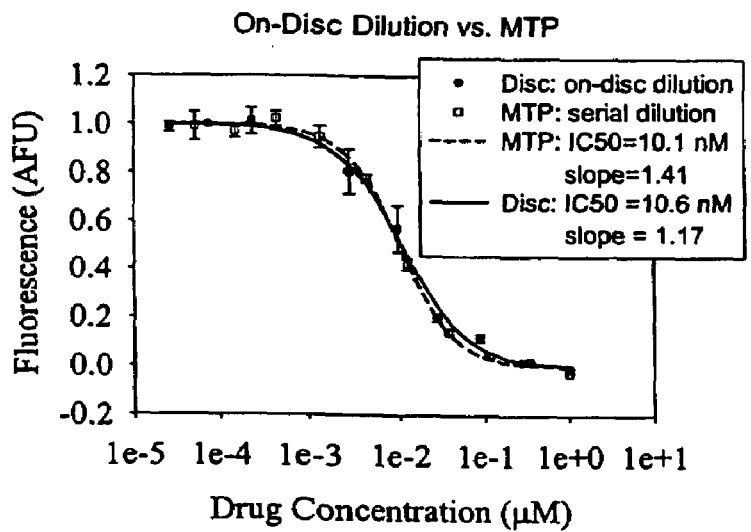
Figure 35B. The assay results from Figure 35A with the 6th dilution point removed.

MICROFLUIDICS DEVICES AND METHODS OF DILUTING SAMPLES AND REAGENTS

This application claims priority to U.S. Provisional Applications Serial Nos. 60/436,335 and 60/436,384, each filed Dec. 24, 2002, the disclosure of each of which is explicitly incorporated by reference herein.

BACKGROUND OF THE INVENTION

1. Field of the Invention

This invention relates to methods and apparatus for performing microanalytic and microsynthetic analyses and procedures. In particular, the invention relates to microminiaturization of genetic, biochemical and bioanalytic processes. Specifically, the present invention provides devices and methods for the performance of miniaturized biochemical assays. These assays may be performed for a variety of purposes, including but not limited to screening of drug candidate compounds, life sciences research, and clinical and molecular diagnostics. Methods for performing any of a wide variety of such microanalytical or microsynthetic processes using the microsystems apparatus of the invention are also provided.

2. Background of the Related Art

Recent developments in a variety of investigational and research fields have created a need for improved methods and apparatus for performing analytical, particularly bioanalytical assays at microscale (i.e., in volumes of less than 100 µL). In the field of pharmaceuticals, for example, an increasing number of potential drug candidates require assessment of their biological function. As an example, the field of combinatorial chemistry combines various structural sub-units with differing chemical affinities or configurations into molecules; in theory, a new molecule having potentially unique biochemical properties can be created for each permutation of the sub-units. In this way, large libraries of compounds may be synthesized from relatively small numbers of constituents, each such compound being a potential drug lead compound of usually unknown biological activity and potency.

More traditional approaches to compound library development are also yielding growing numbers of candidates, including the use of naturally-derived compounds extracted from plants, fungi, and bacteria. In part, this is due to an increased understanding of the function of these compounds, including how they affect the metabolic pathways of the organisms which synthesize and use them; the increasing refinement in identifying and understanding compounds based on small structural and compositional differences; and improved methods for extracting and purifying these compounds.

Increased numbers of potential targets for these drug candidates are also being identified. Recent advances in biology, most notably the Human Genome Project, have discovered many molecules whose biochemical activity is implicated in various disease states. Although these novel targets can provide exquisitely precise and specific indicia of how biological processes underlying disease can be effectively controlled and manipulated, drugs must be identified, usually by screening processes, to find compounds that can enhance, diminish, or otherwise alter these targets' ability to affect the metabolic pathways associated with disease.

The function of drug candidates, targets, and the effect of the candidates on targets is assessed in the early stages of pharmaceutical development through a process of screening that typically includes: binding of a drug candidate to a portion or domain of the target molecule; immunoassays that bind to drug candidate target domains correlated with drug efficacy; enzymatic assays, in which the inhibition of an enzymatic activity of the target by the drug candidate can be used as a sign of efficacy; protein/protein binding; and protein/DNA(RNA) binding. Additional assays involve the use of living cells and include gene expression, in which levels of transcription in response to a drug candidate are monitored, and functional assays designed to investigate both macroscopic effects, such as cell viability, as well as biochemical effects and products produced in and by the cells as a result of treatment with the drug lead compound. (Wallace & Goldman, 1997, "Bioassay Design and Implementation", in *High-Throughput Screening: The Discovery of Bioactive Substances*, J. P. Devlin, ed., Marcel Dekker, Inc.: New York, pp. 279-305).

In initial screening of compounds against targets, the number of possible screens is roughly the number of candidates multiplied by the number of targets. As a result of the growth in both the number of candidates and the number of targets, the number of assays that must be performed is growing rapidly. In addition to the increasing number of assays to be performed, it is desirable to reduce the time required to perform the assays in order to obtain results of such screenings in a timely and useful fashion. Finally, "multiplexing" technology that allows the performance of multiple assays on one sample within a single reaction well—for example, by using readily-distinguishable signals, such as fluorescent moieties with different characteristic wavelengths—can be used to increase throughput.

In addition to drug screening assays, biological research has uncovered a vast reservoir of genetic information and diversity having little if any correlation with the function of the gene products encoded by the deciphered DNA. On the one hand, the identification of the nucleotide sequence of the human genome, coupled with bioinformatics analysis of these sequences, has identified a larger number of protein coding sequences (termed "open reading frames") that can and probably do encode functional proteins. However, since these sequences have been uncovered by simply "reading" a sequence without any information (such as the correlation of a genetic locus with a mutation associated with a disease), the function of the gene products of such a locus must be determined in order to fully understand and identify what protein target is encoded thereby and what utility drug candidates directed to such a target might have. On the other hand, human genome sequencing efforts have also identified genetic mutations (such as single nucleotide polymorphisms, or "SNPs") that may or may not be associated with human disease. In either instance, the products of this human genetic information must be assayed to determine the activity of the genes, both "wild-type" and mutant, encoded at each new genetic locus. Progress in life sciences research requires researchers to perform large numbers of assays as they investigate the structure and function of proteins coded by the growing number of identified genes in the human genome. Many of the same assays and assay formats used in drug screening may be used in other life sciences research.

Large numbers of assays must also be performed in the field of molecular diagnostics, in which individuals can now be assayed for genetic mutation associated with a disease state or the propensity to develop a disease state. For example, any particular disease or propensity for disease may be associated with several different mutations in more than one gene that can determine disease susceptibility or severity. In the monitoring of a disease state, a disease may have a "fingerprint" consisting of certain genes the expression level of which can be used diagnostically to predict the severity of the disease. Monitoring expression levels of these genes can provide an indication of the response (or lack of response) to different treatment modalities.

For these and other applications in drug discovery, life sciences research, and molecular and clinical diagnostics there exists a need for systems and assay methods that can perform very many assays in a highly-parallel fashion at low cost. A central strategy has been the miniaturization of existing assays or development of new assays that work with very small volumes of drug compound and reagents. Miniaturization has been accompanied by the development of more sensitive detection schemes, including both better detectors for conventional signals (e.g., calorimetric absorption, fluorescence, and chemiluminescence) as well as new chemistries or assay formats (e.g., imaging, optical scanning, and confocal microscopy).

Miniaturization can also confer performance advantages. At short length scales, diffisionally-limited mixing is rapid and can be exploited to create sensitive assays (Brody et al., 1996, *Biophysical J.* 71: 3430-3431). Because fluid flow in miniaturized pressure-driven systems is laminar, rather than turbulent, processes such as washing and fluid replacement are well-controlled. Microfabricated systems also enable assays that rely on a large surface area to volume ratio such as those that require binding to a surface and a variety of chromatographic approaches.

The development of fluid-handling and processing for miniaturized assays has primarily involved the scaling down of conventional methods. The vast majority of initial drug screens have been performed conventionally in 96-well microtiter plates with operating volumes of less than 0.1-0.5 mL. The wells of these plates serve as "test tubes" for reactions as well as optical cuvettes for detection. Fluids are typically delivered to these plates using automated pipetting stations or external tubing and pumps; automation is also required for handling of plates and delivery to sub-systems such as plate washers (used in solid phase assays, for example).

Miniaturization has led to the creation of 384-well and 1536-well microtiter plates for total reaction volumes of between 0.015 and 0.1 mL. However, a number of problems arise-when miniaturizing standard plate technology. First, because the total volumes are smaller and the plates are open to the environment, evaporation of fluid during the course of an assay can compromise results. Another drawback of open plates is the existence of a fluid meniscus in the well. Meniscuses of varying configurations (due, for example to imperfections in the plate or differences in contact angle and surface tension) can distort the optical signals used to interrogate the samples. As the strength of the optical signals decreases with decreasing assay volume, correction for background distortions becomes more difficult. Finally, optical scanning systems for high-density plates are often complex and expensive. Methods that minimize evaporation, provide a more uniform optical pathway, and provide simpler detection schemes are desirable.

Highly accurate pipetting technologies have been developed to deliver fluids in precisely metered quantities to these plates. Most of these fluid-delivery methods for low volumes (below a few microliters) rely on expensive piezoelectric pipetting heads that are complex and difficult to combine or "gang" into large numbers of independent pipettors so that many wells may be addressed independently. As a result, fluid delivery is either completely or partially serial (i.e., a single micropipettor, or a small number of parallel delivery systems used repeatedly to address the entire plate). Serial pipetting defeats the aim of parallelism by increasing the amount of time required to address the plate. Methods that reduce the number and precision of fluid transfer steps are therefore needed.

Integration of microdevices with existent laboratory infrastructure is also desirable and has been poorly addressed in the art. This integration is one of both scale and format. Regarding scale, fluids must be transferred to devices from the external world, where the volumes in which they are handled are typically one or more orders of magnitude greater than the volumes required by the microdevice. It is desirable that this transition be done in a way that does not introduce excessively complex processes or machinery and which does not create excessive errors, such as in the volume of fluid transferred. Regarding format, it is desirable that microdevices have a similar physical aspect to macroscale devices already used in laboratories, especially in regard to the manner in which fluids are added to or removed from the devices. Microdevices that can be loaded with fluids using standard methods, such as pipettors, will be more easily and widely used in a variety of settings.

Fluid processing in microtiter plates is also difficult. The small dimensions of the wells, while enhancing diffusional mixing, suppress turbulence and make difficult mixing on length scales between a few tens of microns and a few millimeters. For similar reasons, washing, an important step in many assays can be problematic. Methods that reduce both the number of manipulations of fluids on the plate as well as manipulations of the plate itself (such as passing the plate to and from washing stations) can reduce cost while improving assay quality through suppression of contamination, carryover, and fluid loss.

Thus, there is a need in the art for improved micromanipulation apparatus and methods for performing bioanalytic assays more rapidly and economically using less biological sample material and which may be easily interfaced with existing laboratory instrumentation. Relevant to this need in the art, some of the present inventors have developed a microsystem platform and a micromanipulation device to manipulate said platform by rotation, thereby utilizing the centripetal forces resulting from rotation of the platform to motivate fluid movement through microchannels embedded in the microplatform, as disclosed in co-owned U.S. Pat. No. 6,063,589, issued May 16, 2000, and co-owned and co-pending patent applications U.S. Ser. Nos. 08/761,063, filed Dec. 5, 1996; Ser. No. 08/768,990, filed Dec. 18, 1996; Ser. No. 08/910, 726, filed Aug. 12, 1997; Ser. No. 08/995,056, filed Dec. 19, 1997; Ser. No. 09/315,114, filed May 19, 1999, and Ser. No. 09/858,318, filed May 15, 2001, the disclosures of each of which are explicitly incorporated by reference herein.

SUMMARY OF THE INVENTION

This invention provides microsystems platforms as disclosed in co-owned U.S. Pat. No. 6,063,589, issued May 16, 2000, and co-owned and co-pending patent applications U.S. Ser. Nos. 08/761,063, filed Dec. 5, 1996; Ser. No. 08/768,990, filed Dec. 18, 1996; Ser. No. 08/910,726, filed Aug. 12, 1997; Ser. No. 08/995,056, filed Dec. 19, 1997; Ser. No. 09/315, 114, filed May 19, 1999, and Ser. No. 09/858,318, filed May 15, 2001, the disclosures of each of which are explicitly incorporated by reference herein.

The invention provides apparatus and methods for performing microscale processes on a microplatform, whereby fluid is moved on the platform in defined channels motivated by centripetal force arising from rotation of the platform. The first element of the apparatus of the invention is a microplatform that is a rotatable structure, most preferably a disk, the disk comprising fluid (sample) inlet ports, fluidic microchannels, reagent reservoirs, collection chambers, detection chambers and sample outlet ports, generically termed "microfluidic structures." In particular, the invention provides such microfluidic structures adapted to and arranged to accomplish efficient dilution of a sample with a diluent. Especially provided are such structures that enable serial dilution, for example, over several ten-fold increments (logs) of dilution, providing for efficient dilution of solutes from a sample, most preferably a biological sample. The microsystems platforms of the invention so provided permit microminiaturization of assays, most preferably biological assays, such as, for example, immunoassays, enzymatic assays including enzyme inhibition assays, and specific binding assays of members of a specific binding pair.

In the practice of the methods of the invention, the disk is rotated at speeds from about 1 to about 30,000 rpm for generating centripetal acceleration that enables fluid movement through the microfluidic structures of the platform. The disks of the invention also preferably comprise air outlet ports and air displacement channels. The air outlet ports and in particular the air displacement ports provide a means for fluids to displace air, thus ensuring uninhibited movement of fluids on the disk. Specific sites on the disk also preferably comprise elements that allow fluids to be analyzed, as well as detectors for each of these effectors.

The discs of this invention have several advantages over those that exist in the centrifugal analyzer art. Foremost is the fact that flow is laminar due to the small dimensions of the fluid channels; this allows for better control of processes such as mixing and washing. Secondly, the small dimensions conferred by microfabrication enable the use of "passive" valving, dependent upon capillary forces, over much wider ranges of rotational velocities and with greater reliability than in more macroscopic systems. To this are added the already described advantages of miniaturization.

The second element of the invention is a micromanipulation device that is a disk player/reader device that controls the function of the disk. This device comprises mechanisms and motors that enable the disk to be loaded and rotated. In addition, the device provides means for a user to operate the microsystems in the disk and access and analyze data, preferably using a keypad and computer display. The micromanipulation device also advantageous provides means for actuation of on-disc elements, such as active valves; the application and control of heat to the disc for purposes of chemical or biological incubation; and means for adding fluids to and removing fluids from the discs. The micromanipulation devices of this invention are more particularly described in co-owned U.S. Pat. No. 6,063,589, issued May 16, 2000, and co-owned and co-pending patent applications U.S. Ser. Nos. 08/761,063, filed Dec. 5, 1996; Ser. No. 08/768,990, filed Dec. 18, 1996; Ser. No. 08/910,726, filed Aug. 12, 1997; Ser. No. 08/995,056, filed Dec. 19, 1997; Ser. No. 09/315,114, filed May 19, 1999, and Ser. No. 09/858,318, filed May 15, 2001, the disclosures of each of which are explicitly incorporated by reference herein.

The invention specifically provides microsystems platforms comprising microfluidics components contained in one or a multiplicity of platform layers that are fluidly connected to permit transfer, mixing and assay performance on the sealed surface of the platform. The platforms preferably comprise reagent reservoirs containing a sufficient volume, preferably from about 1 nL to about 1 mL, of a reagent solution for a multiplicity of individual assays. The reagent reservoirs are fluidly connected by microchannels to one or more preferably a multiplicity of collection, and more preferably detection, chambers, and the microfluidics components arranged so that a specific volume of the reagent solution is delivered to each collection chamber. More preferably, said reagent reservoirs are fluidly connected to mixing structures, most preferably a mixing microchannel that is also fluidly connected to a sample reservoir, so that one or a plurality of reagents are mixed with sample and the resulting mixture delivered into the detection chamber. In preferred embodiments, the platform comprises a multiplicity of sample reservoirs and mixing structures fluidly connected with a multiplicity of detection chambers. In additional preferred embodiments, the platform comprises microfluidic structures, including sample reservoirs, diluent reservoirs, dilution reservoirs, and overflow chambers, for the effective and efficient dilution of solutes or particulates from a sample solution or suspension, most preferably a biological solution or suspension.

In the use of the platforms of the invention, fluids (including samples and reagents) are added to the platform when the platform is at rest. Thereafter, rotation of the platform on a simple motor motivates fluid movement through microchannels for various processing steps. In preferred embodiments, the platforms of the invention permit the use of a detector, most preferably an optical detector, for detecting the products of the assay, whereby the collection chambers comprise optical cuvettes, preferably at the outer edge of the platform, most preferably wherein the platform is scanned past a fixed detector through the action of the rotary motor. Because the platforms of the invention are most preferably constructed using microfabrication techniques as described more fully below, the volumes of fluids used may be made arbitrarily small as long as the detectors used have sufficient sensitivity.

The present invention solves problems in the current art through the use of a microfluidic disc in which centripetal acceleration is used to move fluids. It is an advantage of the microfluidics platforms of the present invention that the fluid-containing components are constructed to contain a small volume, thus reducing reagent costs, reaction times and the amount of biological material required to perform an assay. It is also an advantage that the fluid-containing components are sealed, thus eliminating experimental error due to differential evaporation of different fluids and the resulting changes in reagent concentration. Because the microfluidic devices of the invention are completely enclosed, both evaporation and optical distortion are reduced to negligible levels. The platforms of the invention also advantageously permit "passive" mixing and valving, i.e., mixing and valving are performed as a consequence of the structural arrangements of the components on the platforms (such as shape, length, position on the platform surface relative to the axis of rotation, and surface properties of the interior surfaces of the components, such as wettability as discussed below), and the dynamics of platform rotation (speed, acceleration, direction and change-of-direction), and permit control of assay timing and reagent delivery.

The disclosed invention also provides microfluidic disc comprising metering structures and a microfluidic network that is used to distribute aliquots of reagent to each of a multiplicity of mixing structures, each mixing structure being fluidly connected to one of a multiplicity of sample reservoirs, thereby permitting parallel processing and mixing of the samples with one or more common reagents. The fluidic network, defined as the overall pattern of channels, reservoirs, microvalves, and air vents, may be planar or three-dimensional, depending upon the application under consideration. The use of such metering and distribution reduces the need for automated reagent distribution mechanisms, reduces the amount of time required for reagent dispensing (that can be performed in parallel with distribution of reagent to a multiplicity of reaction chambers), and permits delivery of small (nL-to-μL) volumes without using externally-applied electromotive means.

The microfluidic discs of the invention also comprise microfluidics structures particularly adapted and arranged to provide dilution, most preferably serial dilution, of a solute or particulate from a sample, most preferably a biological sample. Such structures are arrayed in the platform, preferably in conjunction and in fluidic contact with the metering and other microfluidics structures comprising the disc. As provided in further detail herein, said dilution-specific microfluidics structures and arrangements thereof preferably comprise sample reservoirs, overflow reservoirs, one or a plurality of diluent reservoirs, one or a plurality of dilution reservoirs, a metering manifold, wherein the metering manifold is fluidly connected to each of the plurality of dilution reservoirs and the manifold is further fluidly connected to the overflow reservoir, and a plurality of microchannels embedded in the microsystems platform and in fluidic contact with the reagent reservoir, manifold, diluent reservoir, and plurality of dilution reservoirs. As used in the practice of the invention, rotation of the platform motivates flow of a sample and a diluent through the metering manifold and into one or a plurality of dilution reservoirs, and wherein the sample is uniformly diluted from a first concentration in the sample reservoir to a lesser, more dilute sample concentration in the one or plurality of dilution reservoirs.

The assembly of a multiplicity of collection chambers on the platforms of the invention also permits simplified detectors to be used, whereby each individual collection/detection chamber can be scanned using mechanisms well-developed in the art for use with, for example, CD-ROM technology. Finally, the platforms of the invention are advantageously provided with sample and reagent entry ports for filling with samples and reagents, respectively, that can be adapted to liquid delivery means known in the art (such as micropipettors).

The platforms of the invention reduce the demands on automation in at least three ways. First, the need for precise metering of delivered fluids is relaxed through the use of on-disc metering structures, as described more fully in co-owned U.S. Pat. No. 6,063,589, issued May 16, 2000, and co-owned and co-pending patent applications U.S. Ser. Nos. 08/761,063, filed Dec. 5, 1996; Ser. No. 08/768,990, filed Dec. 18, 1996; Ser. No. 08/910,726, filed Aug. 12, 1997; Ser. No. 08/995,056, filed Dec. 19, 1997; Ser. No. 09/315,114, filed May 19, 1999, and Ser. No. 09/858,318, filed May 15, 2001, the disclosures of each of which are explicitly incorporated by reference herein. By loading imprecise volumes, slightly in excess of those needed for the assay, and allowing the rotation of the disc and use of appropriate microfluidic structures to meter the fluids, much simpler (and less expensive) fluid delivery technology may be employed than is the conventionally required for high-density microtitre plate assays.

Second, the total number of fluid "delivery" events on the microfluidic platform is reduced relative to microtiter plates. By using microfluidic structures that sub-divide and aliquot common reagents (such as reagent solutions, buffers, and enzyme substrates) used in all assays performed on the platform, the number of manual or automated pipetting steps are reduced by at least half (depending on the complexity of the assay). Examples of these structures have been disclosed in co-owned U.S. Pat. No. 6,063,589, issued May 16, 2000, and incorporated by reference herein; and are disclosed below.

Third, the requirement that samples, particularly biological samples be dilute, especially serially diluted in accordance with the practice of a variety of assays such as immunological detection and specificity assays, is automated using the dilution structures on the disc, that permit effective and automatic (i.e., without user intervention) dilution, particularly serial dilution, from a multiplicity of biological samples.

Certain preferred embodiments of the apparatus of the invention are described in greater detail in the following sections of this application and in the drawings.

BRIEF DESCRIPTION OF THE DRAWINGS

FIG. 2b is a detail of one component of the upper face of the reservoir layer illustrated in FIG. 2a.

FIGS. 17, 17A and 17B show an arrangement of microfluidics structures on a disc of the invention for performing multiple dilution of a biological sample (e.g., a drug).

FIGS. 19A and 19B illustrates longitudinal mixing accompanying fluid flow of two fluids mixing in a microchannel (FIG. 19A) and mixing of a first fluid with a second fluid located more distal from the center of rotation in a mixing microchannel.

FIG. 22 shows the arrangement of microfluidic structures in a single-level, two-split mixing microchannel.

FIG. 23 shows the arrangement of microfluidic structures in a two-level, two-split mixing microchannel.

FIG. 24 shows the arrangement of microfluidic structures in a two-level, two-split mixing microchannel.

FIG. 25 shows the arrangement of microfluidic structures in a two-level, six-split mixing microchannel.

FIG. 26 shows the arrangement of microfluidic structures in a two-level, two-split design fork mixing microchannel.

FIG. 27 shows the arrangement of microfluidic structures in an alternative embodiment of a two-level, two-split design fork mixing microchannel.

FIG. 32 shows an alternative embodiment of an arrangement of microfluidic structures in a single-channel, comb mixer.

FIGS. 35A and 35B are graphs showing the results of the dilution assays performed according to the disclosure in Example 2

DETAILED DESCRIPTION OF PREFERRED EMBODIMENTS

Figure 1:
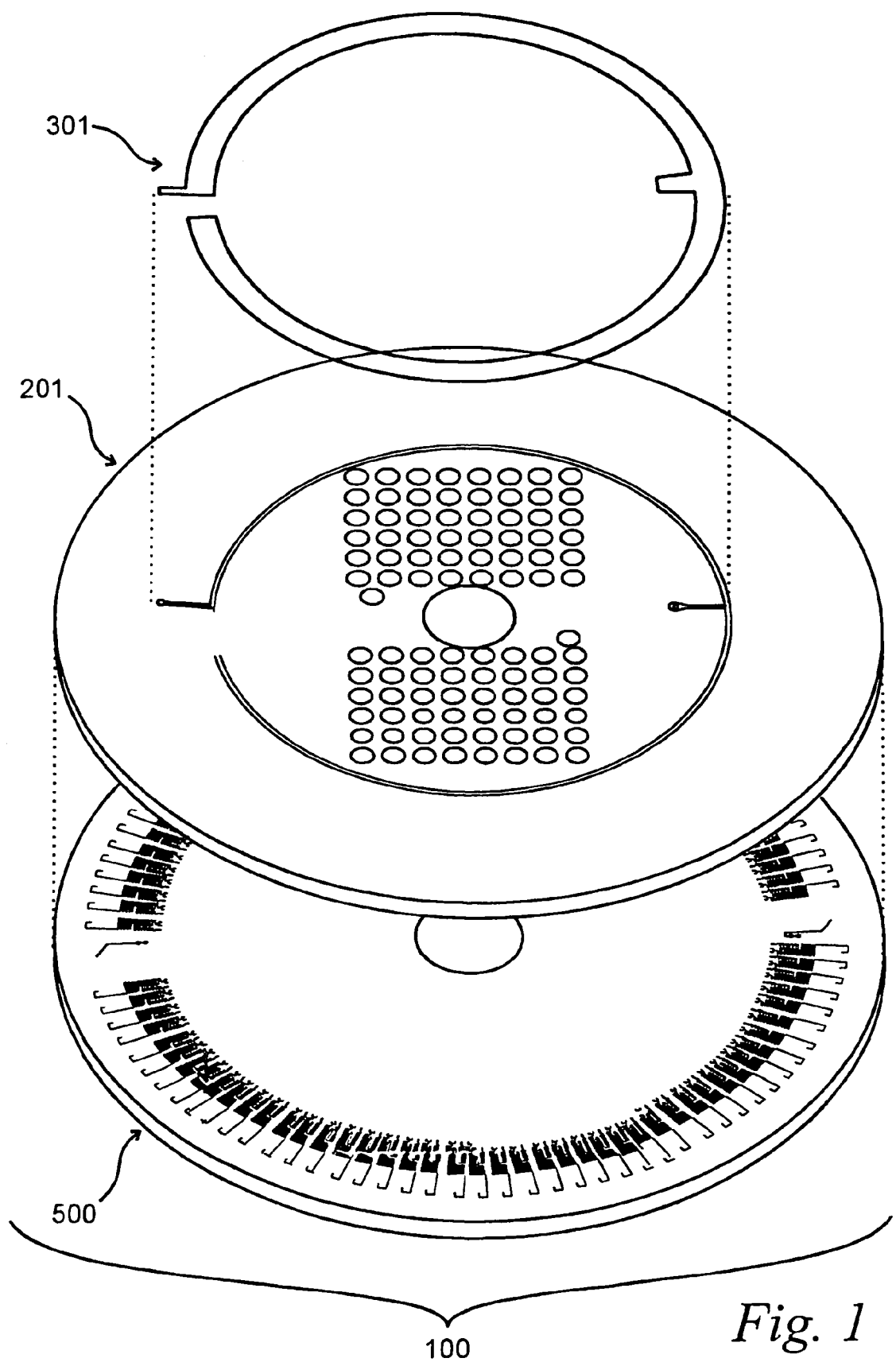
FIG. 1 depicts an exploded, oblique view of a microsystems platform of the invention.

This invention provides a microsystem platform and a micromanipulation device as disclosed in co-owned U.S. Pat. No. 6,063,589, issued May 16, 2000, and co-owned and co-pending patent applications U.S. Ser. Nos. 08/761,063, filed Dec. 5, 1996; Ser. No. 08/768,990, filed Dec. 18, 1996; Ser. No. 08/910,726, filed Aug. 12, 1997; Ser. No. 08/995,056, filed Dec. 19, 1997; Ser. No. 09/315,114, filed May 19, 1999, and Ser. No. 09/858,318, filed May 15, 2001, the disclosures of each of which are explicitly incorporated by reference herein, adapted for performing microanalytical and microsynthetic assays of biological samples.

For the purposes of this invention, the term "sample" will be understood to encompass any fluid, solution or mixture, either isolated or detected as a constituent of a more complex mixture, or synthesized from precursor species. In particular, the term "sample" will be understood to encompass any biological species of interest. The term "biological sample" or "biological fluid sample" will be understood to mean any biologically-derived sample, including but not limited to blood, plasma, serum, lymph, saliva, tears, cerebrospinal fluid, urine, sweat, plant and vegetable extracts, semen, and ascites fluid.

For the purposes of this invention, the term "a centripetally motivated fluid micromanipulation apparatus" is intended to include analytical centrifuges and rotors, microscale centrifugal separation apparatuses, and most particularly the microsystems platforms and disk handling apparatuses as described in co-owned U.S. Pat. No. 6,063,589, issued May 16, 2000, and co-owned and co-pending patent applications U.S. Ser. Nos. 08/761,063, filed Dec. 5, 1996; Ser. No. 08/768,990, filed Dec. 18, 1996; Ser. No. 08/910,726, filed Aug. 12, 1997; Ser. No. 08/995,056, filed Dec. 19, 1997; Ser. No. 09/315,114, filed May 19, 1999, and Ser. No. 09/858,318, filed May 15, 2001, the disclosures of each of which are explicitly incorporated by reference herein.

For the purposes of this invention, the term "microsystems platform" is intended to include centripetally-motivated microfluidics arrays as described in co-owned U.S. Pat. No. 6,063,589, issued May 16, 2000, and co-owned and co-pending patent applications U.S. Ser. Nos. 08/761,063, filed Dec. 5, 1996; Ser. No. 08/768,990, filed Dec. 18, 1996; Ser. No. 08/910,726, filed Aug. 12, 1997; Ser. No. 08/995,056, filed Dec. 19, 1997; Ser. No. 09/315,114, filed May 19, 1999, and Ser. No. 09/858,318, filed May 15, 2001, the disclosures of each of which are explicitly incorporated by reference herein.

For the purposes of this invention, the terms "capillary", "microcapillary" and "microchannel" will be understood to be interchangeable and to be constructed of either wetting or non-wetting materials where appropriate.

For the purposes of this invention, the term "reservoir," "assay chamber," "fluid holding chamber," "collection chamber" and "detection chamber" will be understood to mean a defined volume on a microsystems platform of the invention comprising a fluid.

For the purposes of this invention, the terms "entry port," "sample input," and "fluid input port" will be understood to mean an opening on a microsystems platform of the invention comprising a means for applying a fluid to the platform.

For the purposes of this invention, the terms "reagent input port" will be understood to mean an opening on a microsystems platform of the invention comprising a means for applying a fluid to the platform.

For the purposes of this invention, the term "capillary junction" will be understood to mean a region in a capillary or other flow path where surface or capillary forces are exploited to retard or promote fluid flow. A capillary junction is provided as a pocket, depression or chamber in a hydrophilic substrate that has a greater depth (vertically within the platform layer) and/or a greater width (horizontally within the platform layer) that the fluidics component (such as a microchannel) to which it is fluidly connected. For liquids having a contact angle less than 90° (such as aqueous solutions on platforms made with most plastics, glass and silica), flow is impeded as the channel cross-section increases at the interface of the capillary junction. The force hindering flow is produced by capillary pressure, that is inversely proportional to the cross sectional dimensions of the channel and directly proportional to the surface tension of the liquid, multiplied by the cosine of the contact angle of the fluid in contact with the material comprising the channel. The factors relating to capillarity in microchannels according to this invention have been discussed in co-owned U.S. Pat. No. 6,063,589, issued May 12, 2000 and in co-owned and co-pending U.S. patent application, Ser. No. 08/910,726, filed Aug. 12, 1997, incorporated by reference in its entirety herein.

Capillary junctions can be constructed in at least three ways. In one embodiment, a capillary junction is formed at the junction of two components wherein one or both of the lateral dimensions of one component is larger than the lateral dimension(s) of the other component. As an example, in microfluidics components made from "wetting" or "wettable" materials, such a junction occurs at an enlargement of a capillary as described in co-owned and co-pending U.S. Ser. Nos. U.S. Ser. Nos. 08/761,063, filed Dec. 5, 1996; Ser. No. 08/768,990, filed Dec. 18, 1996; and Ser. No. 08/910,726, filed Aug. 12; 1997. Fluid flow through capillaries is inhibited at such junctions. At junctions of components made from non-wetting or non-wettable materials, on the other hand, a constriction in the fluid path, such as the exit from a chamber or reservoir into a capillary, produces a capillary junction that inhibits flow. In general, it will be understood that capillary junctions are formed when the dimensions of the components change from a small diameter (such as a capillary) to a larger diameter (such as a chamber) in wetting systems, in contrast to non-wettable systems, where capillary junctions form when the dimensions of the components change from a larger diameter (such as a chamber) to a small diameter (such as a capillary).

A second embodiment of a capillary junction is formed using a component having differential surface treatment of a capillary or flow-path. For example, a channel that is hydrophilic (that is, wettable) may be treated to have discrete regions of hydrophobicity (that is, non-wettable). A fluid flowing through such a channel will do so through the hydrophilic areas, while flow will be impeded as the fluid-vapor meniscus impinges upon the hydrophobic zone.

The third embodiment of a capillary junction according to the invention is provided for components having changes in both lateral dimension and surface properties. An example of such a junction is a microchannel opening into a hydrophobic component (microchannel or reservoir) having a larger lateral dimension. Those of ordinary skill will appreciate how capillary junctions according to the invention can be created at the juncture of components having different sizes in their lateral dimensions, different hydrophilic properties, or both.

For the purposes of this invention, the term "capillary action" will be understood to mean fluid flow in the absence of rotational motion or centripetal force applied to a fluid on a rotor or platform of the invention and is due to a partially or completely wettable surface.

For the purposes of this invention, the term "capillary microvalve" will be understood to mean a capillary microchannel comprising a capillary junction whereby fluid flow is impeded and can be motivated by the application of pressure on a fluid, typically by centripetal force created by rotation of the rotor or platform of the invention. Capillary microvalves will be understood to comprise capillary junctions that can be overcome by increasing the hydrodynamic pressure on the fluid at the junction, most preferably by increasing the rotational speed of the platform.

For the purposes of this invention, the term "in fluid communication" or "fluidly connected" is intended to define components that are operably interconnected to allow fluid flow between components.

For the purposes of this invention, the term "air displacement channels" will be understood to include ports in the surface of the platform that are contiguous with the components (such as microchannels, chambers and reservoirs) on the platform, and that comprise vents and microchannels that permit displacement of air from components of the platforms and rotors by fluid movement.

The microplatforms of the invention (preferably and hereinafter collectively referred to as "disks" or "discs"; for the purposes of this invention, the terms "microplatform", "microsystems platform", "disc" and "disk" are considered to be interchangeable) are provided to comprise one or a multiplicity of microsynthetic or microanalytic systems (termed "microfluidics structures" herein). Such microfluidics structures in turn comprise combinations of related components as described in further detail herein that are operably interconnected to allow fluid flow between components upon rotation of the disk. These components can be microfabricated as described below either integral to the disk or as modules attached to, placed upon, in contact with or embedded in the disk. For the purposes of this invention, the term "microfabricated" refers to processes that allow production of these structures on the sub-millimeter scale. These processes include but are not restricted to molding, photolithography, etching, stamping and other means that are familiar to those skilled in the art.

The invention also comprises a micromanipulation device for manipulating the disks of the invention, wherein the disk is rotated within the device to provide centripetal force to effect fluid flow on the disk. Accordingly, the device provides means for rotating the disk at a controlled rotational velocity, for stopping and starting disk rotation, and advantageously for changing the direction of rotation of the disk. Both electromechanical means and control means, as further described herein, are provided as components of the devices of the invention. User interface means (such as a keypad and a display) are also provided, as further described in co-owned U.S. Pat. No. 6,063,589, issued May 16, 2000, and co-owned and co-pending patent applications U.S. Ser. Nos. 08/761, 063, filed Dec. 5, 1996; Ser. No. 08/768,990, filed Dec. 18, 1996; Ser. No. 08/910,726, filed Aug. 12, 1997; Ser. No. 08/995,056, filed Dec. 19, 1997; Ser. No. 09/315,114, filed May 19, 1999, and Ser. No. 09/858,318, filed May 15, 2001, the disclosures of each of which are explicitly incorporated by reference herein.

The invention provides a combination of specifically-adapted microplatforms that are rotatable, analytic/synthetic microvolume assay platforms, and a micromanipulation device for manipulating the platform to achieve fluid movement on the platform arising from centripetal force on the platform as result of rotation. The platform of the invention is preferably and advantageously a circular disk; however, any platform capable of being rotated to impart centripetal for a fluid on the platform is interned to fall within the scope of the invention. The micromanipulation devices of the invention are more fully described in co-owned and co-pending U.S. Ser. Nos. U.S. Ser. Nos. 08/761,063, filed Dec. 5, 1996; Ser. No. 08/768,990, filed Dec. 18, 1996; Ser. No. 08/910,726, filed Aug. 12, 1997; Ser. No. 08/995,056, filed Dec. 19, 1997; Ser. No. 09/315,114, filed May 19, 1999, and Ser. No. 09/858, 318, filed May 15, 2001, the disclosures of each of which are explicitly incorporated by reference herein.

Fluid (including reagents, samples and other liquid components) movement is controlled by centripetal acceleration due to rotation of the platform. The magnitude of centripetal acceleration required for fluid to flow at a rate and under a pressure appropriate for a particular microfluidics structure on the microsystems platform is determined by factors including but not limited to the effective radius of the platform, the interior diameter of microchannels, the position angle of the microchannels on the platform with respect to the direction of rotation, and the speed of rotation of the platform. In certain embodiments of the methods of the invention an unmetered amount of a fluid (either a sample or reagent solution) is applied to the platform and a metered amount is transferred from a fluid reservoir to a microchannel, as described in co-owned U.S. Pat. No. 6,063,589, issued May 16, 2000, and co-owned and co-pending patent applications U.S. Ser. Nos. 08/761,063, filed Dec. 5, 1996; Ser. No. 08/768,990, filed Dec. 18, 1996; Ser. No. 08/910,726, filed Aug. 12, 1997; Ser. No. 08/995,056, filed Dec. 19, 1997; Ser. No. 09/315,114, filed May 19, 1999, and Ser. No. 09/858,318, filed May 15, 2001, the disclosures of each of which are explicitly incorporated by reference herein. In preferred embodiments, the metered amount of the fluid sample provided on an inventive platform is from about 1 nL to about 500µL. In these embodiments, metering manifolds comprising one or a multiplicity of metering capillaries are provided to distribute the fluid to a plurality of components of the microfluidics structure.

The components of the platforms of the invention are in fluidic contract with one another. In preferred embodiments, fluidic contact is provided by microchannels comprising the surface of the platforms of the invention. Microchannel sizes are optimally determined by specific applications and by the amount of and delivery rates of fluids required for each particular embodiment of the platforms and methods of the invention. Microchannel sizes can range from 0.1 µm to a value close to the thickness of the disk (e.g., about 1 mm); in preferred embodiments, the interior dimension of the microchannel is from 0.5 µm to about 500 µm. Microchannel and reservoir shapes can be trapezoid, circular or other geometric shapes as required. Microchannels preferably are embedded in a microsystem platform having a thickness of about 0.1 to 25 mm, wherein the cross-sectional dimension of the microchannels across the thickness dimension of the platform is less than 1 mm, and can be from 1 to 90 percent of said cross-sectional dimension of the platform. Sample reservoirs, reagent reservoirs, reaction chambers, collection chambers, detections chambers and sample inlet and outlet ports preferably are embedded in a microsystem platform having a thickness of about 0.1 to 25 mm, wherein the cross-sectional dimension of the microchannels across the thickness dimension of the platform is from 1 to 75 percent of said cross-sectional dimension of the platform. In preferred embodiments, delivery of fluids through such channels is achieved by the coincident rotation of the platform for a time and at a rotational velocity sufficient to motivate fluid movement between the desired components.

The flow rate through a microchannel of the invention is inversely proportional to the length of the longitudinal extent or path of the microchannel and the viscosity of the fluid and directly proportional to the product of the square of the hydraulic diameter of the microchannel, the square of the rotational speed of the platform, the average distance of the fluid in the channels from the center of the disk and the radial extent of the fluid subject to the centripetal force. Since the hydraulic diameter of a channel is proportional to the ratio of the cross-sectional area to cross-sectional perimeter of a channel, one can judiciously vary the depth and width of a channel to affect fluid flow (see Duffy et al., 1998, *Anal. Chem*. 71: 4669-4678 and co-owned and co-pending patent applications U.S. Ser. Nos. 08/761,063, filed Dec. 5, 1996 and Ser. No. 08/768,990, filed Dec. 18, 1996, incorporated by reference).

For example, fluids of higher densities flow more rapidly than those of lower densities given the same geometric and rotational parameters. Similarly, fluids of lower viscosity flow more rapidly than fluids of higher viscosity given the same geometric and rotational parameters. If a microfluidics structure is displaced along the radial direction, thereby changing the average distance of the fluid from the center of the disc but maintaining all other parameters, the flow rate is affected: greater distances from the center result in greater flow rates. An increase or a decrease in the radial extent of the fluid also leads to an increase or decrease in the flow rate. These dependencies are all linear. Variation in the hydraulic diameter results in a quartic dependence of flow rate on hydraulic diameter (or quadratic dependence of fluid flow velocity on hydraulic diameter), with larger flow rates corresponding to larger diameters. Finally, an increase in the rotational rate results in a quadratic increase in the flow rate or fluid flow velocity.

Input and output (entry and exit) ports are components of the microplatforms of the invention that are used for the introduction or removal of fluid components. Entry ports are provided to allow samples and reagents to be placed on or injected onto the disk; these types of ports are generally located towards the center of the disk. Exit ports are also provided to allow products to be removed from the disk. Port shape and design vary according specific applications. For example, sample input ports are designed, inter alia, to allow capillary action to efficiently draw the sample into the disk. In addition, ports can be configured to enable automated sample/reagent loading or product removal. Entry and exit ports are most advantageously provided in arrays, whereby multiple samples are applied to the disk or to effect product removal from the microplatform.

In some embodiments of the platforms of the invention, the inlet and outlet ports are adapted to the use of manual pipettors and other means of delivering fluids to the reservoirs of the platform. In alternative, advantageous embodiments, the platform is adapted to the use of automated fluid loading devices. One example of such an automated device is a single pipette head located on a robotic arm that moves in a direction radially along the surface of the platform. In this embodiment, the platform could be indexed upon the spindle of the rotary motor in the azimuthal direction beneath the pipette head, which would travel in the radial direction to address the appropriate reservoir.

Another embodiment is a pipettor head adapted to address multiple reservoirs, either a subset of or all of the reservoirs on the platform surface. For embodiments where the pipettor head addresses a subset of the reservoirs, a single head may for example be composed of a linear array of pipette heads. For example, the entry ports of FIG. 1 might be addressed by indexing such a linear head in the direction transverse to the pipette tips. In other embodiments, pipette heads may be used which can simultaneously address all entry ports (for example, a 96-tip head). In these embodiments, there may be a distinction between sample entry ports—needed for the delivery of many samples—and reagent entry ports, through which larger volumes or reagent are delivered for use in reactions with all samples. A pipetting device that can simultaneously address all sample entry ports as well as reagent ports might consist of a standard multipipettor with a few added, large-volume delivery tips.

Also included in air handling systems on the disk are air displacement channels, whereby the movement of fluids displaces air through channels that connect to the fluid-containing microchannels retrograde to the direction of movement of the fluid, thereby providing a positive pressure to further motivate movement of the fluid.

Platforms of the invention such as disks and the microfluidics components comprising such platforms are advantageously provided having a variety of composition and surface coatings appropriate for particular applications. Platform composition will be a function of structural requirements, manufacturing processes, and reagent compatibility/chemical resistance properties. Specifically, platforms are provided that are made from inorganic crystalline or amorphous materials, e.g. silicon, silica, quartz, inert metals, or from organic materials such as plastics, for example, poly(methyl methacrylate) (PMMA), acetonitrile-butadiene-styrene (ABS), polycarbonate, polyethylene, polystyrene, polyolefins, polypropylene and metallocene. These may be used with unmodified or modified surfaces as described below. The platforms may also be made from thermoset materials such as polyurethane and poly(dimethyl siloxane) (PDMS). Also provided by the invention are platforms made of composites or combinations of these materials; for example, platforms manufactures of a plastic material having embedded therein an optically transparent glass surface comprising the detection chamber of the platform. Alternately, platforms composed of layers made from different materials may be made. The surface properties of these materials may be modified for specific applications, as disclosed in co-owned U.S. Pat. No. 6,063,589, issued May 16, 2000, and co-owned and co-pending patent applications U.S. Ser. Nos. 08/761,063, filed Dec. 5, 1996; Ser. No. 08/768,990, filed Dec. 18, 1996; Ser. No. 08/910,726, filed Aug. 12, 1997; Ser. No. 08/995,056, filed Dec. 19, 1997; Ser. No. 09/315,114, filed May 19, 1999, and Ser. No. 09/858,318, filed May 15, 2001, the disclosures of each of which are explicitly incorporated by reference herein.

Preferably, the disk incorporates microfabricated mechanical, optical, and fluidic control components on platforms made from, for example, plastic, silica, quartz, metal or ceramic. These structures are constructed on a sub-millimeter scale by molding, photolithography, etching, stamping or other appropriate means, as described in more detail below. It will also be recognized that platforms comprising a multiplicity of the microfluidic structures are also encompassed by the invention, wherein individual combinations of microfluidics and reservoirs, or such reservoirs shared in common, are provided fluidly connected thereto. An example of such a platform is shown in FIG. 1.

This invention specifically provides microfluidic structures adapted for and arranged for sample dilution as part of a platform using centripetal acceleration to actuate fluid flow. Structures are described herein that can be used to perform serial dilution, parallel dilution, or a combination of both dilution types. In certain embodiments, the invention provides apparatus that can dilute a single volume of sample fluid into many less concentrated sample volumes by combining various volumes of sample with various volumes of diluent. For accomplishing serial dilution, a volume that was previously-diluted on the platform is further diluted by one or more successive stages of dilution with the same or a different diluent.

The apparatus of the invention advantageously permits dilution of a sample, preferably a chemical sample and most preferably a biological sample, requiring a decreased number of liquid handling steps, particularly in instances using distribution of a common reagent. Such a common reagent needs to be manually or automatically pipetted only once or twice onto the platform rather than for each separate assay, as in the case, for example, of microtiter plates. Liquid handling steps are further decreased by allowing the other component of the assay (for example, a drug, compound, or sample) to be diluted directly on the platform, instead of by a liquid handler prior to loading. Because many assays are run with a dilution series of a particular drug, compound, or sample, such an automatic dilution structure is widely applicable to many types of assays.

As provided herein, the dilution-specific microfluidic structures are directly incorporated into the platform. Because very small volume features ($\leq 1$ nl) can be fabricated in the platform, it is possible to accurate and reproducibly meter such volumes in the platform. This is well beyond the capability of most liquid handling machines, many of which cannot accurately dispense less than 1 microliter. Moreover, although some liquid handlers can dispense less than 1 microliter, they are unable to do so without handling at least 1 microliter of sample, meaning that there is still substantial waste. In contrast, the apparatus provided by the invention can reproducibly and accurately dispense small volumes while utilizing a minimal amount of liquid. Moreover, the apparatus and practice of the methods of the invention permits dilution to much lower concentrations and over a large range of orders of magnitude than most other methods.

As disclosed herein, dilution according to the invention is accomplished by loading a sample, for example a drug, directly onto the platform. Subsequently, after motivation of fluid flow by centripetal acceleration the initial drug solution is subsequently diluted to one or more lower concentrations. Each dilution is performed by combining a metered volume of drug with an amount of a diluent until a final metered volume is obtained. Additional dilutions can be performed in two ways. Parallel dilutions can be performed at the same time by changing the amount of drug or diluent that is metered. Ser. dilutions can be performed by using all or a portion of the first dilution in a second dilution stage. In the preferred embodiment, a plurality of dilution chambers are used in a first stage (parallel dilution) and one or more of the volumes of the first-stage dilution chambers are used as sample for a second dilution stage (serial dilution).

For high-throughput multiplexed assays, it is convenient to start with the same metered sample volume for each assay. Therefore, in preferred embodiments volumes of drug and diluent are added to provide a final mixed (diluted) volume that is the same in the case of each dilution. When a plurality of dilutions are performed in parallel, the volume of drug to be used in each dilutions varies inversely with the volume of diluent to be used. For example, if a total dilution volume of 2 µl is desired for each dilution, then the sum of volumes of drug and diluent must equal 2 µl. Therefore, as the metered drug volume increases, the metered diluent volume decreases.

Platform Manufacture and Assembly

Referring now to the Figures for a more thorough description of the invention, FIG. 1 shows an exploded view of an example of a disc appropriate for large numbers of similar or identical microfluidics structures for performing, inter alia, liquid-phase assays. The disc shown here enables the performance of 96 parallel assays of the same form. The assays have the general form: mix first fluid A with second fluid B, and then mix the combined fluids (A+B) with third fluid C. In practice, the fluid A may actually be a number of fluids, $A_1$, $A_2, \ldots A_i, \ldots A_n$, where n is the total number of assays to be performed on independent fluids. Furthermore, the disc is designed for loading fluids thereupon through ports constructed in the platform. For example, one fluid, A, herein termed "sample", is loaded through 96 independent entry ports. The second fluid, B, is loaded in a volume somewhat greater than 96 times the volume required for each assay into a single entry port. The third fluid, C, is similarly loaded into a single entry port. The volumes of each of the reservoirs containing fluids A, B and C, or the amount of fluid A, B or C loaded onto the disk, can be different, depending on the requirements of the assay. The disc is configured so that rotation of the disc after loading, under a prescribed rotational profile, effects the following fluid motions: Delivery of individual samples $A_i$ to assay structures within the disc; delivery of metered aliquots of fluid B to individual assay structures within the disc; delivery of metered aliquots of fluid C to individual assay structures within the disc; "isolation" of individual assay structure volumes of fluids B and C through the use of overflow reservoirs which take excess fluid and introduce air bubbles between individual assay structures; and the performance of the assay as described above, wherein the discs effect two fluid mixing steps. The number of fluids and sequence of mixing steps can be arbitrary, e.g., $(A_i+B)+(B+C)$. The total number of fluids can also be arbitrary, and the three-dimensional nature of the microfluidic network allows the "crossing over" of numerous channels. Features of this device include: a) "samples" that must be loaded in large numbers can be loaded into a standard format accessible to laboratory robotics or standard automated pipetting systems; b) common reagents need to be loaded only once each, and without high precision. These features integrate the device into existing laboratory infrastructure while providing the advantages of reduced operating time for fluid transfers, enclosed assays for reduction of evaporation and contamination, and the removal of liquid-air meniscus for detection.

This disc illustrates that identical assays may be made by repeating assay structures around the disc at a given radius as well as modifying the structures for placement at different radial positions. In this way, it is possible to fully cover the surface of the disc with microfluidics structures for performing assays. The maximum number of assays that may be performed will depend upon the volume of fluid that cay be manipulated reproducibly, i.e., the minimum reproducible dimensions with which the disc may be fabricated, and the amount of hydrodynamic pressure required to drive small volumes of fluid through microchannels at convenient rotational rates. Taking these considerations into account, it is estimated that greater than 10,000 assays having volumes of 1-5 nL can be created in a circular platform having a 6 cm radius.

In FIG. 1, platform 100 is composed of at least 3 component layers. A reservoir layer 201 having features on the lower face, or both the upper and lower faces, is used. In cases where there are fluidic channels on the upper surface, a sealing film 301 is used to enclose those channels. The "lower" surface of the reservoir layer 201 is bonded to a microfluidics layer 500. The upper surface of the reservoir layer contains the fluid entry ports; it may also contain one or more distribution manifolds as described herein for distributing one or more common fluids. The bottom face of the reservoir layer, when mated with the microfluidic layer described below, forms a complete network of enclosed channels and reservoirs through which fluids flows under the impetus of centripetal force created by rotation of the platform about a central axis. Fluid flow permits mixing of various component fluids in the assay and movement of the fluids from sample and reagent chambers through mixing structures and into assay reaction chambers. In addition, fluid flow can be effectuated to include incubation and wash steps, using structures disclosed in co-owned U.S. Pat. No. 6,063,589, issued May 16, 2000 and incorporated by reference herein. Fluid flow rates range from about 1 nL/s to about 1000 µL/s at rotational speeds of from about 4-30,000 rpm. "Passive" or capillary valves are preferably used to control fluid flow in the platform as described in co-owned U.S. Pat. No. 6,063,589, issued May 16, 2000, and co-owned and co-pending patent applications U.S. Ser. Nos. 08/761,063, filed Dec. 5, 1996; Ser, No. 08/768,990, filed Dec. 18, 1996; Ser. No. 08/910,726, filed Aug. 12, 1997; Ser, No. 08/995,056, filed Dec. 19, 1997; Ser. No. 09/315,114, filed May 19, 1999, and Ser. No. 09/858,318, filed May 15, 2001, the disclosures of each of which are explicitly incorporated by reference herein. In the operation of the platforms of the invention, competition between rotationally-induced hydrostatic pressure and the capillary pressure exerted in small channels and orifices are exploited to provide a rotation-depending gating or valving system. After fluids are deposited in detection chambers positioned towards the outer edge of the platform, an optical signal is detected.

Platform 100 is preferably provided in the shape of a disc, a circular planar platform having a diameter of from about 10 mm to about 50 mm and a thickness of from about 0.1 mm to about 25 mm. Each layer comprising the platform preferably has a diameter that is substantially the same as the other layers, although in some embodiments the diameters of the different layers are not required to completely match. Each layer has a thickness ranging from about 0.1 mm to about 25 mm, said thickness depending in part on the volumetric capacity of the microfluidics components contained therein.

Reservoir Layer

Figure 2A:
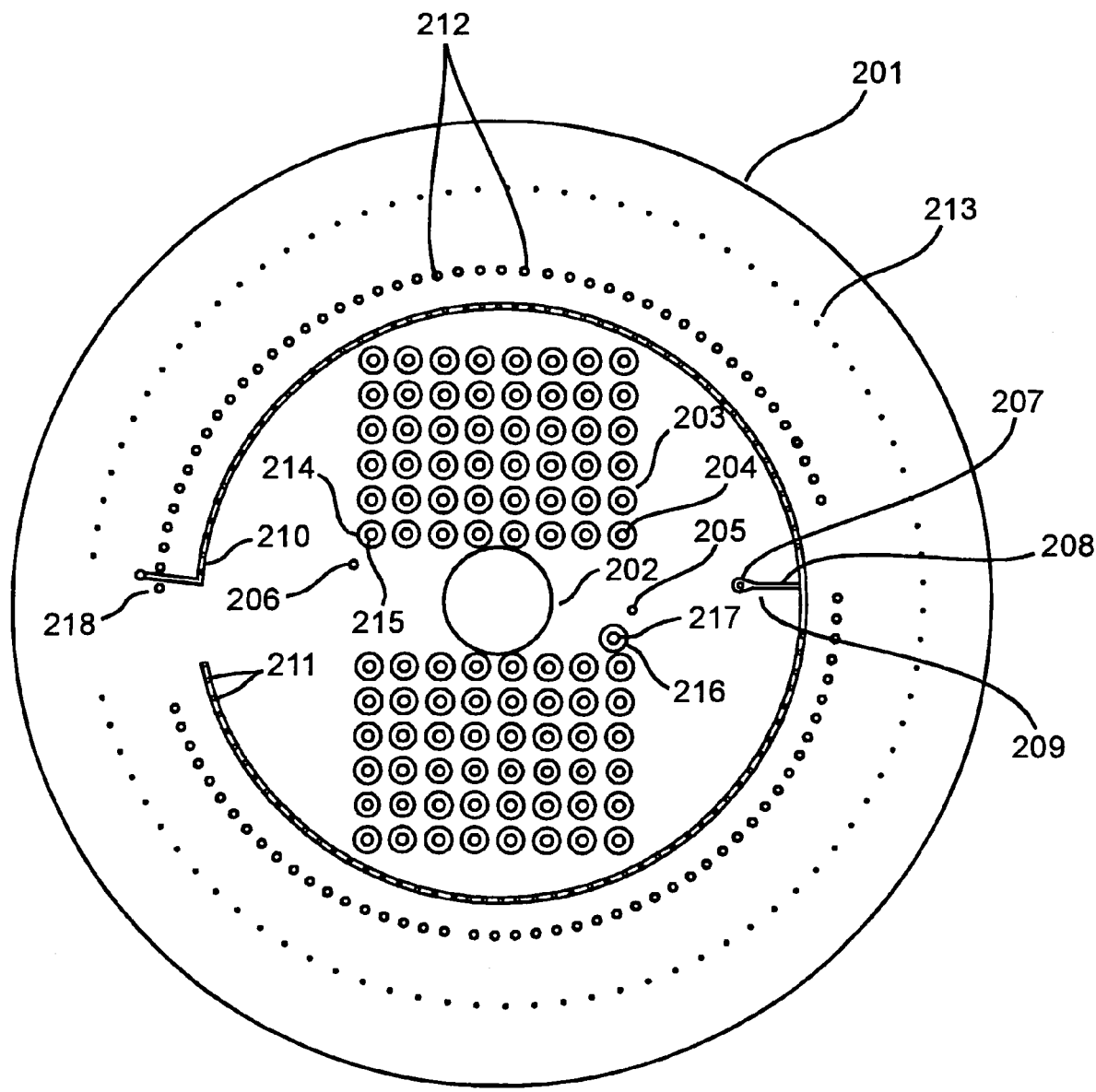
FIG. 2a depicts a plan view of the upper face of one component of the microsystems platform shown in exploded, oblique view in FIG. 1, the reservoir layer.

The structure of top surface of the reservoir layer 201 is shown in FIG. 2a.

Reservoir layer 201 is preferably provided in the shape of a disc, a circular planar platform having a diameter of from about 10 mm to about 50 mm and a thickness of from about 0.1 mm to about 25 mm. The layer preferably comprises a center hole 202 for mounting on a spindle, having a diameter of from about 1 mm to about 20 mm. Center hole 202 can be replaced by an extruded fitting for connection to a spindle, or may be absent entirely, in which case registry and connection to the spindle is accomplished using the attached microfluidic layer or another portion of the surface of the platform.

FIG. 2a illustrates a variety of structures necessary for device function. These include "sample" or fluid entry ports that are comprised of a through hole 204 communicating between the two faces of the disc and in some embodiments a conical or cup-like depression 203. The depression aids in the placement of pipette tips when the device is used manually. These entry holes are typically arrayed in a rectangular pattern with a spacing to permit an automated pipetting device such as an 8-tip linear or 96-tip rectangular pipetting head to be used. For such devices the spacing of entry ports is typically 9 mm or 4.5 mm, and the arrays are typically 8×12 or 16×24 elements in size. These ports may also be placed in the pattern of a 1536-well plate, which has a spacing of 2.25 mm and consists of 32×48 elements. They may also be placed in an arbitrary pattern for manual use or use with custom devices. The upper surface also contains entry ports for the addition of the two common reagents, comprised respectively of 214+215 and 216+217. These ports have dimensions adapted to automated loading devices such as micropipettors, for example, a standard 200 µL plastic pipette tip of tip diameter 1.5 mm; micropipette tips of diameter 1 mm; piezoelectric or ceramic drop delivery systems; and inkjet-based fluid delivery systems. For non-contact delivery systems such as piezoelectric or inkjet delivery, the dimensions of the ports must be a few times greater than the size of the droplets, e.g., 0.2 mm for a 1 nL drop. Corresponding to these latter entry ports are air ports 205 and 206 that allow air to escape from the common reagent reservoirs 401 and 402 (discussed below). The disc is able to distribute three fluids to an arbitrary port only by having a three-dimensional construction: fluid paths must "cross over" one another. As a result, some of the fluid motion occurs on the upper face of 201. Reagent aliquotting manifold 210 is such a distribution channel; its connection to bulk reagent reservoir 402 is via through hole 207 and exit channel 208. Along the manifold 210 are vias 211 which penetrate from one side of the disc to the other, allowing fluids to be distributed from the top to the bottom of the disc. The manifold 210 terminates in a via 218 which communicates with an overflow reservoir 403 discussed below. Also visible on the upper surface are air-ports 212 and 213 whose function will be discussed further below.

Figure 2B:
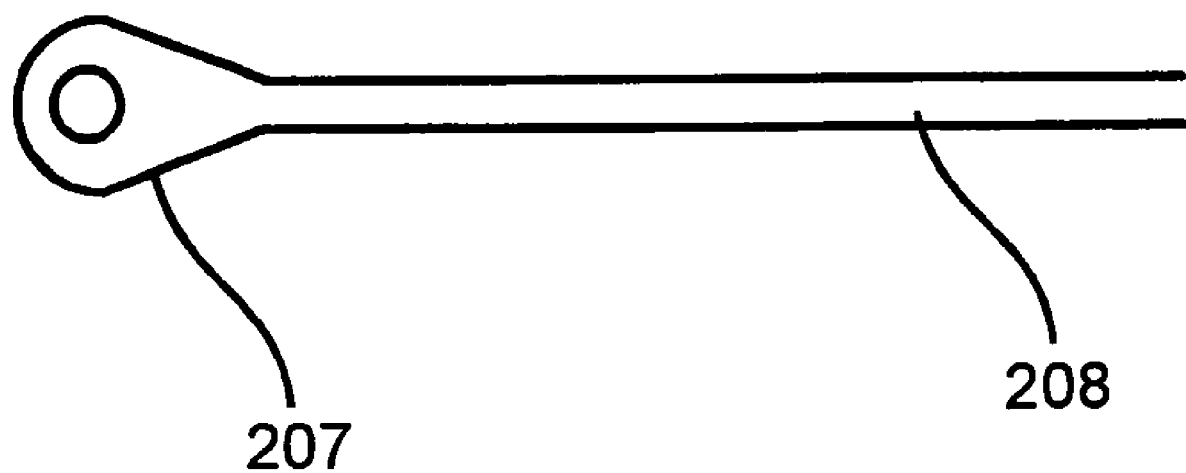

FIG. 2b is a detail of the fluid entry to the manifold. The through-hole 207 connects the upper surface of the disc within the channel 208 to the reservoir 402 on the lower surface of the disc.

Figure 3:
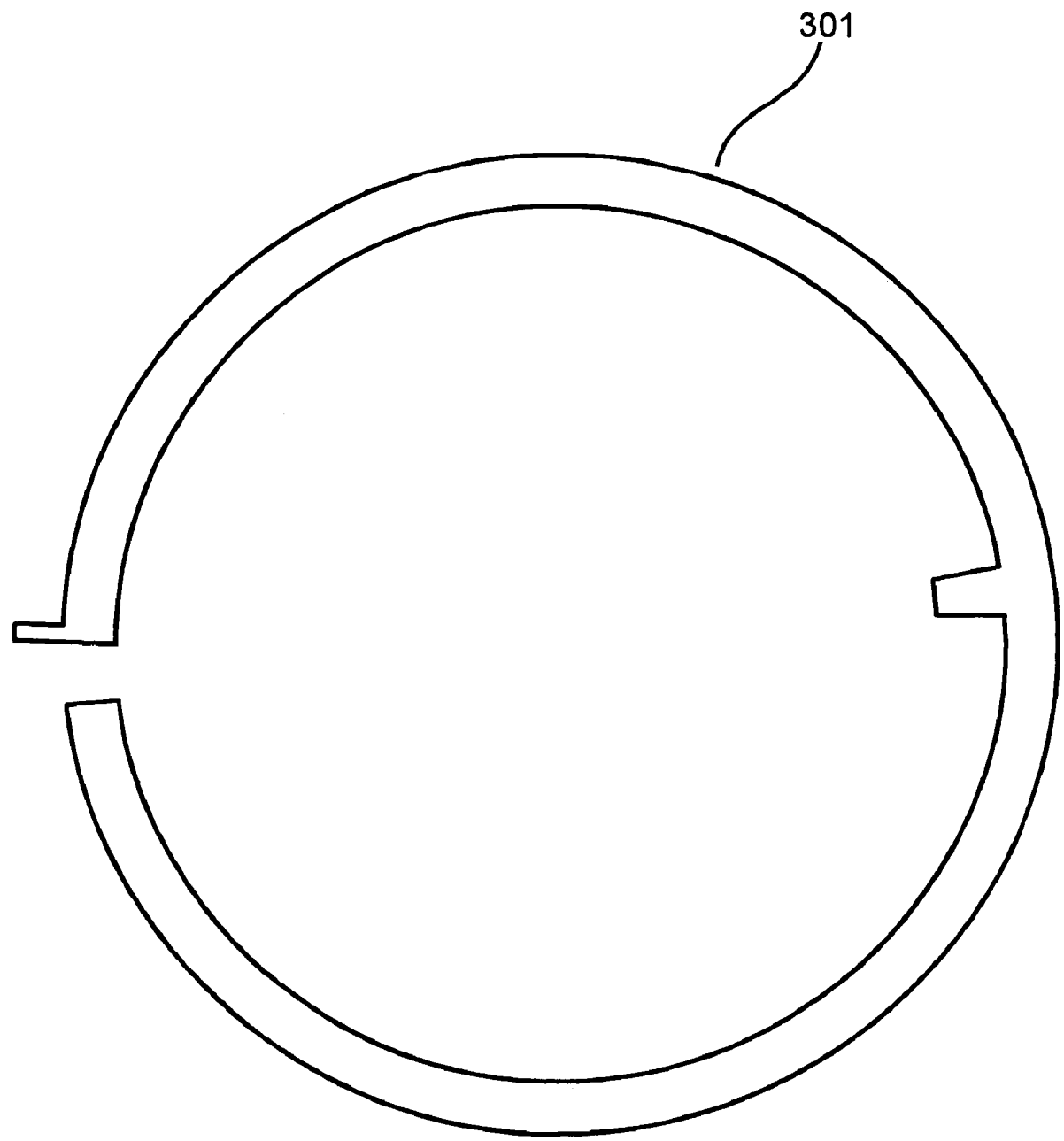
FIG. 3 is a plan view of another component of the microsystems platform of FIG. 1, the upper sealing film.

FIG. 3 shows the sealing film 301. The sealing film is typically of a thin, flexible material that can be sealed to the upper surface of the disc using an adhesive or heat-bonded into place, such that it seals all fluid channels. It is also shaped such that fluid entry ports and air vents are not blocked.

Figure 4A:
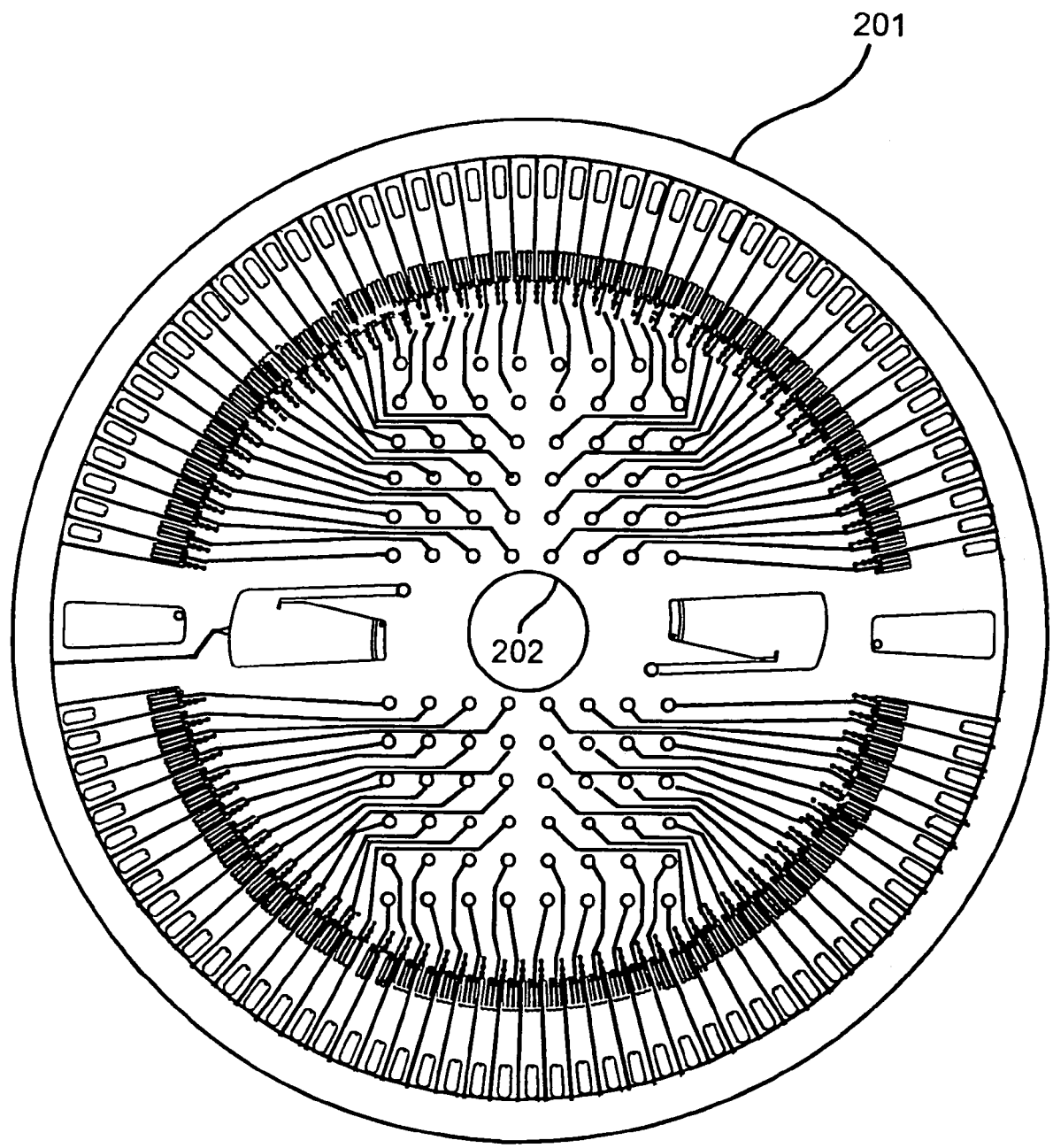
FIG. 4a depicts a plan view of the lower face of the reservoir layer.

FIG. 4a illustrates the bottom surface of the reservoir layer 201. Shown here are a number of through features from FIG. 2b, including the entry vias 204. Also shown are the common reagent reservoirs 401 and 402. Reservoir 401 distributes fluids along the lower face of the reservoir layer, while 402 distributes fluids through manifold 210 on the upper surface. Also shown are the overflow reservoirs 403 and 404 corresponding to reagent reservoirs 402 and 401, respectively.

Figure 4B:
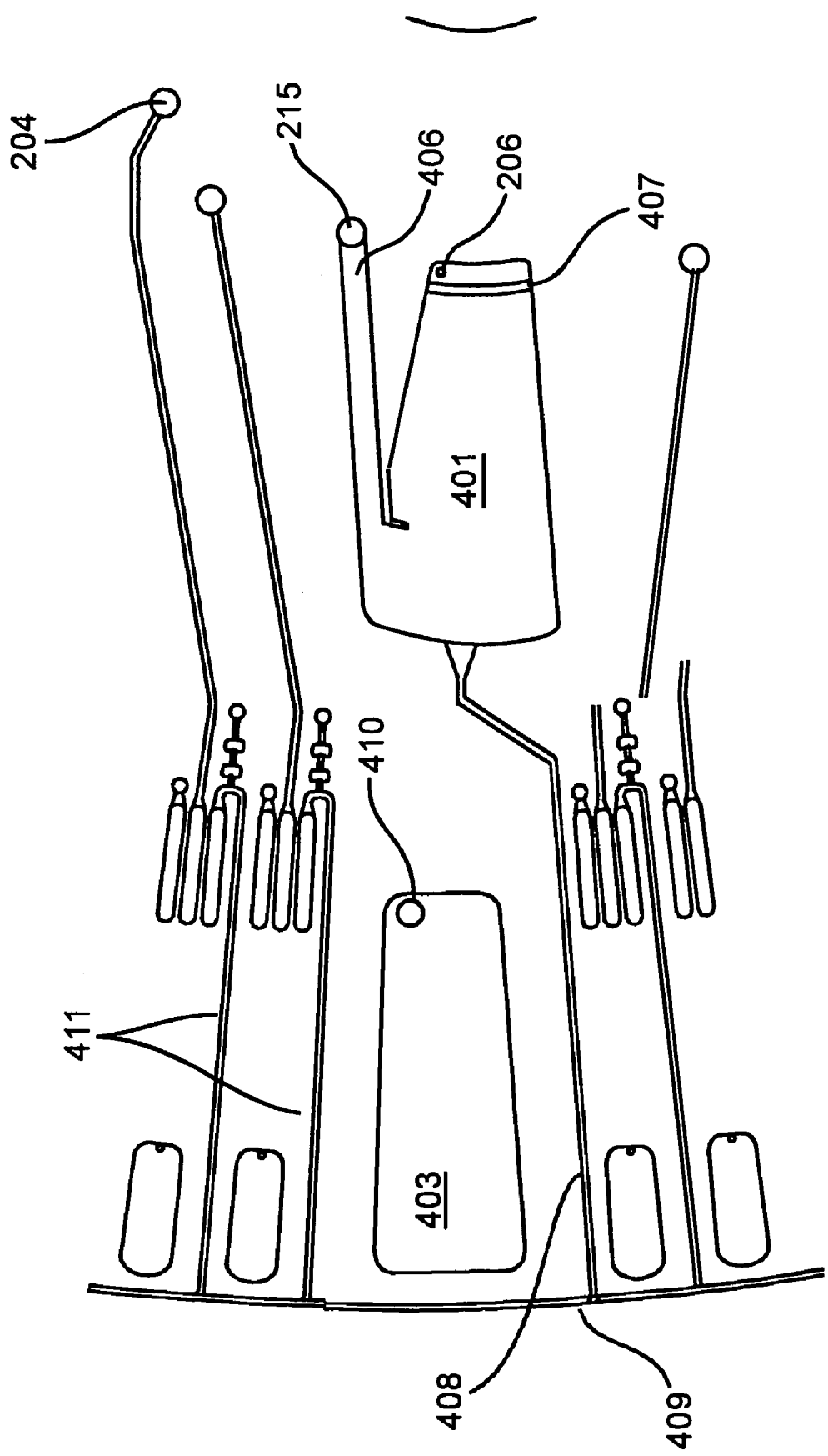
FIG. 4b is a detail of the lower face of the reservoir layer showing the second reagent addition reservoir and first reagent overflow reservoir.

FIG. 4b is a detail of the region around reagent reservoir 401. The reservoir is accessed through hole 215 and entry passageway 406; this may be shaped as shown to prevent flow of fluid toward the air vent 206. In addition, the depth of the reservoir 407 can be contoured to prevent fluid from reaching the hole 206 before the remainder of the reservoir has been filled. The reservoir 401 is connected via a channel 408 to a distribution manifold 409 through which the reagent is distributed. The fluid samples enter via ports 204 and channels 411.

Figure 4C:
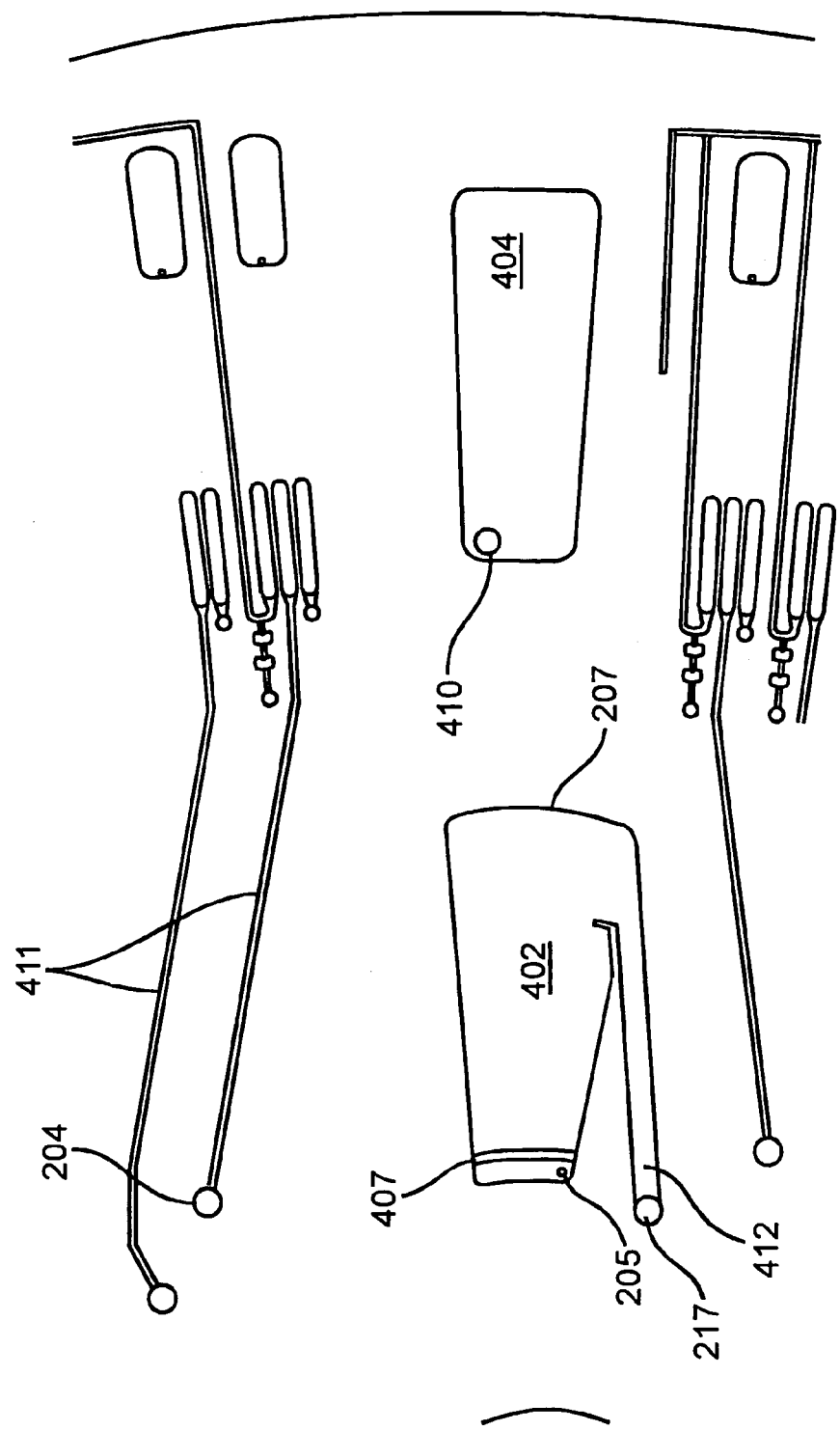
FIG. 4c is a detail of the lower face of the reservoir layer showing the first reagent addition reservoir and second reagent overflow reservoir.

FIG. 4c is a detail of the region around reagent reservoir 402. The reservoir is accessed through hole 217 and entry passageway 412; this may be shaped as shown to prevent flow of fluid toward the air vent 205. In addition, a restriction in depth of the reservoir 407 can successfully prevent fluid from reaching the hole 206 before the remainder of the reservoir has been filled. The reservoir 402 also contains a via 207 which communicates with the manifold 210 on the upper surface of the disc.

Figure 4D:
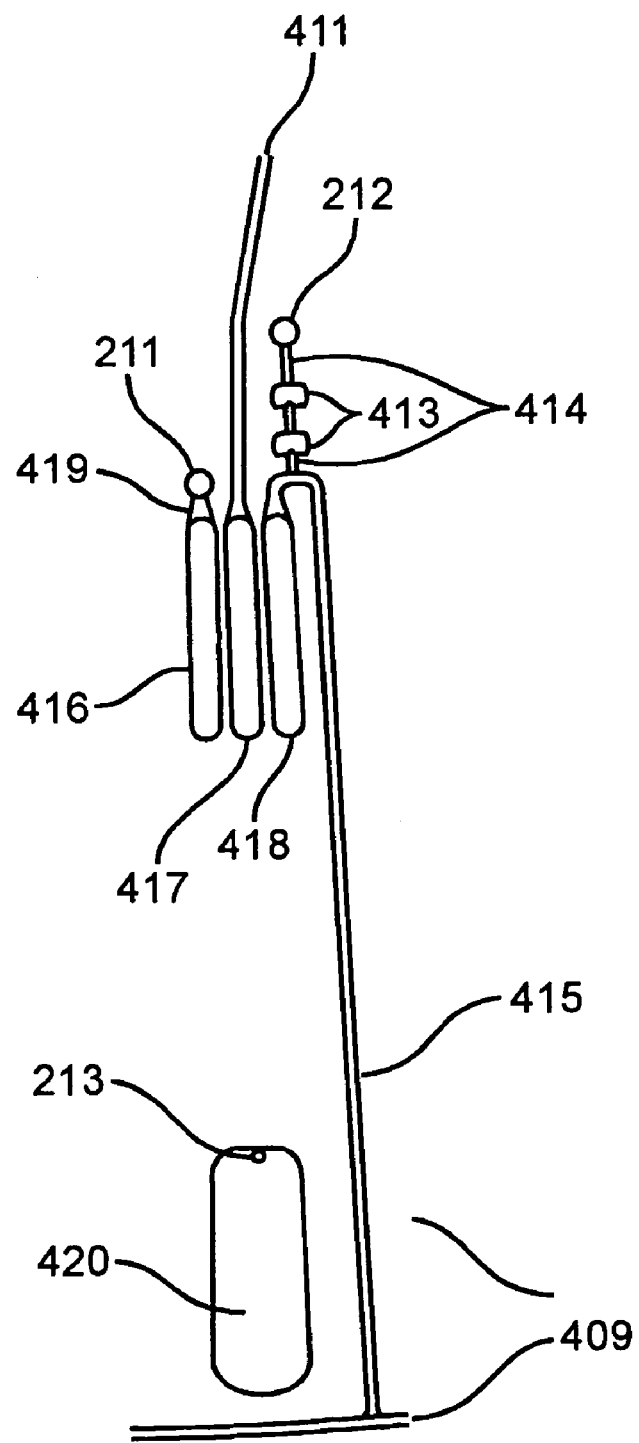
FIG. 4d is a detail of the lower face of the reservoir layer showing one series of sample and reagent reservoirs, channels, and a detection cuvette for a single microdevice that performs a single measurement.

FIG. 4d illustrates an expanded view of a section of the reservoir layer showing the reservoirs involved in a single assay. As shown in the Figure, this embodiment of the platforms of the invention contains three reservoirs plus one detection chamber for each assay. Each reservoir has dimensions of from about 0.05 mm to about 5 mm wide, from about 0.05 mm to about 20 mm long, and from about 0.05 mm to about 5 mm thick, and has a volumetric capacity of from about 0.1 nL to about 500 µL. Reservoirs 417, 418, and 416 are designed to contain fluids $A_i$ (in some embodiments, this will the a sample), B, and C. For the purposes of this invention, reservoir such as reservoir 418 that is fluidly connected to the reagent manifold is terms an "aliquotted reagent reservoir". The detection cuvette for this assay is detection chamber 420 with air-port 213 leading to air displacement hole 214. Air displacement holes 214 that allow air displaced by the motion of fluids to escape, have a cross-sectional dimension of from about 100 to about 500 µm. These holes may optionally be replaced by a manifold or series of channels connecting the receiving reservoirs to one or more air holes. The detecting reservoirs are designed to be accessible to optical interrogation, for example, by being composed of optically-transparent plastics or other materials. Also shown is the distribution manifold 409 that communicates with the filling channel 415. Filling channel 415 terminates at aliquotted reagent reservoir 418. At the proximal portion of 415 a narrow passageway 414 is connected to filling channel 415. Passageway 414 passes through one or more capillary junctions 413 to air port 212. Reservoir 416 is connected via passageway 419 and via 211 to the distribution manifold 210 on the upper surface of the disc. Finally, reservoir 417 is connected via sample input port 204 to the interface This collection of reservoirs and structures—416, 417, 418, 420, 415, 414, 413, 212, 416, 419, 211, 417, and 411—is repeated on the illustrated platform of the invention a total of 96 times azimuthally around the disc with an angular spacing of about 3.5°. The 96 arrays are sub-divided into two groups of 48; which are placed with azimuthal symmetry around the disc. Platforms having a smaller or greater number of arrays of such reservoirs are within the scope of the invention being most preferably evenly spaced around the surface area of the platform in configurations that match the pattern of microfluidics components on the microfluidics layer.

Microfluidics Layer

The microfluidics layer of the embodiment of the platform of the invention is shown in FIGS. 5a through 5d.

Microfluidics layer 500 is optimally of the same lateral dimensions as the reservoir layer. There is also an optional center hole for mounting on a spindle, although this is not required in all configurations.

The microfluidics layer contains an array 501 of microfluidic structures 502, the number of structures in the array being equal to the number of parallel assays to be run on the platform. In the embodiment illustrated in the Figures, there are 96 such structures evenly repeated with angular spacing of about 3.5°. Microfluidics structures 502 preferably comprise microchannels having cross-sectional dimensions of from about 5 µm to about 500 µm and a depth in the microfluidics layer of from about 10 µm to about 3 mm.

Figure 5A:
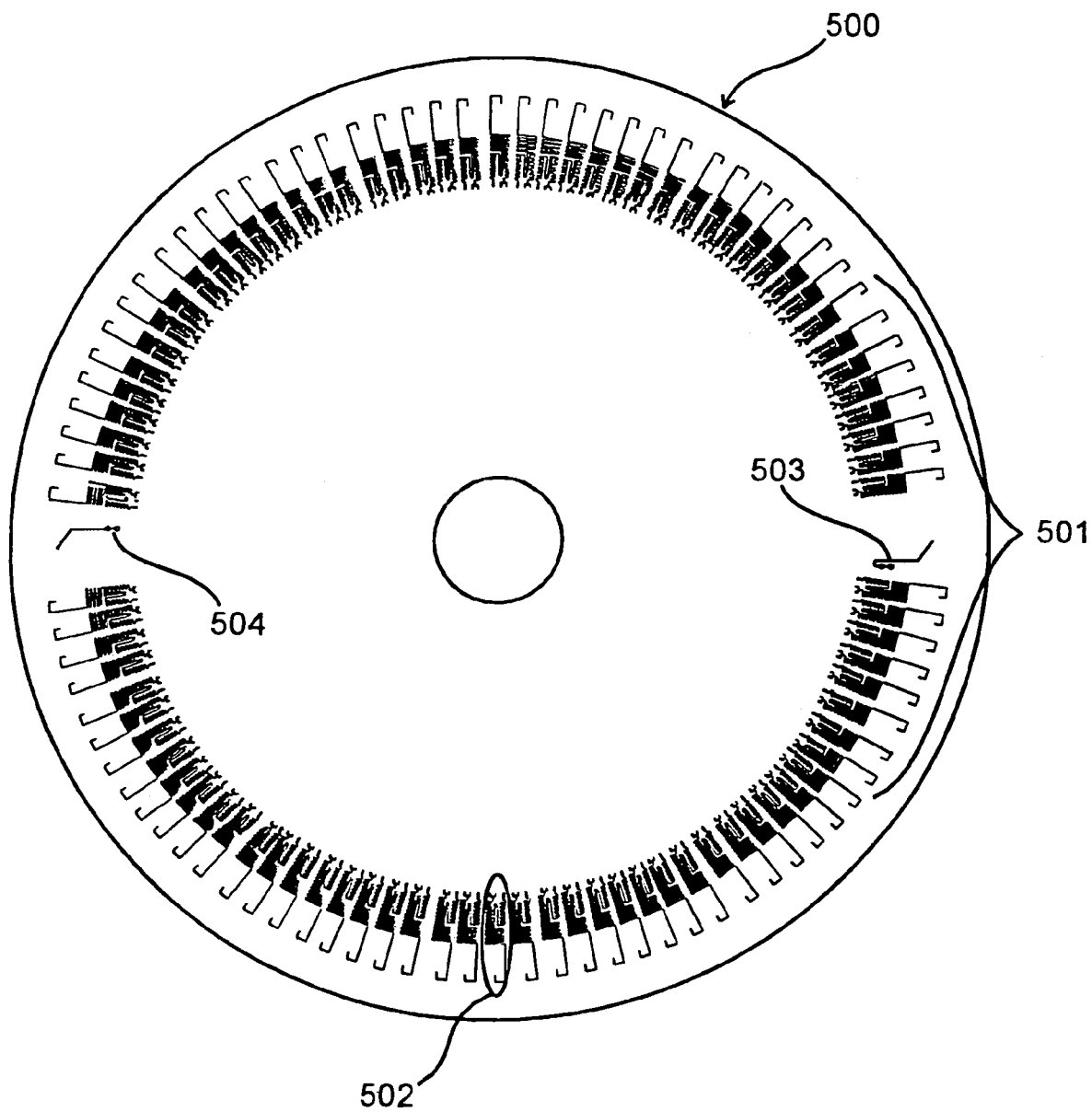
FIG. 5a depicts a plan view of another component of the microsystems platform of FIG. 1, the microfluidic layer.
Figure 5B:
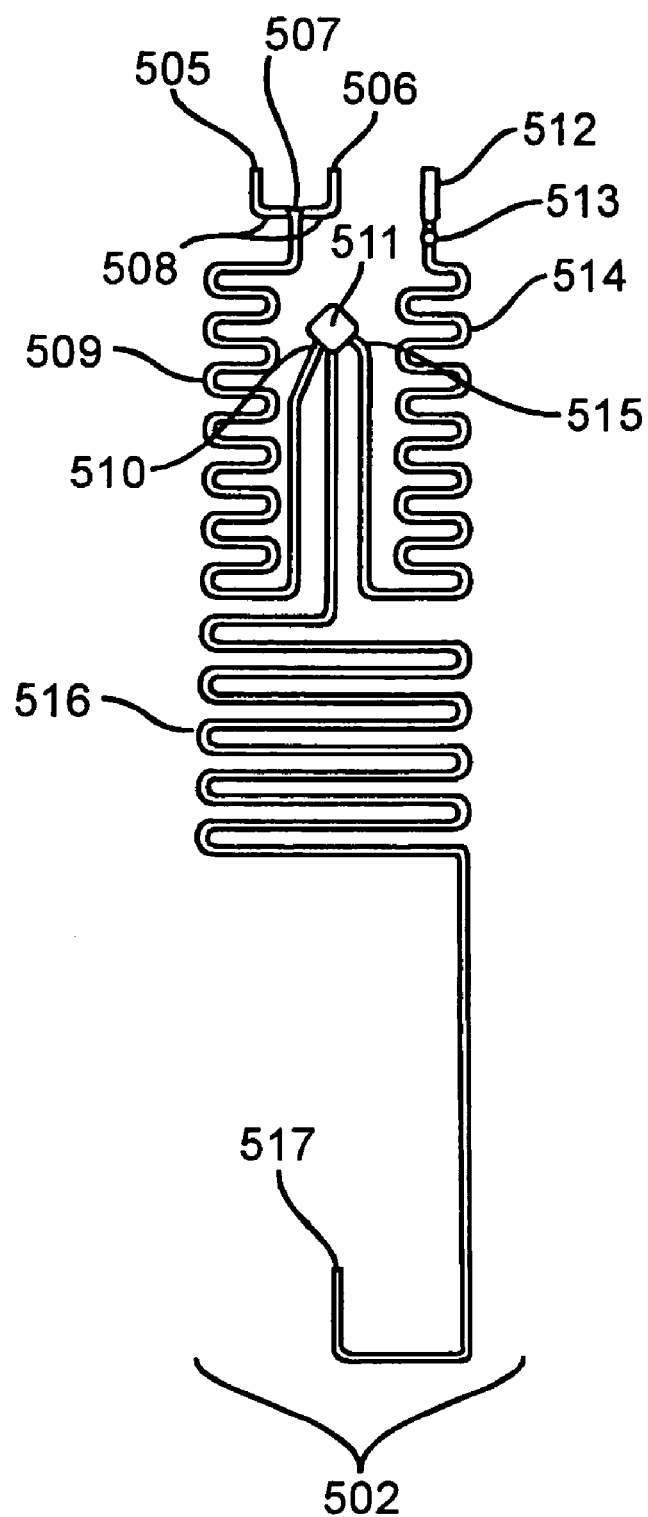
FIG. 5b is a detail of one segment of the microfluidic layer of FIG. 5 comprising the microfluidic channels of a single microfluidic assay structure.

FIG. 5b is an expanded view of a single unit of microfluidic structures. Each microfluidics structure comprises one microfluidics assay. The microfluidic structure consists of depressions in the surface of the microfluidic disc of a single or multiple depths ranging between 2 microns and 1000 microns, while the widths of the depressions varies from about 2 µm to about 500 µm, as further described below.

The structure of the microfluidics components of the assay structure are as follows. Microchannels 505 and 506 are aligned by assembly between the reservoir layer and microfluidics layer so that the microchannels protrude into reservoirs 416 and 417, respectively. Microchannels 505 and 506 in some embodiments narrow to form capillary junctions 508 before joining mixing microchannel 509. Mixing microchannels are configured to provide mixing of different solutions as the mixture traverses the longitudinal extent of the microchannel. The degree of mixing is dependent on the flow rate of the fluids and the longitudinal extent of the mixing microchannel, which is proportional to the amount of time the two fluids are in contact and are mixed together. The degree of mixing is also dependent on the lateral extent of the mixing microchannel, and is further dependent on the diffusion constants of the fluids to be mixed. In order to accommodate mixing microchannels having sufficient lengths for mixing fluids having a useful range of viscosities, the mixing microchannels are provided as shown in FIG. 5b, wherein mixing is promoted as illustrated in FIG. 5b by configuring the microchannel to bend several times as it traverses a path on the platform surface that is perpendicular to the direction of rotation, but extends radially on the surface of the platform from a position more proximal to a position more distal to the axis of rotation. Mixing microchannel 509 has a length of from about 1 mm to about 100 mm, its length in some cases achieved through the use of bends. Mixing microchannel 509 is provided with a capillary junction of a restriction in the lateral dimension at 510 wherein the interior diameter of the microchannel is reduced by about 0 to 95%, and then joins capillary junction 511. Capillary junction 511 is larger in the lateral or vertical direction or both than the restriction 510.

Mixing in the device is promoted through diffusion. If two small volumes A and B are added to a single container, diffusion of A into B and/or B into A will effect mixing. The amount of time required for this mixing will depend upon the diffusion constants of the molecules within the solutions whose mixing is desired and the distances over which the molecules must diffuse. For example, 0.5 microliter of solution A comprising a molecule with diffusion constant D is added to a reservoir 1 mm on a side. Solution B comprising a molecule whose diffusion constant is also D is added. The solutions will initially occupy the volume with an interface partitioning them. Even if the fluids are highly miscible, the diffusion times to create a completely homogeneous solution will be approximately $t=2x^2/D$. For $x=0.05$ cm (0.5 mm) and $D=10^{-5}$ cm$^2$/s, the mixing time is 500 seconds, an unacceptably long time for most reactions. This mixing time may be reduced by mechanical stirring, for example, but stirring is difficult to obtain in fluids confined in small structures because the flow of the fluid is laminar and does not contain turbulent eddies that are known to promote mixing. If, instead of placing fluids A and then B in a 1 mm$^3$ container, fluids A and B were placed side-by-side in a long, thin capillary of lateral dimension d, the relevant time for mixing is much shorter. If, for example, d is 100 microns, mixing time t is 20 seconds. The mixing channels of the device simulate the placement of fluid in a long capillary by co-injecting fluid streams A and B into a capillary microchannel. These fluids flow side-by-side down the channel initially. As the fluid is pushed through the microchannel due to centrifugal force produced by rotation of the platform, diffusion occurs between the fluids. By choosing a capillary of sufficiently narrow diameter, sufficient length, and a pumping rate that is sufficiently low, the portion of A and B of the total volumes of A and B present in the channel during pumping can be caused to mix.

These choices may be determined by setting the required time for mixing equal to the amount of time necessary for the fluid to traverse the channel. The required time for diffusion is $$t_m \approx \frac{2w^2}{D}$$

where w is the lateral size of the channel. The amount of time necessary to traverse the channel is simply the length of the channel divided by the fluid velocity, the velocity being calculated as described in co-owned and co-pending U.S. Ser. No. 08/910,726, filed Aug. 12, 1997, and Duffy et al. (1999, *Anal. Chem.* 71: 4669-4678):

$$t_t = \frac{l}{U} = \frac{l}{\left(\frac{\rho\omega^2 \Delta R \langle R \rangle (d^H)^2}{32\eta l}\right)} = \frac{32\eta l^2}{\rho\omega^2 \Delta R \langle R \rangle (d^H)^2}$$

where the fluid properties are the density $\rho$ and viscosity $\eta$, $\Delta R$ and $\langle R \rangle$ are the extent along the radius and average radial position of the fluid subject to centripetal acceleration, and l and $d^H$ are the length and hydraulic diameter of the channel. By choosing variables such that $t_t$ is at least equal to or greater than $t_m$, mixing in the microchannels is achieved.

Entry 512 to microchannel 514 protrudes into aliquotted reagent reservoir 418 and preferably forms capillary junction 513, having dimensions substantially the same as capillary junction 511. Microchannel 514 passes through a restriction in the lateral dimension at 515 wherein the interior diameter of the microchannel is reduced by about 1-99%, and then joins capillary junction 511. The capillary junction leads to a further mixing microchannel 516 that terminates at end 517 and that protrudes into detection chamber 420. Mixing microchannel 516 has a length of from about 1 mm to about 100 mm.

Figure 5C:
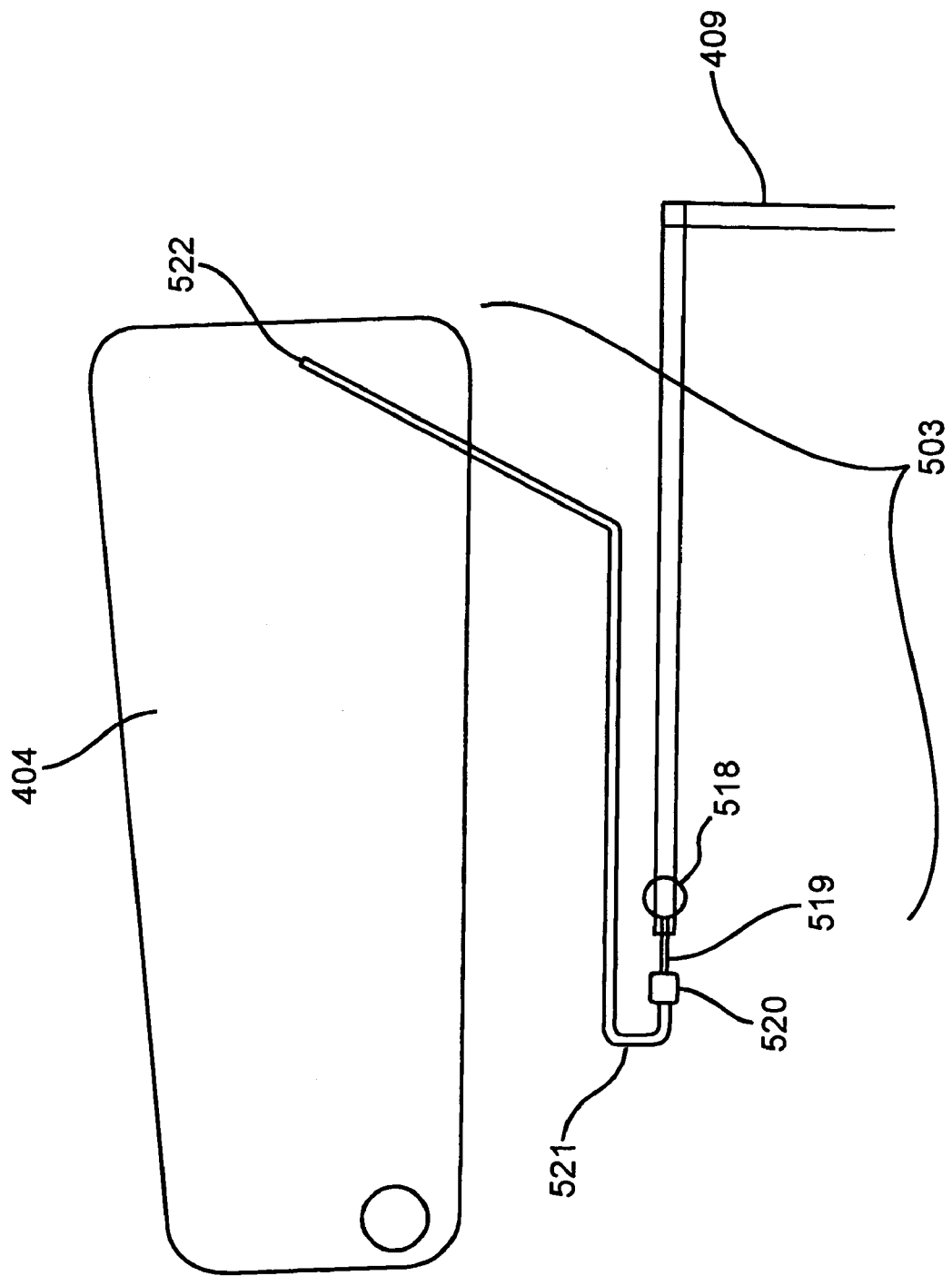
FIG. 5c is a detail of the microfluidic layer of FIG. 5 illustrating the overflow valve and channels for the first reagent.
Figure 5D:
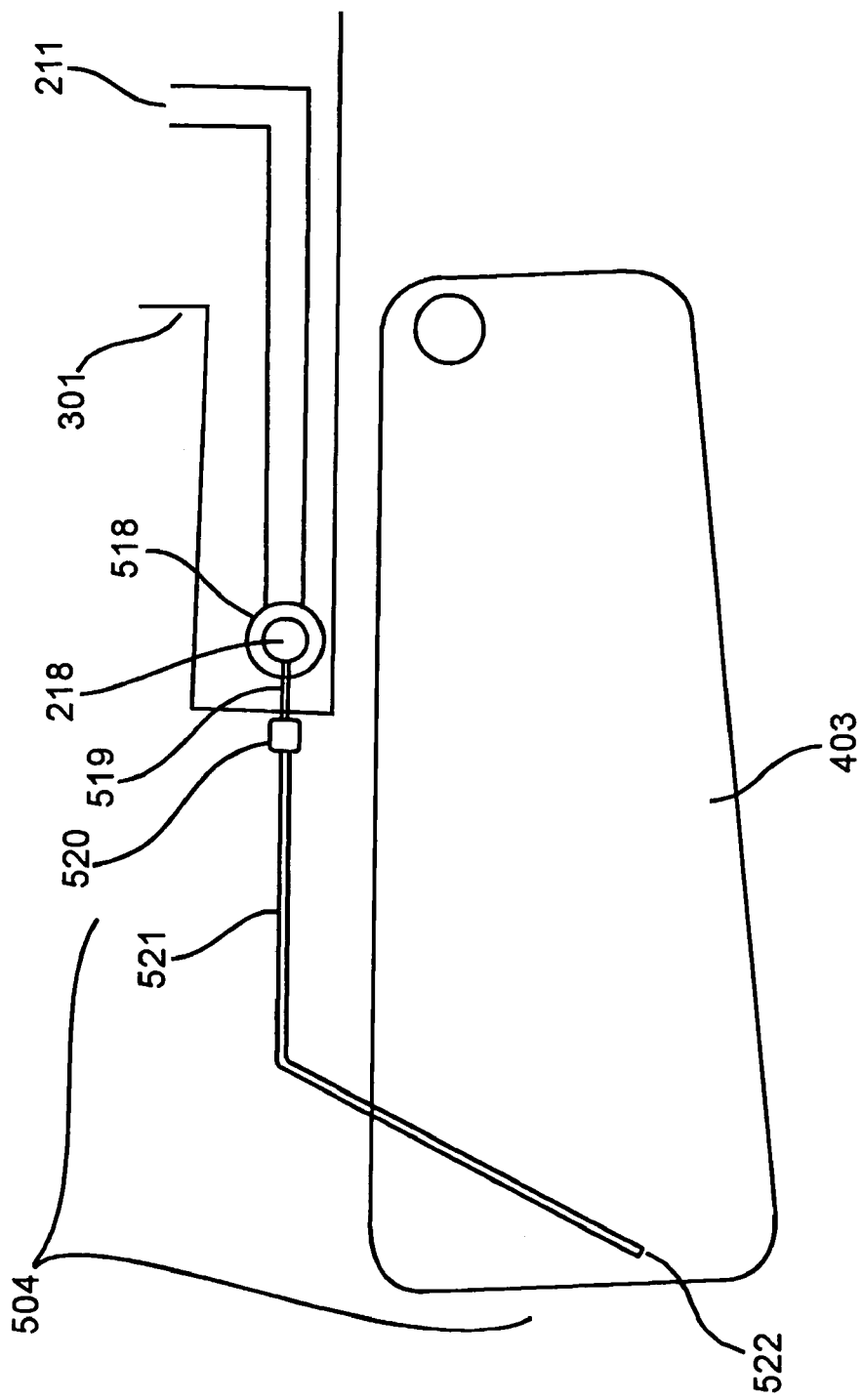
FIG. 5d is a detail of the microfluidic layer of FIG. 5 illustrating the overflow valve and channels for the second reagent.

Additional structures on the microfluidics disc include overflow reservoirs 503 and 504 as shown in FIG. 5c and 5d. Each overflow structure abuts at 518 with the terminus of a distribution manifold. Entry 518 passes through passageway 519 to enlargement 520, forming a capillary junction. This is then connected via channel 521 that ends at 522, internal to an overflow chamber.

Structure of the Assembled Microsystems Platform

Figure 6:
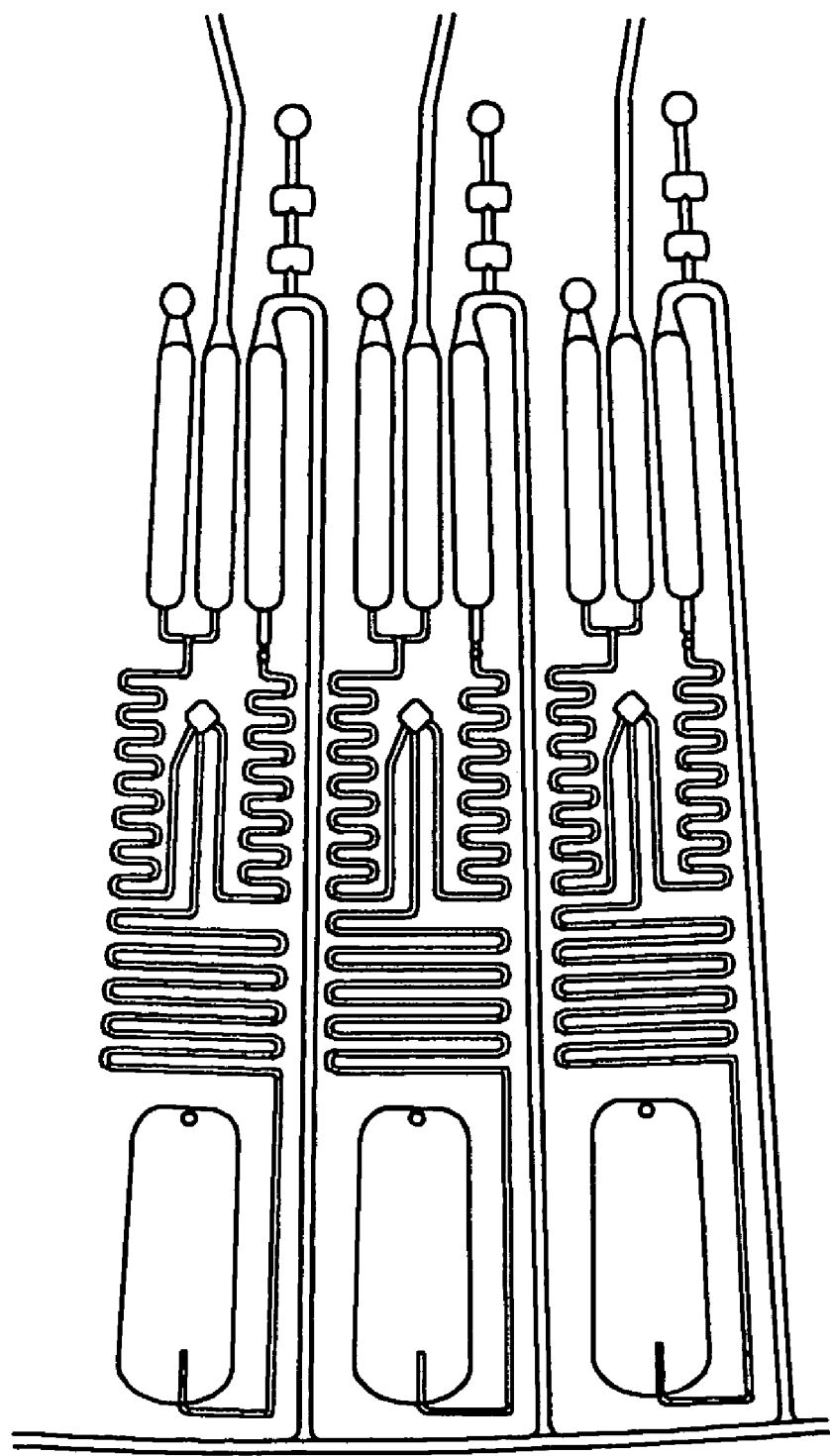
FIG. 6 is a segment of the assembled reservoir and microfluidic layers comprising the microsystems platform of FIG. 1.

FIG. 6 illustrates three assay sectors of the assembled platform, in which the reservoirs of the reservoir layer are mated to microchannels from the microfluidics layer. The platform layers are mated as described in more detail below.

Because the principles by which the fluidic elements of the platforms are combined are understood, these platforms can be used for a variety of bioanalytical methods. Passive or capillary valving of two fluids to bring them into a channel and the use of that channel to facilitate fluid mixing by diffusion may be used to include any number of fluids, and is not limited to the mixture of two fluids followed by further combination of the first mixture with a third fluid, as illustrated herein. In addition, since the mixing ratios depend on the geometric shapes of the reservoirs containing the solutions to be mixed (as described more fully in co-owned U.S. Pat. No. 6,063,589, issued May 16, 2000 and incorporated by reference herein), alternative arrangements of these geometries result in mixing ratios over a large range.

Similarly, capillary valving is understood to depend on geometry, fluid properties and rotational rate, as disclosed more fully in U.S. Ser. Nos. 08/761,063, filed Dec. 5, 1996; Ser. No. 08/768,990, filed Dec. 18, 1996; and Ser. No. 08/910, 726, filed Aug. 12, 1997, incorporated by reference herein.

Alternative arrangements of the microfluidic layers of the platforms of the invention can be provided to contain any number of concentric rings of assays consistent with the amount of surface area available on the platform surface and the extent of the surface taken up by any one embodiment of microfluidics required to perform an assay.

The fluid channels described here are preferably of a size that the residence time within the channel of a fluid element under centrifugal flow is sufficient to allow diffusional mixing across the diameter of the channel. The design of such mixing elements is defined in co-owned and co-pending application U.S. Ser. No. 09/595,239, filed Jun. 16, 2000, incorporated by reference.

An example of alternative platforms for performing assays of the general form disclosed herein, having a number of reservoirs whose volume is equal to the total fluid volume of an assay, VA, connected by microchannels to a collection/detection chamber having the same volume VA. For reservoirs having a common depth, t, and microchannels and inter-assay areas occupying approximately the same area as the reagent reservoirs and collection/detection chambers, the total number of assays possible on a disc of radius R is approximately Number of assays=$\pi R^2 t/(4VA)$ For a platform having a radius of R=6 cm, a reservoir depth of 0.1 cm and a total fluid volume of 4 microliters, the total number of assays that can be fit onto the disc is 706.

Other considerations include the placement of the components on the platform relative to the axis of rotation. Generally, the collection/detection chamber should be closer to the edge of the platform than the reagent reservoirs, so that there will be sufficient hydrodynamic pressure produced by convenient rotational speeds to motivate the fluid through the microchannels and mixing elements and into the collection/detection chambers. Placement of the collection/detection chambers at the outer edge of the platform also facilitates detection using a fixed optical detector. However, for extremely high-density platforms this may not be the most efficient way to arrange the assay components. For example, if the desired number of assays can be achieved only by placing the collection/detection chambers nearer the reservoirs containing the unreacted samples and reagents, it may be necessary to use a detector that can access cuvettes at a variety of radial and azimuthal positions. An example of a scanning optical system would be one in which the optical signal is scanned radially, while the disc could be indexed beneath the optics azimuthally. In this way the optics can address any point on the disc surface. Scanning methods include a detector on a linear drive that moves radially; alternately, the optical signal may be scanned radially through the use of a galvanometrically-controlled mirror system.

Figure 7A:
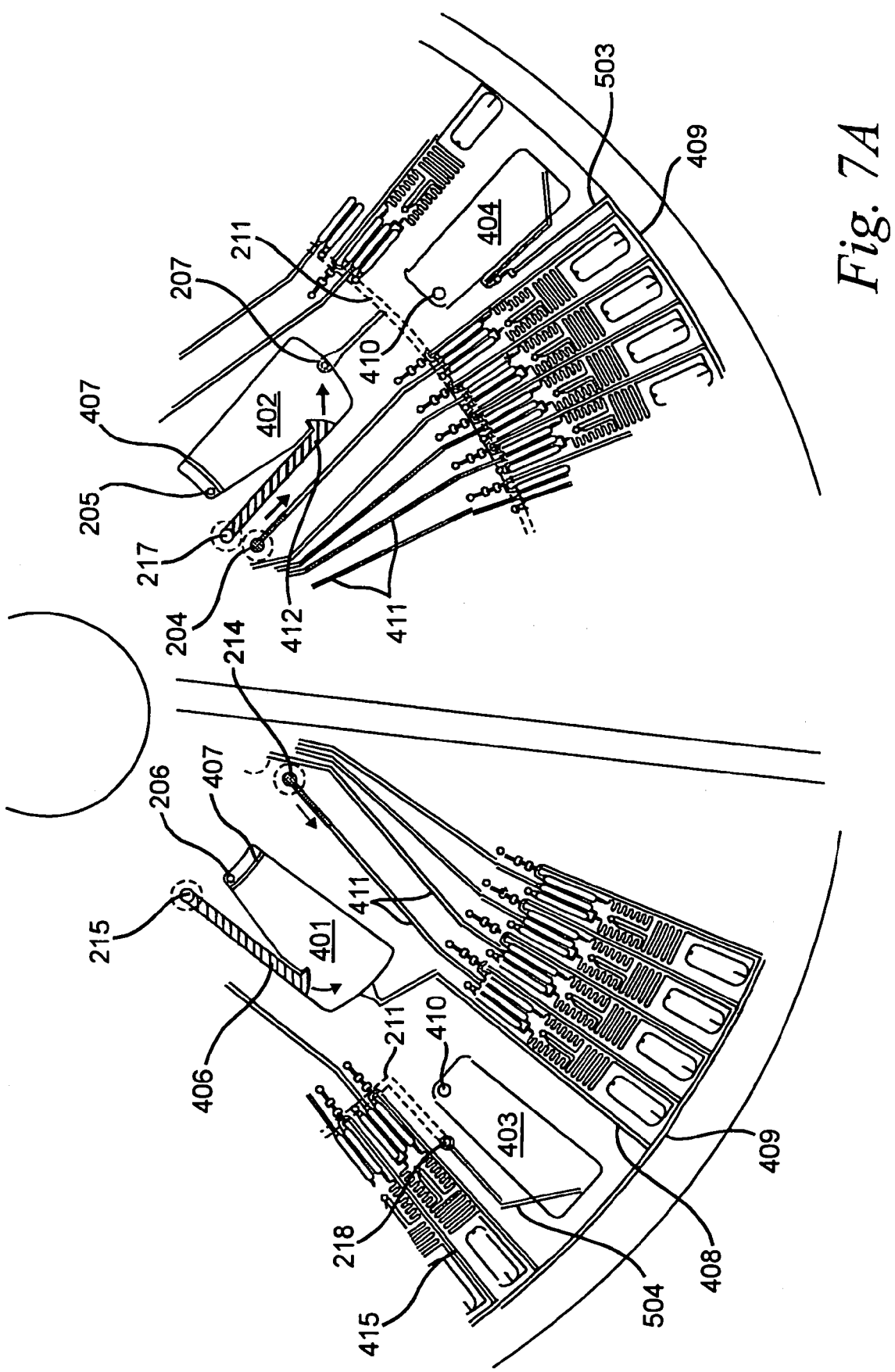
FIGS. 7a through 7g illustrate the sequence of fluid motions as sample, reagent 1, and reagent 2 are distributed to the reservoirs of the device of FIG. 1.
Figure 7B:
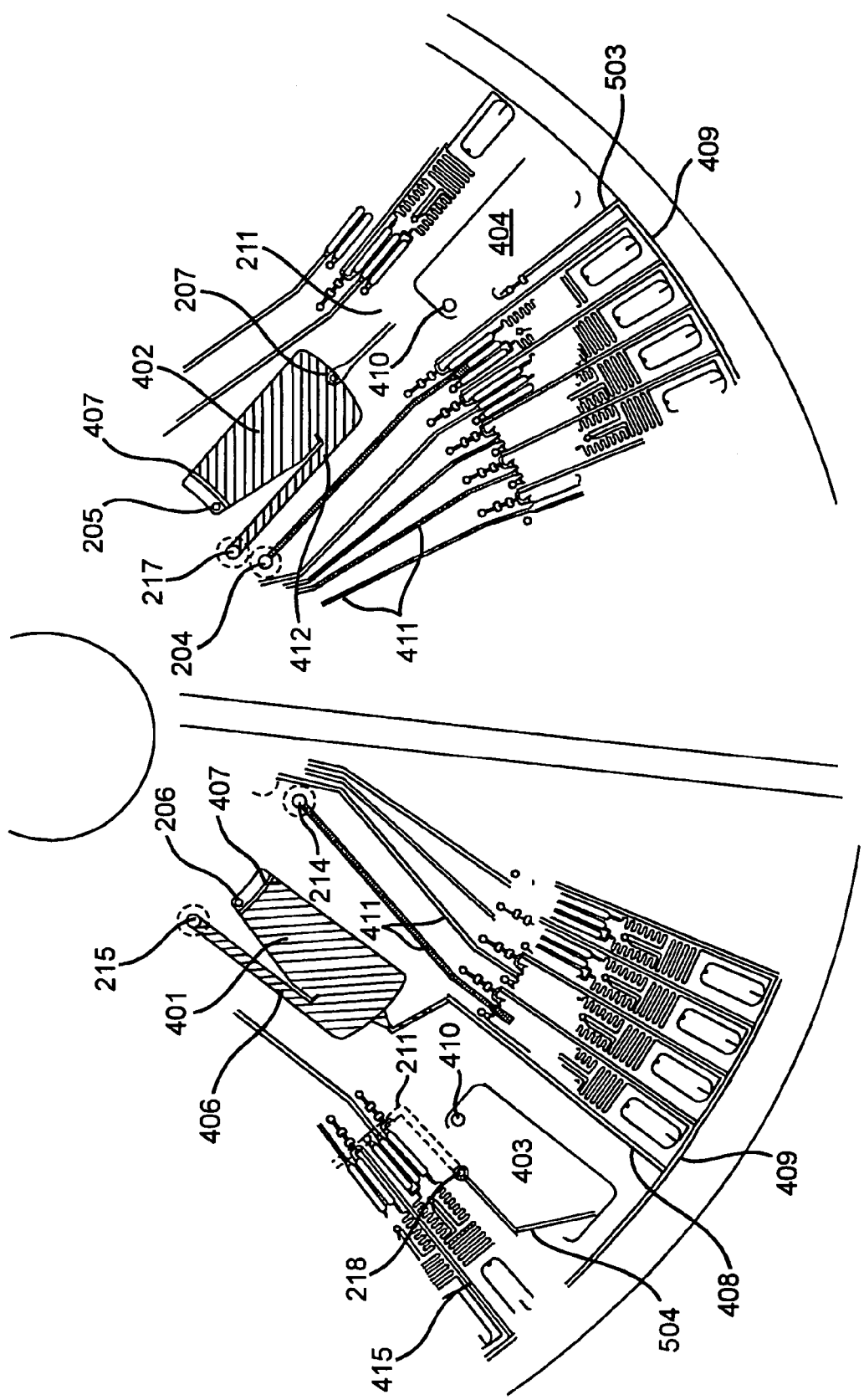
Figure 7C:
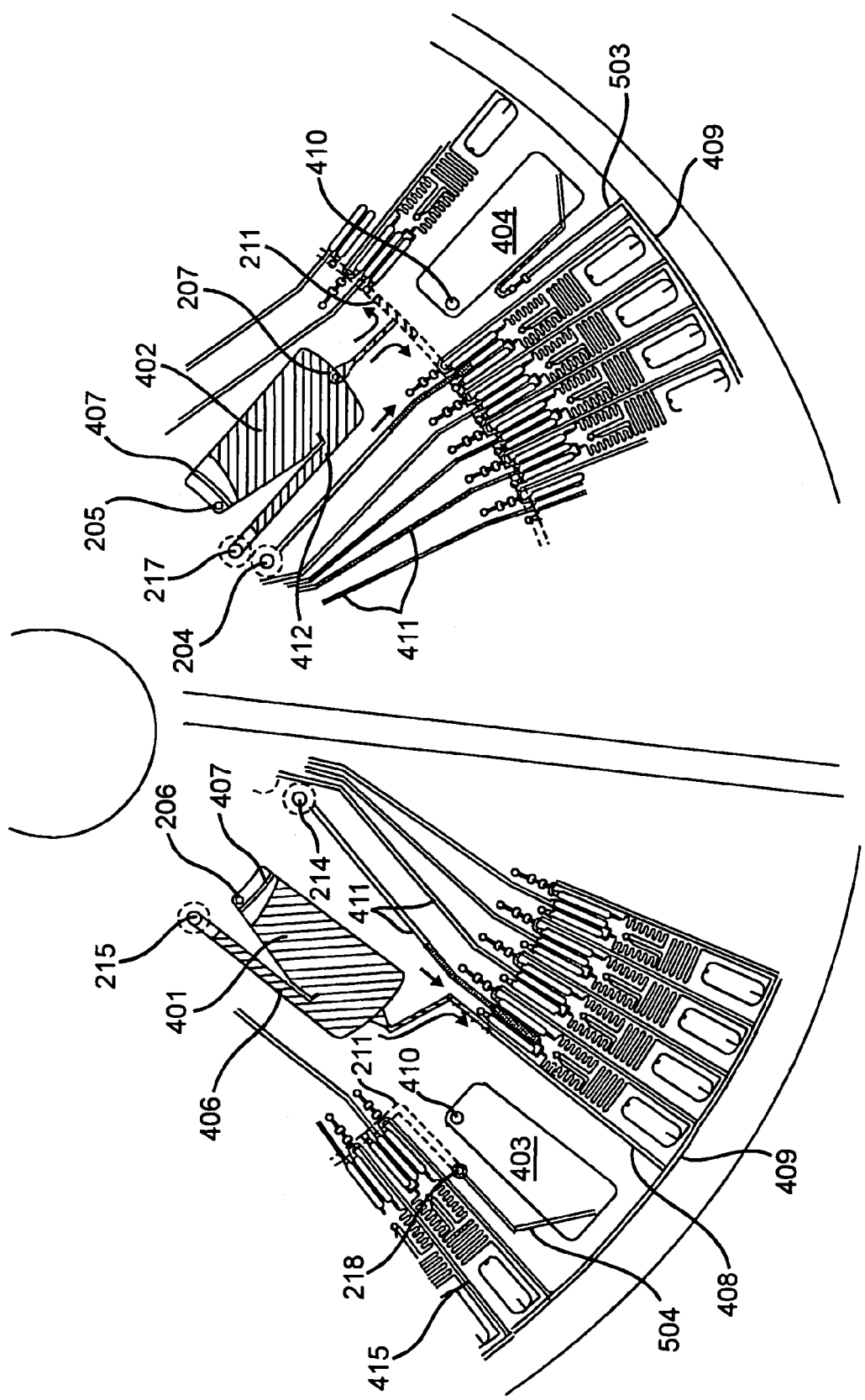
Figure 7D:
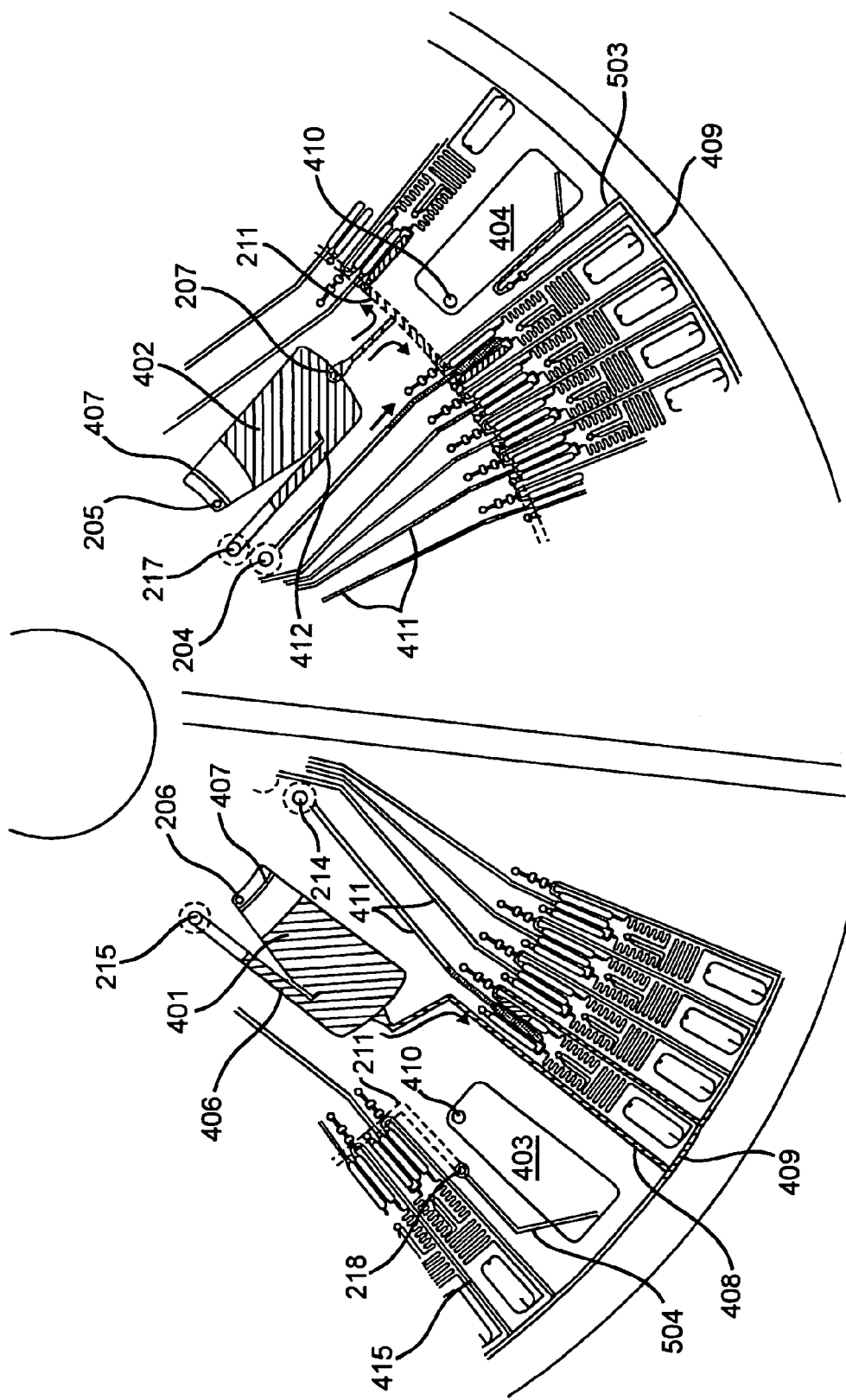
Figure 7E:
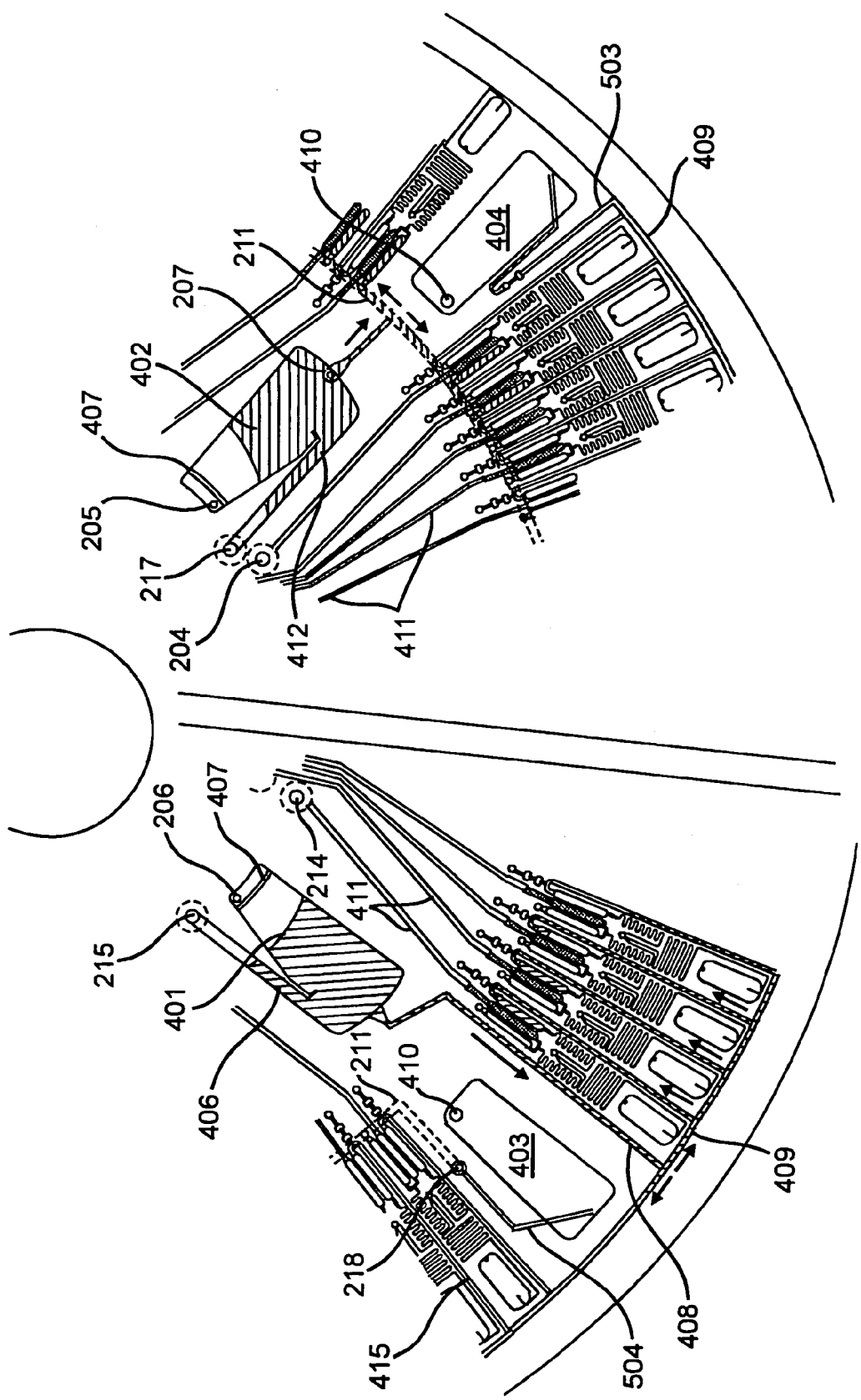
Figure 7F:
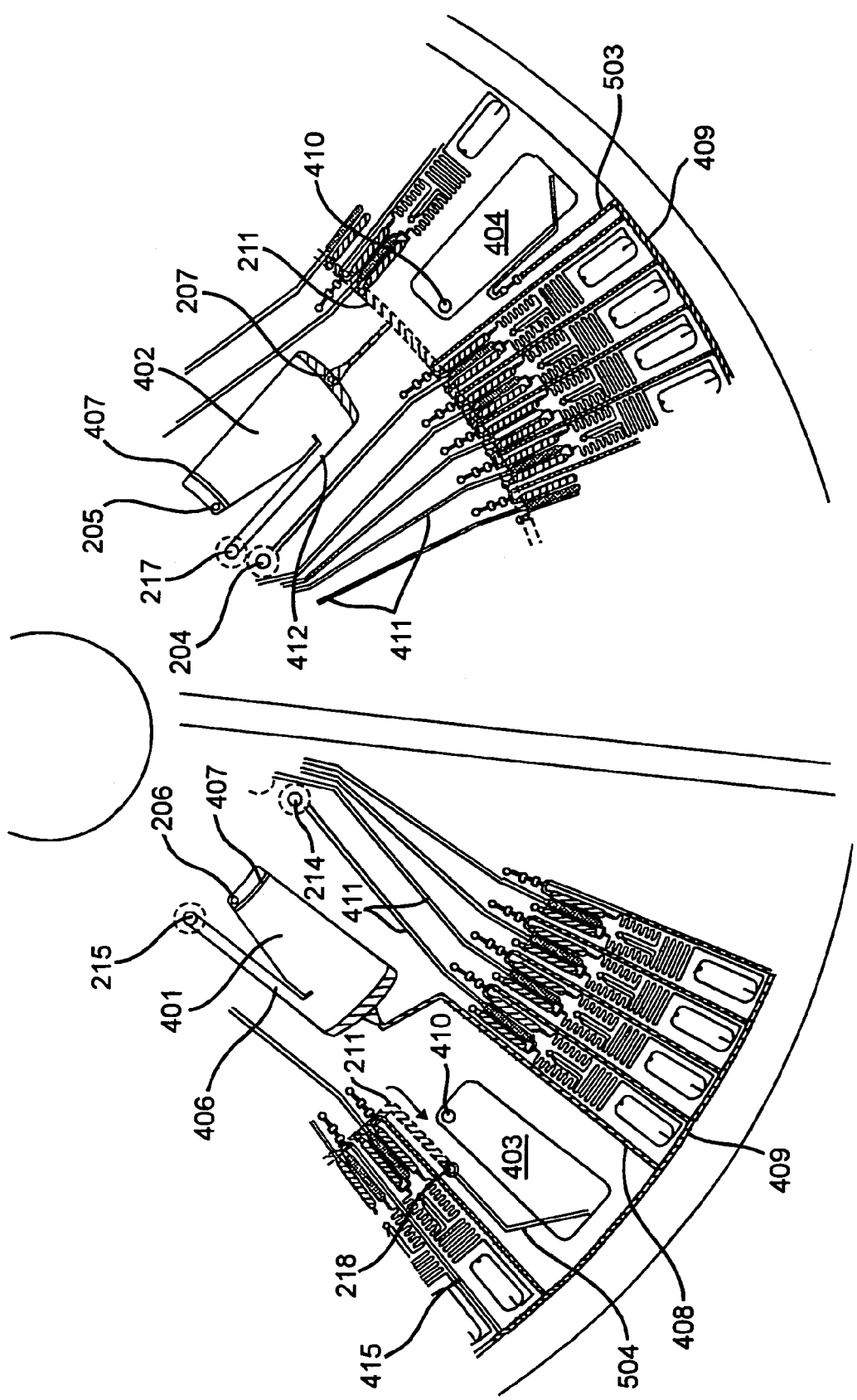
Figure 7G:
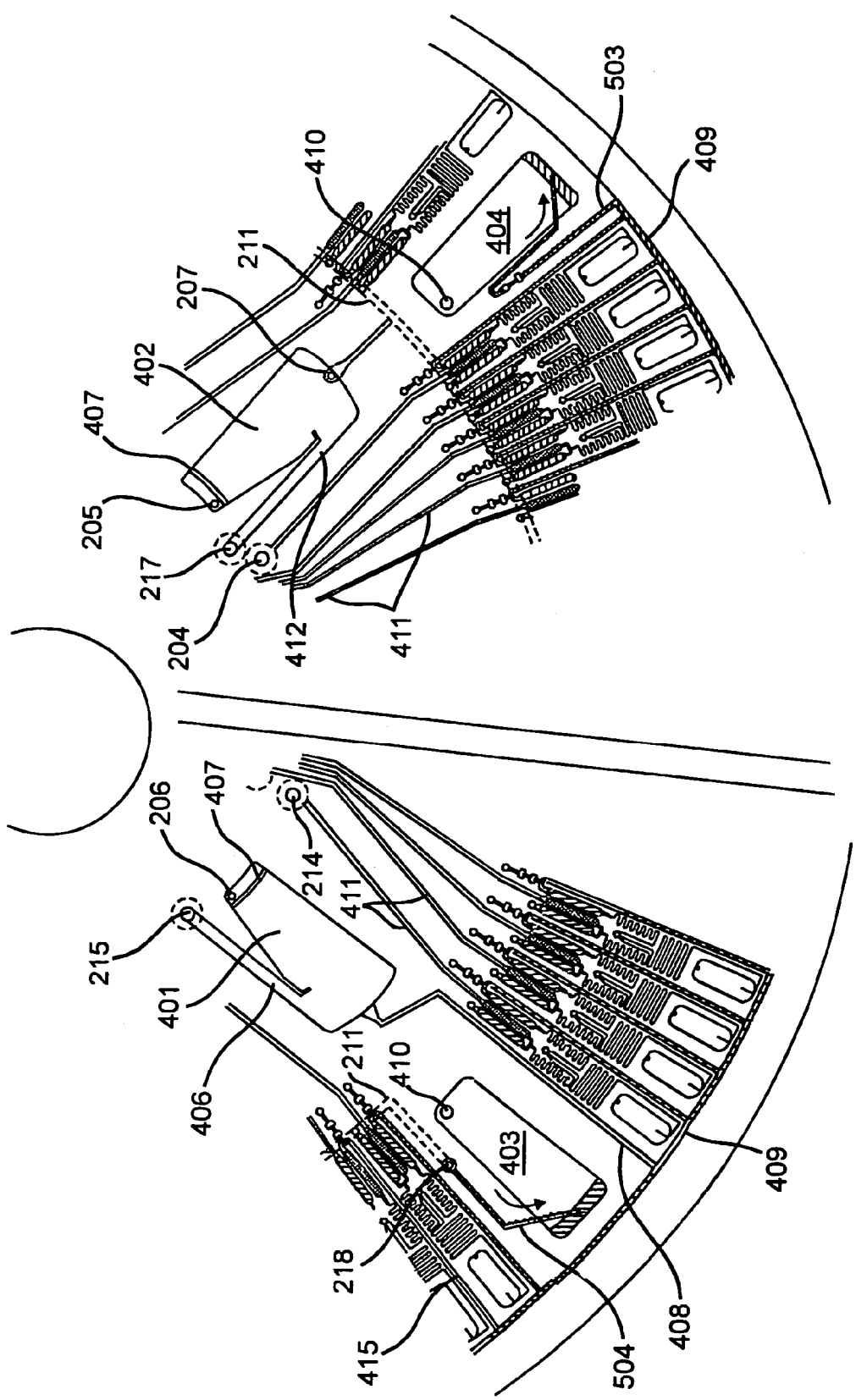
Figure 8A:
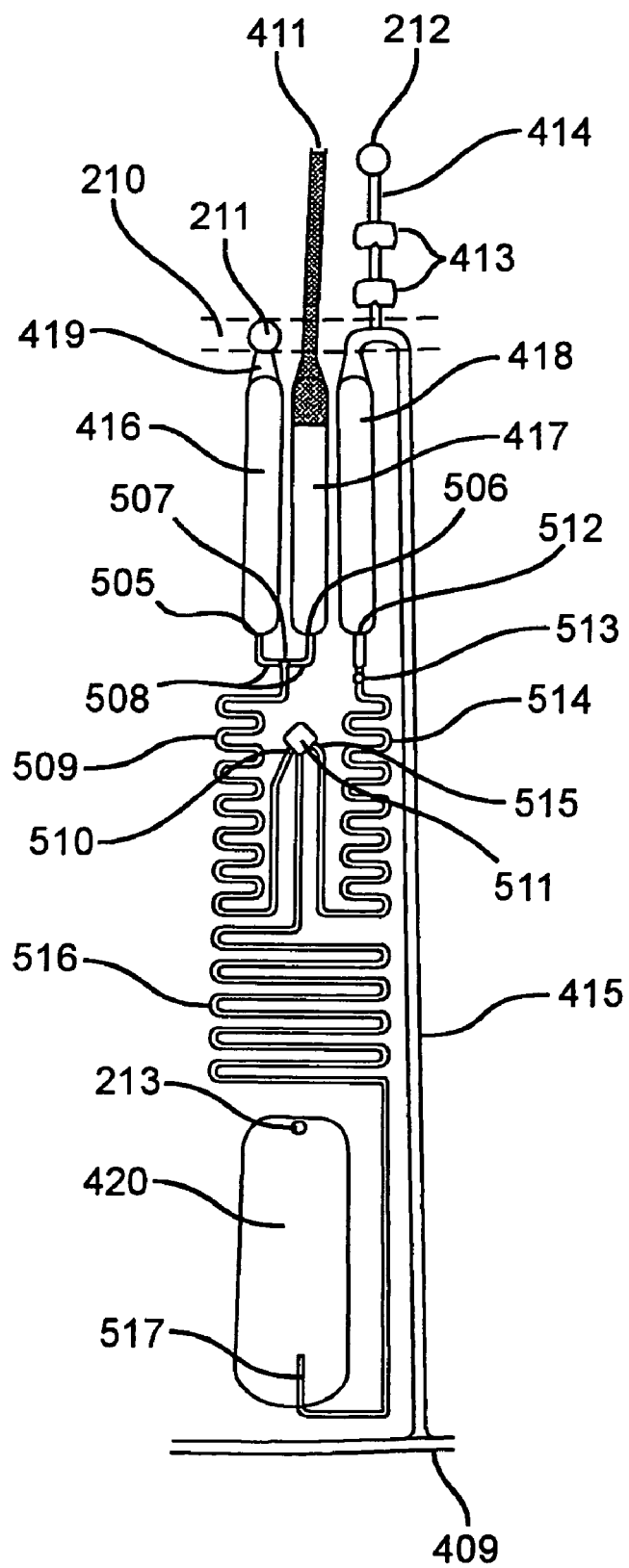
FIGS. 8a through 8l illustrate the sequence of fluid motions into a single microfluidic assay structure of the device of FIG. 1.
Figure 8B:
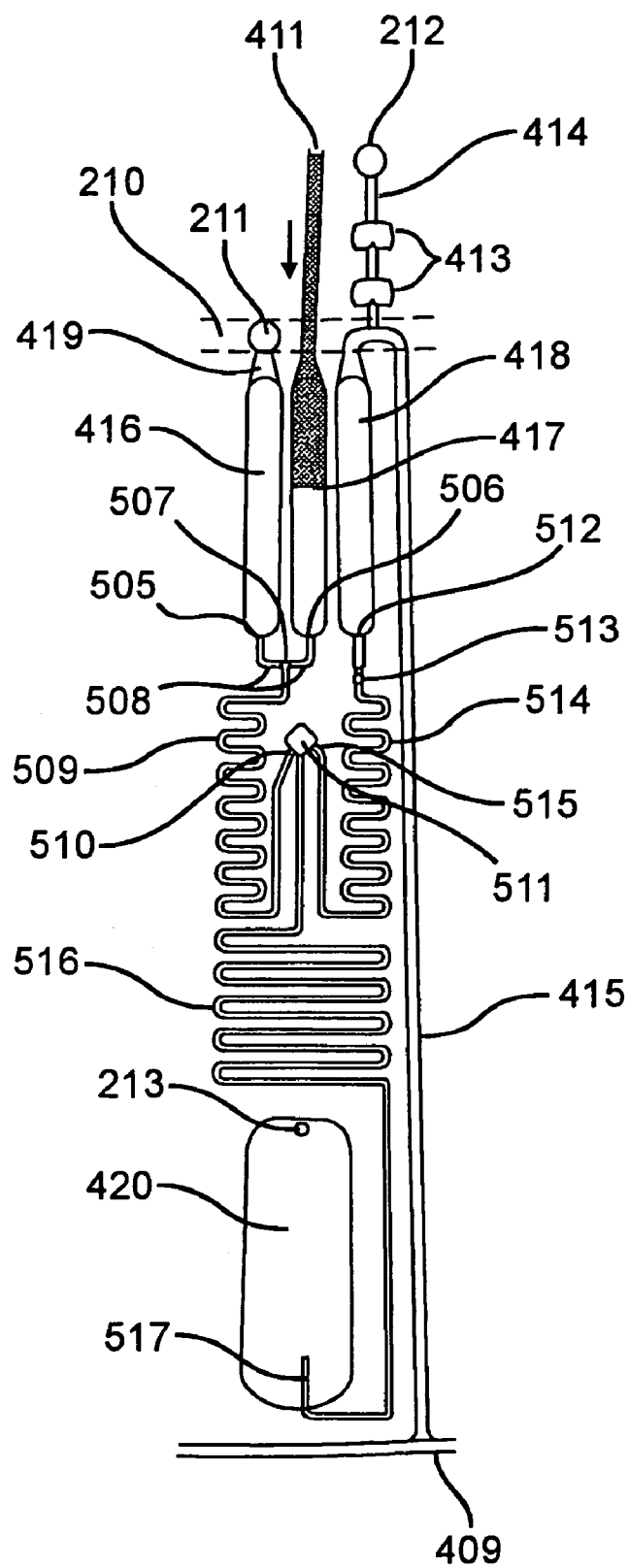
Figure 8C:
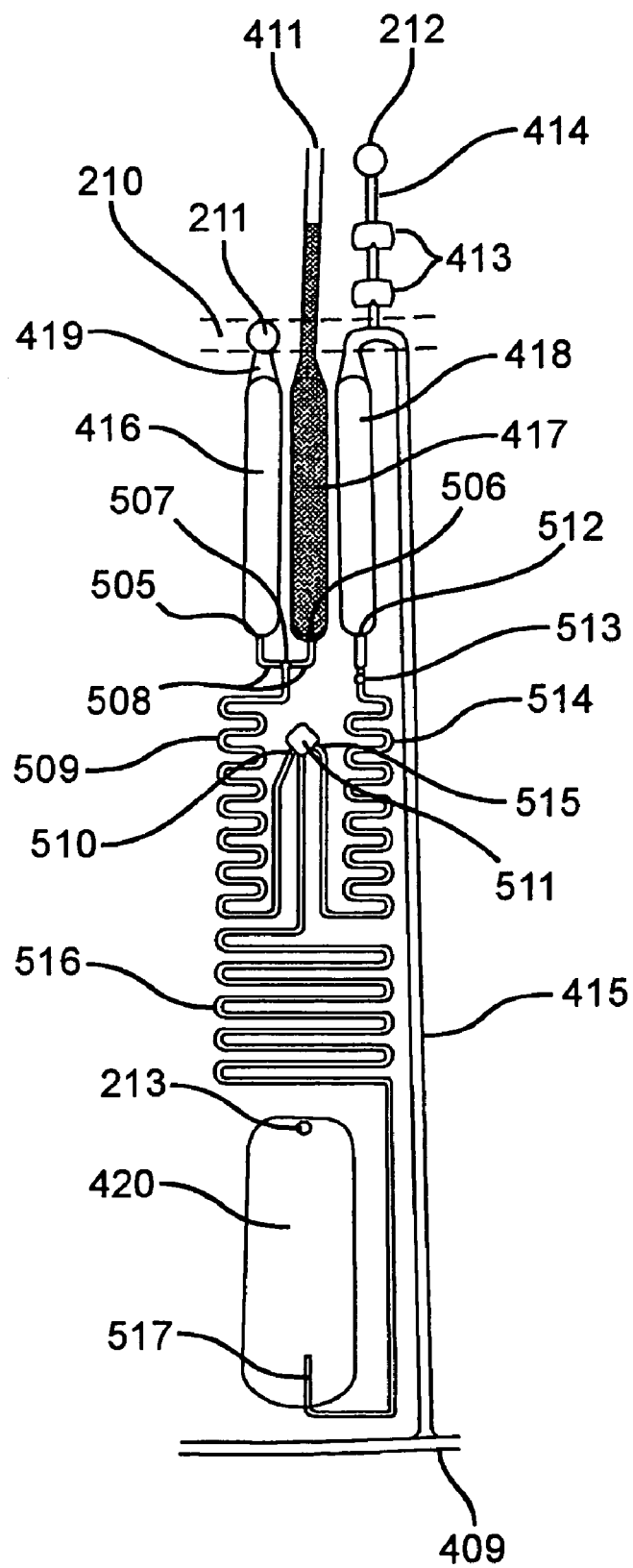
Figure 8D:
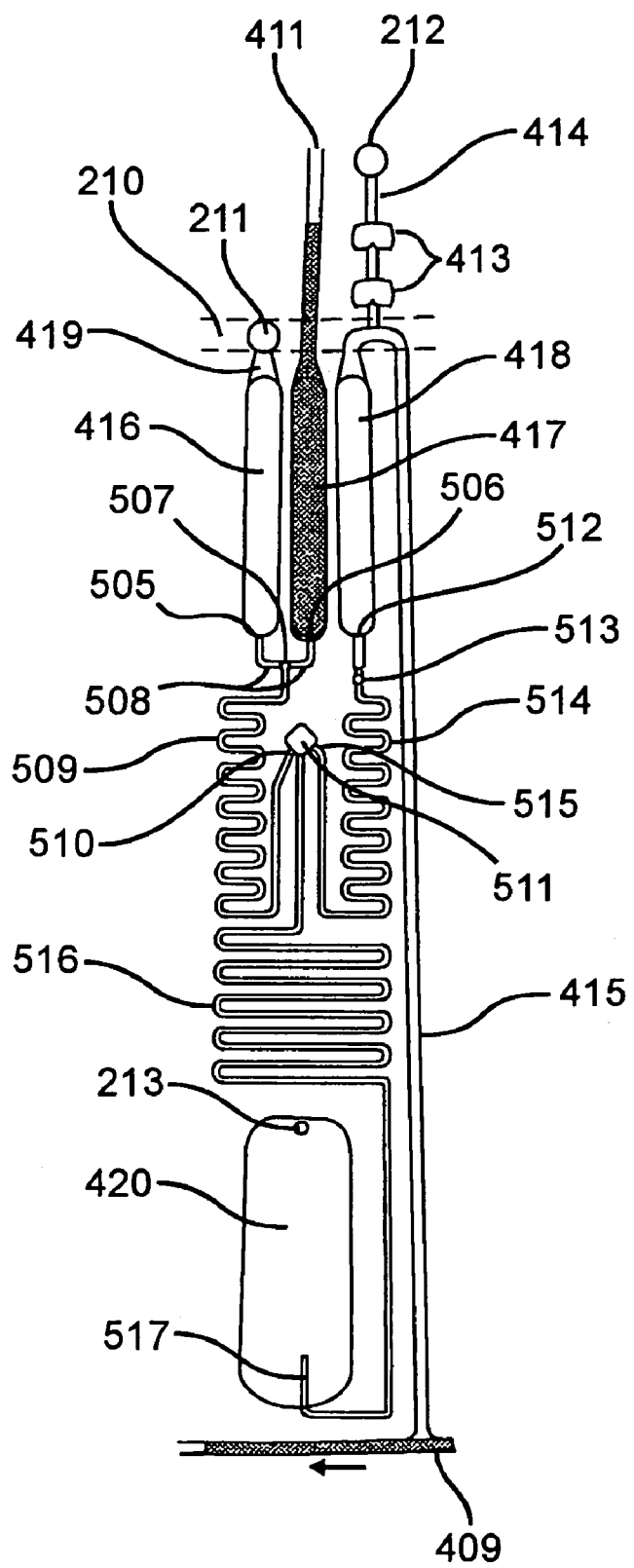
Figure 8E:
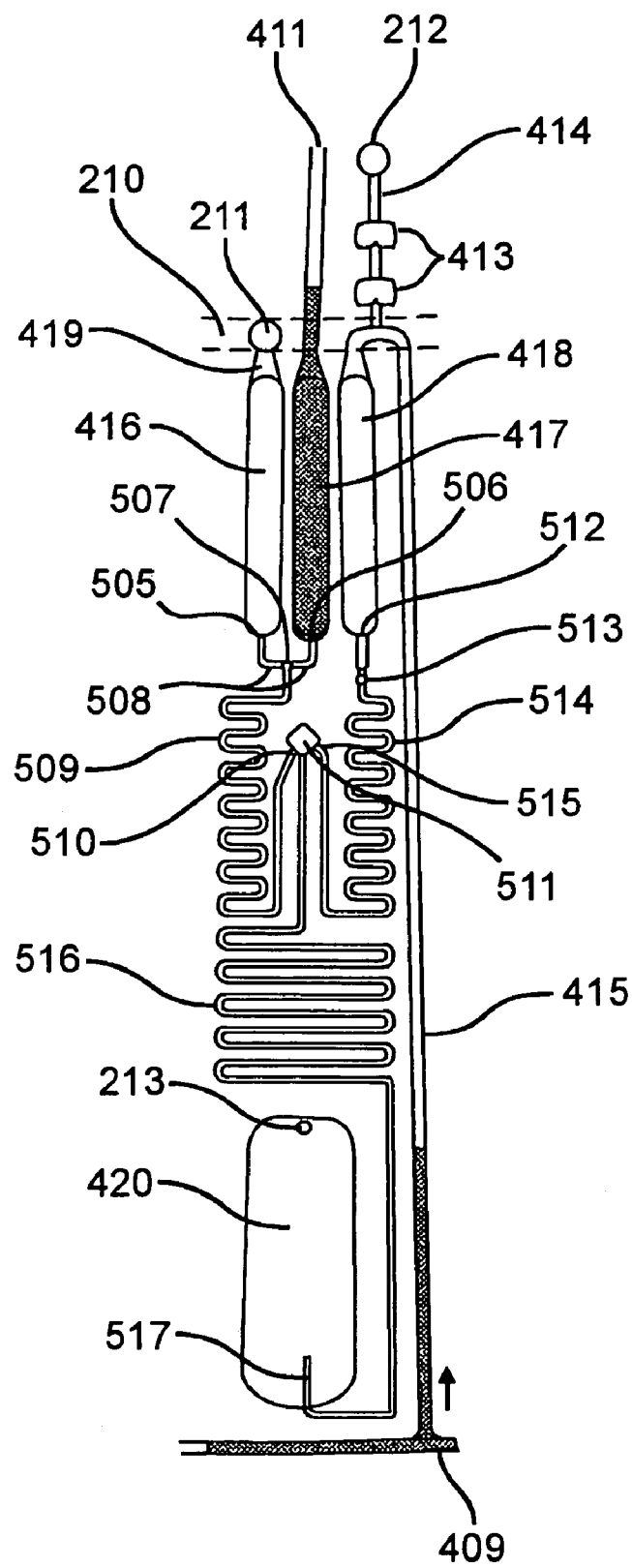
Figure 8F:
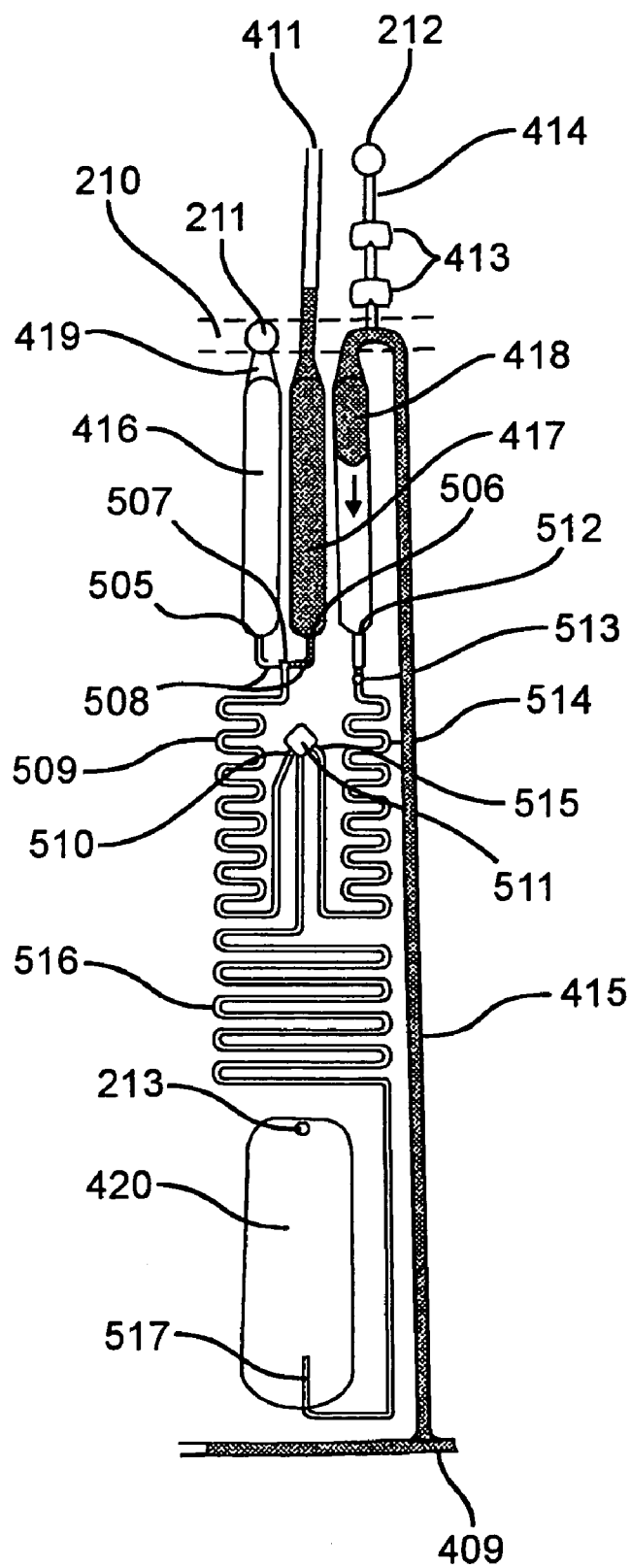
Figure 8G:
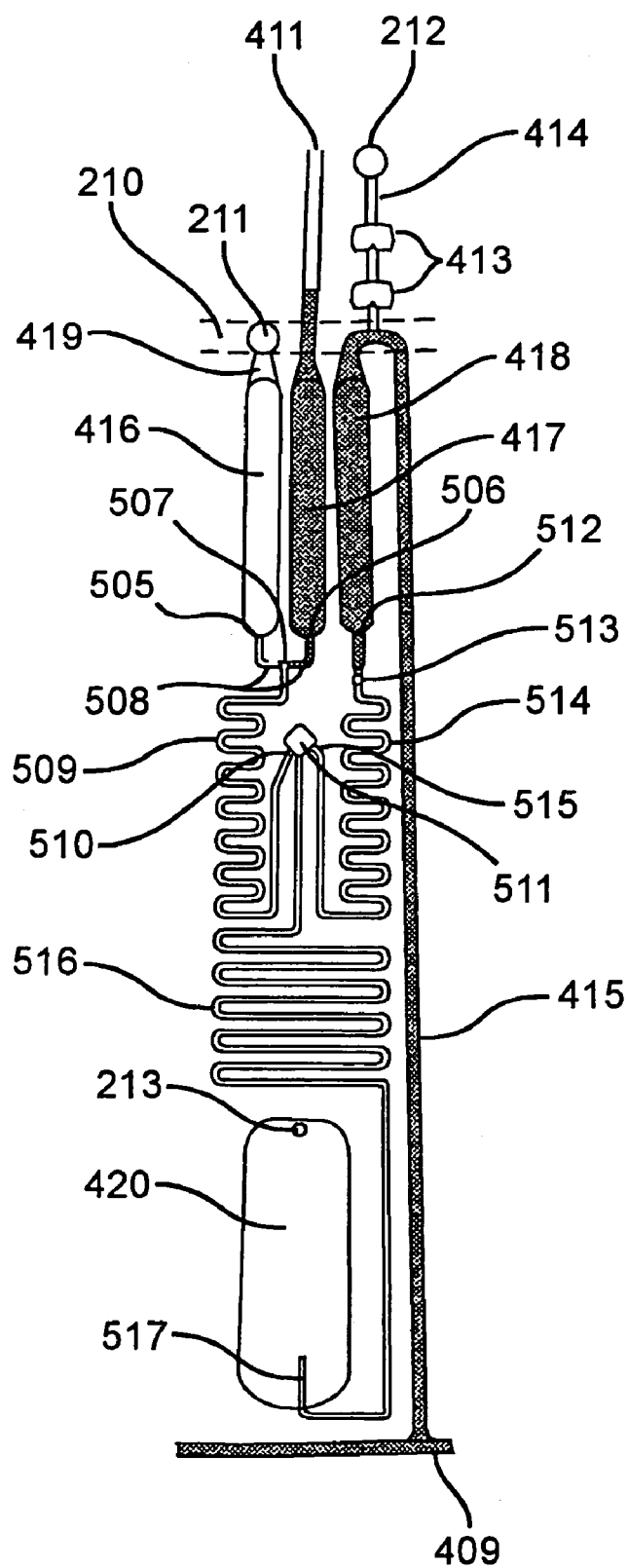
Figure 8H:
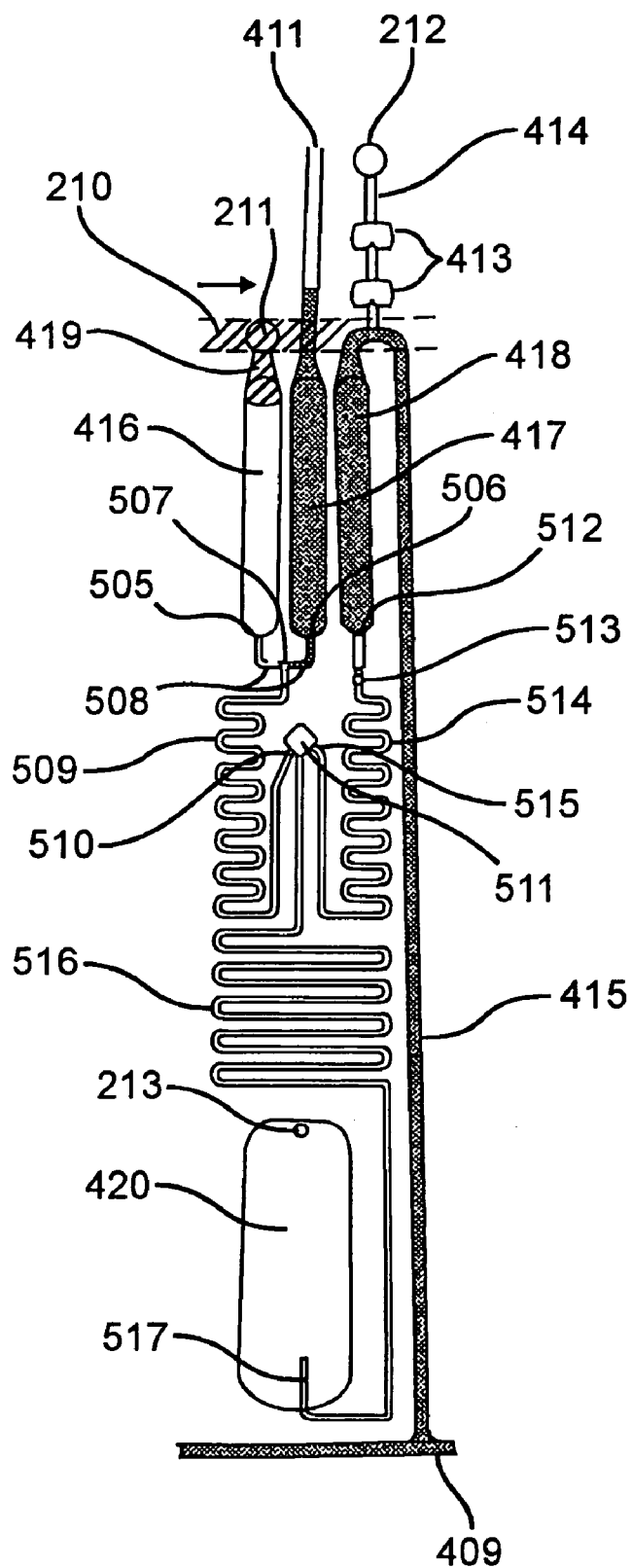
Figure 8I:
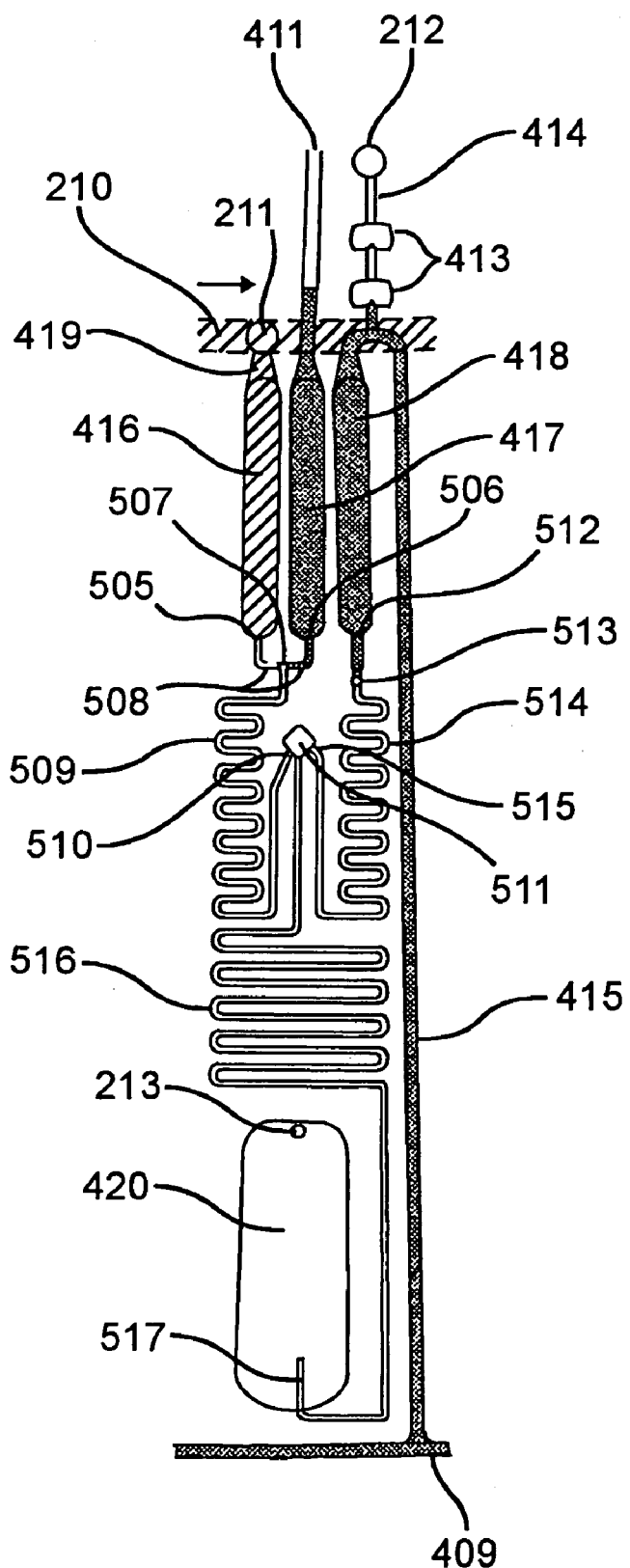
Figure 8J:
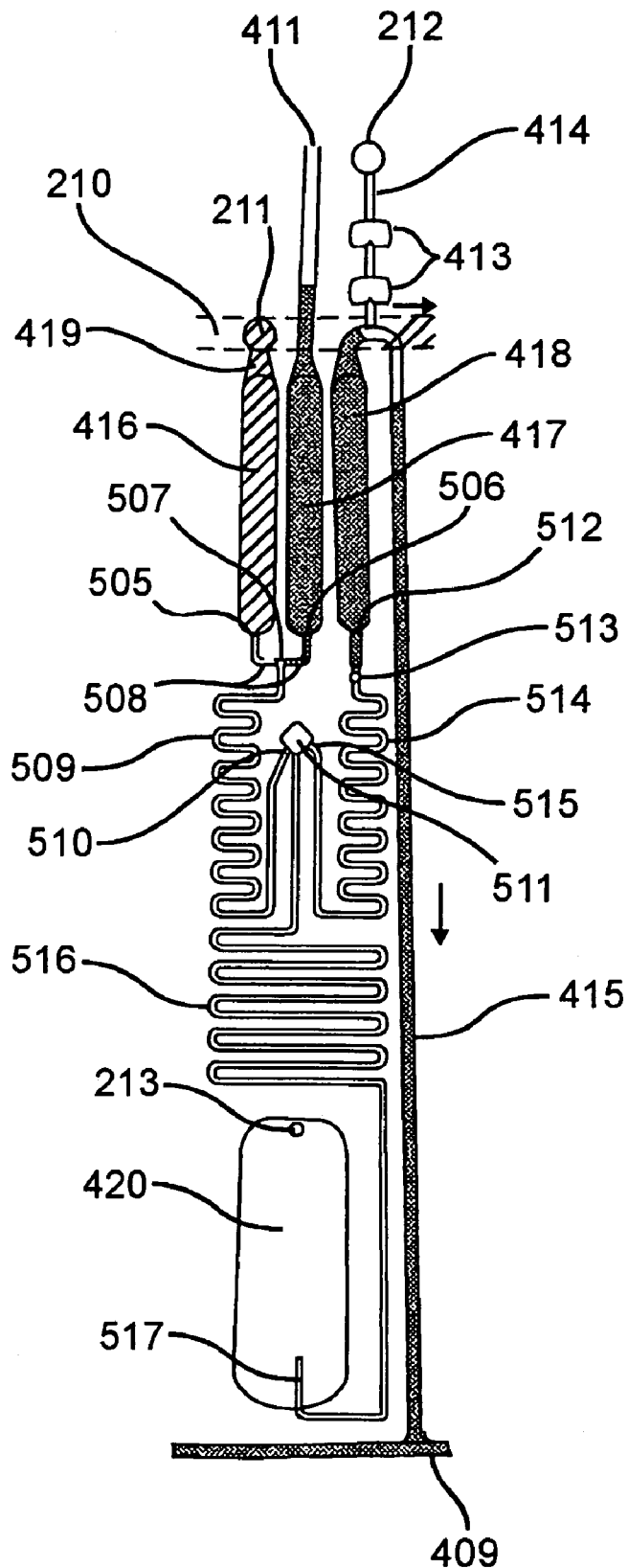
Figure 8K:
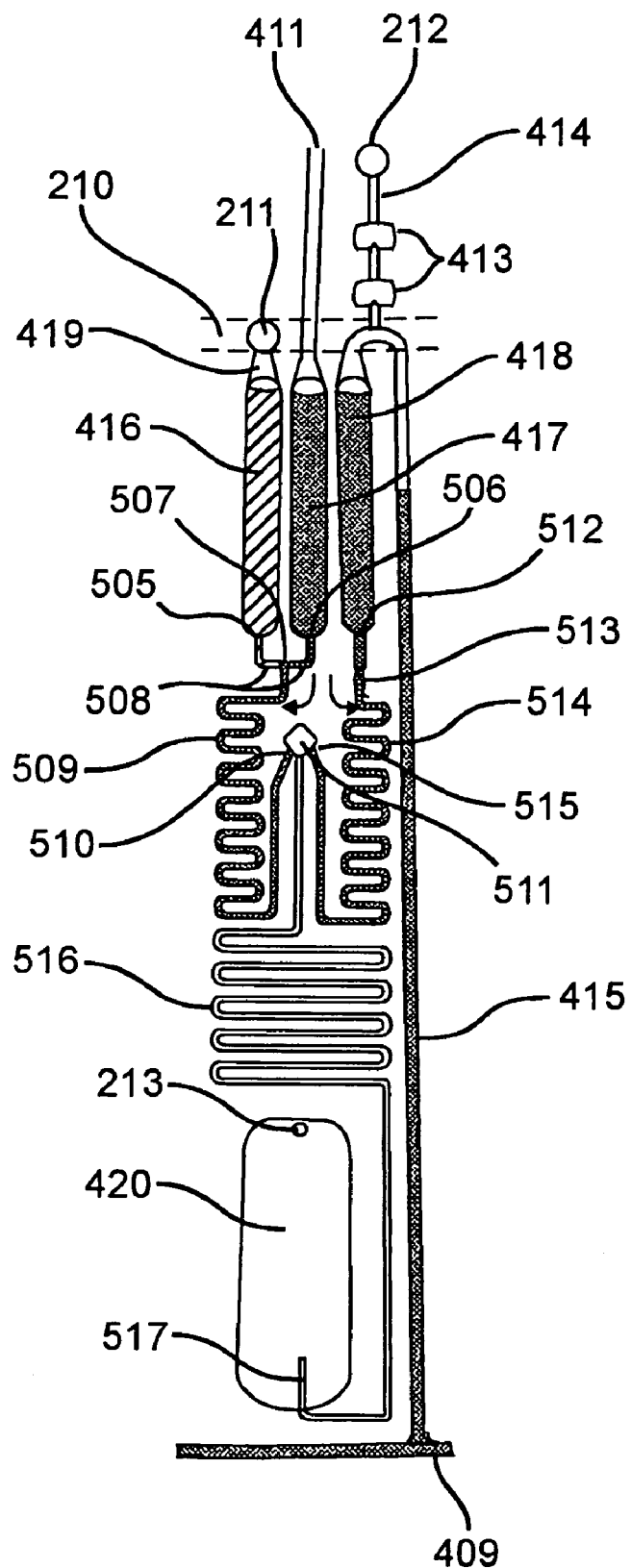
Figure 8L:
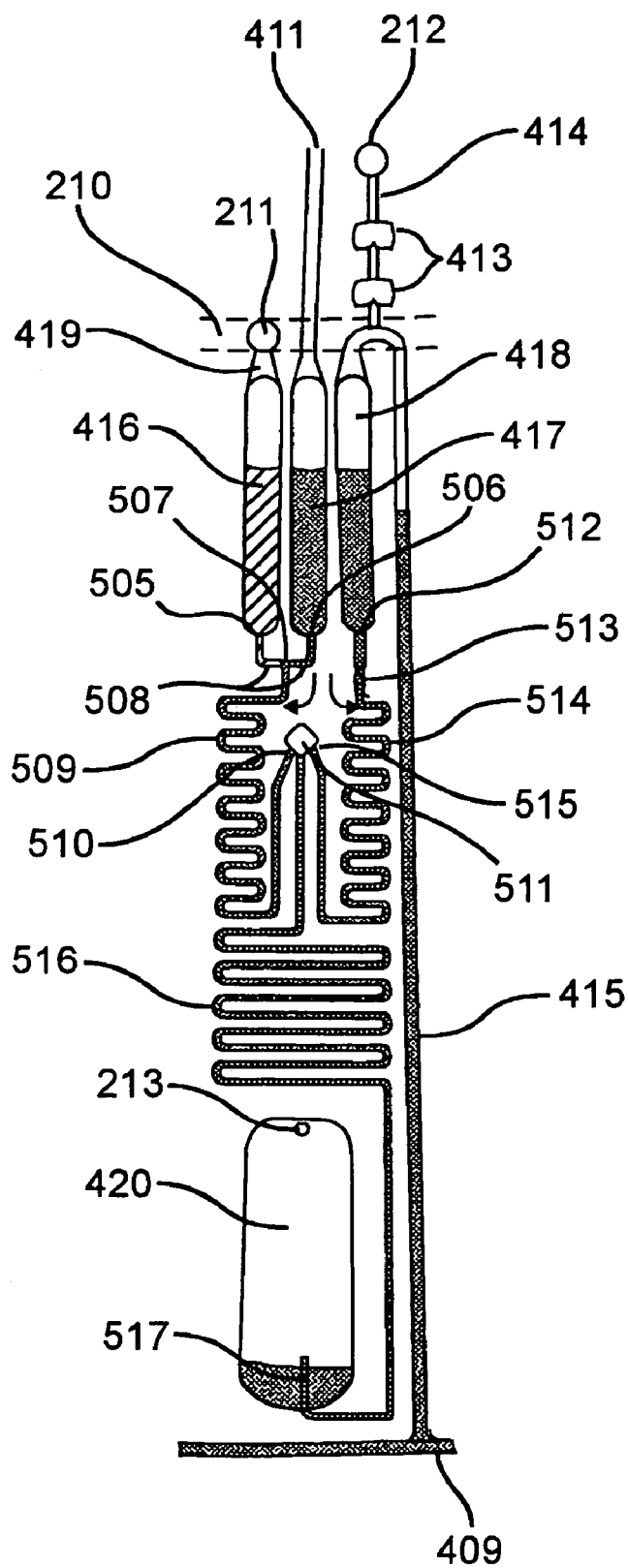

The platform of the invention is used for the performance of assays in the following fashion, referring to FIGS. 7 and 8, which illustrate fluid motion in the vicinity of the reservoirs 401, 402, 403, 404 and an assay structure, respectively. The assays were run as follows. Aliquots of fluid A are added ports 203+204; the volume of the individual aliquots are identical, but may range depending upon the design of the device from 1 nL to 50 microliters. The chosen volume for the aliquot is such that, when fluid fills reservoir 417, it protrudes into 411 for a short distance, typically less than ⅓ of the length of 417. A total volume of fluid B equal to the number assays multiplied by the volume of fluid B required for each assay, plus an additional volume greater than or equal to the volume enclosed in channels 409 and in all channels 415, is added reservoir 401 through entry port 215. FIGS. 7 and 8 illustrate the sequence of fluid flows in the vicinity of the reservoirs of microfluidic assay elements. FIG. 7a illustrates the flow of fluids entering reservoirs 401 and 402, as well as of samples of fluid A enter ports 217 and channels 414. The platform is then placed on a device that is capable of performing rotations. At a first rotational speed ranging from 100-1000 rpm, fluids A are driven through channels 411 into the reservoirs 417, where they are retained by capillary junctions 508. This is illustrated in FIGS. 7a-7d and 8a through 8d. Also at this rotation rate, fluid B is driven through hole 207 into manifold 210. As fluid B travels 210, it flows through the vias 211 into passageways 419 and finally reservoirs 416, where it was retained by capillary junctions 508. Fluid B also passes through via 218 and is retained at capillary junction 520 of overflow structure 503. Also at this rotation rate, fluid C is driven through channel 408 and manifold 409 to the fill channels 414, and then to aliquotted reagent reservoirs 418. Fluid in aliquotted reagent reservoir 418 is stopped at capillary junction 513. Fluid C also enters capillary 414 and is stopped at capillary junction 413. Fluid C completely fills 409 and is also stopped at capillary junction 520 over overflow structure 503. The rotational rate is then increased to a second speed. At this speed, the overflow capillary valves formed 520 on the overflow structures 503 and 504 release. Fluid A in manifold 210 flows into the overflow reservoir 403, leaving behind solution in the reservoirs 416. Similarly, fluid C flows into reservoir 402; as it flows, the fluid in each assay structure at capillary junctions 413 is "pulled". However, the fact that aliquotted reagent reservoir 418 is radially-outward from 413 means that there is rotationally-induced resistance to drawing the fluid from aliquotted reagent reservoir 418. The tension in the fluid at 413 is relieved through the introduction of air via the channel and port 212; by introduction of this air bubble, solution C within the manifold 409+415 is effectively separated from fluid remaining in aliquotted reagent reservoir 418. The speed is then increased to a third value, at which point the capillary junctions at 508 and 513 allows fluid to flow. The fluids from reservoirs 505 and 506 flow through channel 509 and are halted at the junction 510; similarly, the fluid flowing through 514 was halted at the junction 515. At a fourth rotational rate, the capillary junctions at 511 allow the fluids to flow. The mixing fluids are then pumped via centrifugation into the detection reservoir 420. In the case of the junctions 507 and 511, whichever fluid flows first is forced to wet the exit capillary of the other fluid in the capillary junction, thereby inducing it to flow as well.

In some alternative constructions, the various rotational rates need not be monotonically increasing. The velocity may be "spiked" momentarily from a low value to high value when a capillary valving event is desired; if it is then reduced quickly to a lower value, the next capillary valving event may be designed to operate at the same rotational rate as the first or even a lower rate. By using the delay time required for fluid to transit from capillary valve to capillary valve in a sequence, a large number of events may be designed to function serially.

Figure 9:
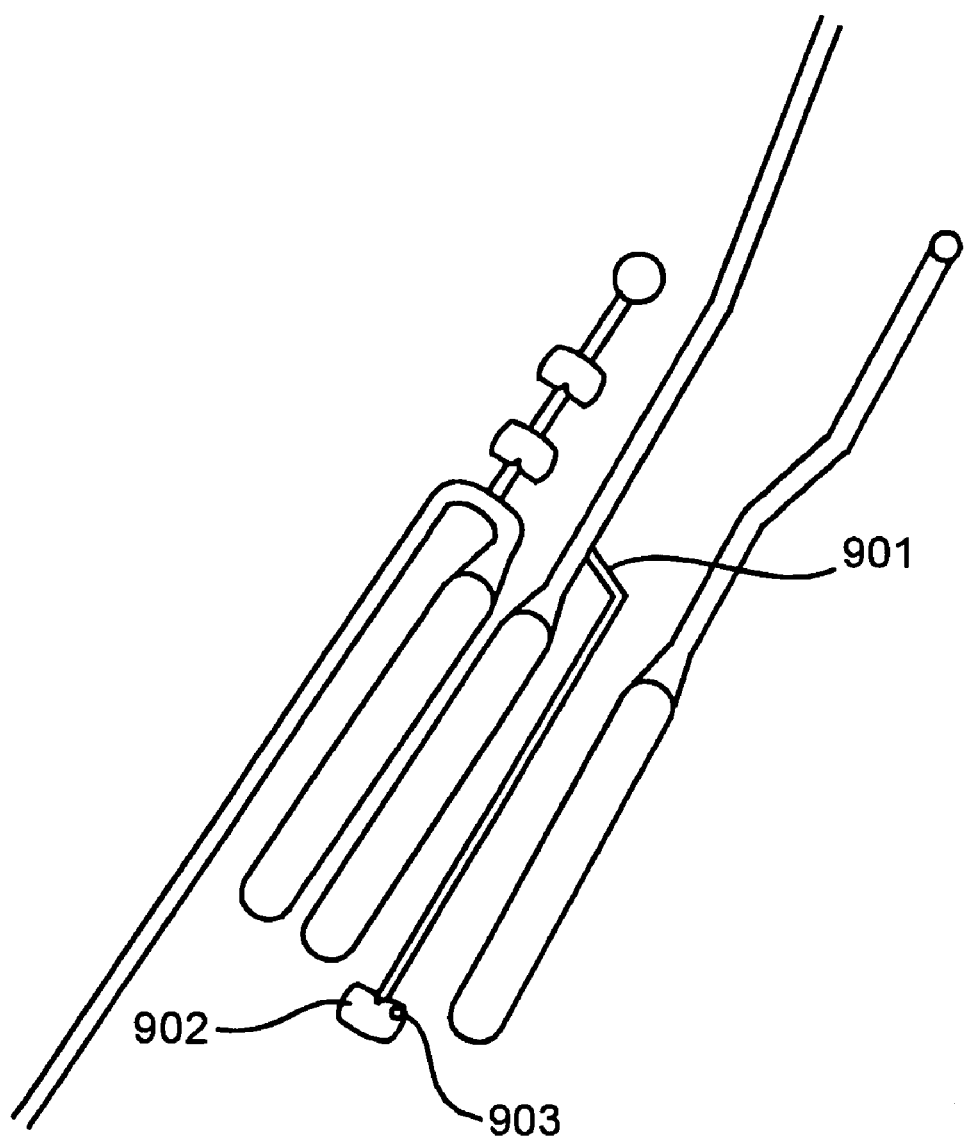
FIG. 9 illustrates a first alternative construction of the microsystems platform in which the sample volume is metered by the construction of the device.

Three alternative constructions of the fluidic design are now discussed. FIG. 9 illustrates a detail of the lower face of the fluidics layer 201 of the platform depicted in FIGS. 1 through 5. Most of the features illustrated correspond to those of FIGS. 2 through 4. It will be understood that the structures in microfluidic layer 500 are sized and spaced so that they mate with those of layer 201 in the preceding example. The additional elements in this embodiment are capillary 901, a combined capillary junction and overflow chamber 902, and air-vent 903. This embodiment is designed to meter an imprecise volume of "sample" fluid for each assay structure. The function of this alternative is the same as in the previous embodiment, with these additional features: At the first rotational speed, sample fluid is delivered via channel 411 to reservoir 417. As it flows to the reservoir, some fluid enters capillary 901 but is retained at the expansion of 901 into capillary junction 902. The fluid fills the reservoir and is halted by capillary junction 508 in the microfluidics layer (not shown in this figure). The dimensions of capillary 901 are chosen so that fluid is able to pass opening 902 at a rotational speed intermediate between the first and second rotational speeds discussed above. Displaced air is vented through 903, and fluid that extends radially-inward of the intersection of channel 411 and capillary junction 902 flows into capillary junction 902. Air vent 903 may be chosen to be small enough that fluids cannot escape it at any rotational speed normally used for the device. The selection of the diameter of capillary 901 depends on the expected amount of excess volume. For example, for an assay volume of 0.5 μL and a conventional pipetting device used to apply fluids to the disc having a precision of ±0.2 μL. The device may be designed so that the user is required to add 0.75 μL, as long as the volume of channel 901 is 0.05 μL or less. For example, if the radial position of 902 is the same as that of capillary junction 508 on microfluidic layer 500, the diameter of capillary 901 at capillary junction 902 need only be somewhat larger than that of the channels that meet at capillary junction 507 in order to function. A 100 μm wide and 100 μm deep channel 901 meets requirements.

Figure 10:
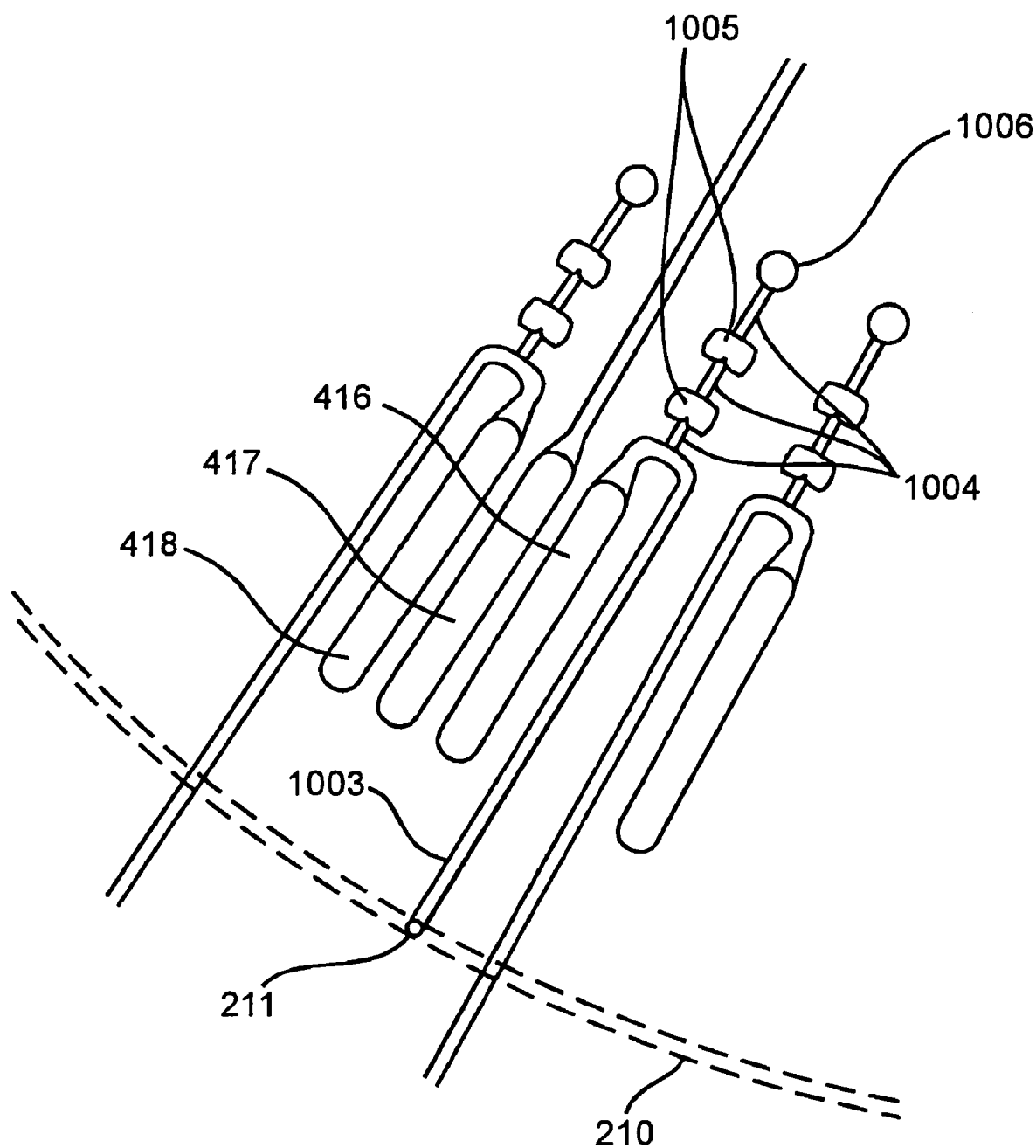
FIG. 10 illustrates a second alternative construction of the microsystems platform in which two common reagents are isolated through the introduction of a bubble.

A second alternative construct is shown in FIG. 10. In this embodiment, the manifold 210 is positioned radially-outward of reservoirs 416, 417, and 418. Via 211 connects with channel 1003 that leads radially-inward to a microchannel configuration identical to that associated with aliquotted reagent reservoir 418 described above, consisting of capillary 1004, capillary junctions 1005, and air vent 1006. It will be understood that this structure behaves like that associated with aliquotted reagent reservoir 418 in the previous description, by isolating fluids in the multiple reservoirs 416 from one another. Modifications in which channel 1003 resides on the "upper" face of the layer 201 are within the scope of the invention, as long as a via connecting the fluid path to the lower face is made, for example, at the radially-proximal end of 416; this may be advantageous in order to "pack" structures most effectively in the azimuthal direction.

This alternate construction may provide advantages for liquids that have unpredictable properties such as viscosity and surface tension. With such fluids, it is possible that bubbles may accidentally be introduced in manifold 210 in the previously described embodiment. These bubbles make draining of the manifold, and isolation of the reservoirs 416, difficult. By introducing bubbles at each reservoir, the need for maintaining a single plug of fluid in manifold 210 is relaxed A third alternative construction with additional functionality is shown FIG. 11. In this Figure, a microfluidic network for the creation of a dilution series is illustrated and is part of a larger network of structures used for various purposes. The fluid distribution scheme illustrated here is advantageous not only for the three-fluid homogeneous assays disclosed herein but can be applied to any centrifugally-based process that requires the creation of such dilution series.

In this embodiment, the platform has only three ports and reservoirs for fluid addition: Reservoirs 401 and 402 for common reagents, as previously discussed, and reservoirs 601 and 602 placed on a surface of the platform 201 and accessed by entry ports 618 and 619 respectively. Reservoirs 401 and 402 lead to distribution manifolds, overflows, and assay reservoirs as previously discussed. Fluid channel 603 exits reservoir 601 and is split into two components at what will be called a T-junction 604, a portion of which continues to further T-junctions and a portion of which, 607, terminates at a capillary junction 609. Similarly, reservoir 602 leads to channel 605, which is split at T-junction 606; one arm of the split channel continues to further T-junctions, while the other arm, 608, terminates at the capillary junction 609. Following channel 603 past T-junction 604, it is again split at T-junction 610 into a portion that leads to reservoir 417 of the left-most assay structure 650. The structure 650, composed of reservoirs and channels as previously disclosed, embodies the same functionality as that given in FIG. 6. Channel 419, for example, is the passage for the entry of first reagent into reservoir 416. The other portion of channel 603 terminates at capillary junction 615. Similarly, channel 605 leads to T-junction 612, where it is split into channel 613 which terminates at capillary junction 618 and a portion which continues to assay structure 651. The capillary junctions 609, 615, and 616 all are fluidly connected to channels 614, 640, and 641, respectively. Channels 640 and 641 lead respectively to assay structures 653 and 654. Channel 614 is further split at a 4-armed junction 617 into 3 channels: A continuation of 614, which leads assay structure 652, and side channels 618 and 619 which terminate at capillary junctions 615 and 616, respectively.

The disc may be used to distribute liquids for an assay in the following fashion. Common reagents are loaded into reservoirs 401 and 402. "Sample" (fluid A) is loaded into reservoirs 601 and a diluent buffer (fluid B) into reservoir 602. Under the influence of rotation, the common reagents are distributed to reservoirs 416 and 418 as previously described. Sample and diluent enter channels 603 and 605. Fluid A reaches the T-junction 604, at which point a portion of the fluid continues down channel 603 and a portion flows into channel 607. Similarly, fluid B splits at 606 into channels 605 and 608. The portion of A present in 607 reaches capillary junction 609, as does the fluid B present in 608. As the disc is spun to overcome capillary force at 609, the fluids are brought together and flow into meandering mixing channel 610. Mixing in this channel is described in co-owned and co-pending application U.S. Ser. No. 09/595,239, filed Jun. 16, 2000, incorporated by reference. The fluid in channel 614, after sufficient time for diffusional mixing in the channel, arrives at junction 617 with a volume fraction of A equal to 0.5 and B equal to 0.5, i.e., the fluids A and B are "mixed". The mixed fluid arriving at 617 is denoted fluid C1.

Fluid C1 is split into 3 streams at junction 617. A portion of that mixed liquid C1 now mixes with the original A solution which has been directed by channel 603 to junction 610 and channel 611, by passing through capillary junction 615. This fluid, denoted C2, is in channel 640 and has volume fraction of A of 0.75 and B of 0.25. Similarly, the fluid in 641 has volume fraction of A of 0.25 and B of 0.75.

The functioning of the remainder of the network of channels is clear from this demonstration. As shown, the fluidic network delivers 5 concentrations of A—1.0, 0.75, 0.5, 0.25, 0.0—to the structures 650, 651, 652, 653, and 654, respectively. In order to achieve these ratios, the flow rates of the two fluids entering any mixing channel 614, 640, and 641 must be equal. This is assured by the diameter of the channels, as fluid flow is controlled by the fluidic impedances of the various mixing channels.

It will be understood that the process of dividing and recombining channels illustrated may be continued indefinitely. One further splitting and recombination in the manner shown would lead to a total of 9 concentrations of A: 1.0, 0.875, 0.75, 0.625, 0.5, 0.375, 0.125, 0.0625, 0.0.

It will further be recognized that this mixing scheme need not be restricted to use with the three-fluid homogeneous assays previously discussed, but may be used to deliver a fluid of arbitrary composition to a point on the platform.

A number of variations in fluidic design are possible, either dictated by assay requirements, fluidic requirements, ease-of-use or reduction in automation or all of these factors. For example, capillary valves have been shown to retain fluids in an intermediate chamber at elevated temperatures, used for incubation (as disclosed more extensively in co-owned U.S. Pat. No. 6,063,589, issued May 16, 2000, incorporated by reference). Assays that require intermediate incubations, for example, because of slow chemical kinetics, may be performed in such structures.

Alternatively, assays for which diffusional mixing is insufficient may require agitation of the fluid to effect mixing. In such a case, active valves can be used, which retain the fluids against the sudden pressure changes induced by agitation, as described in more fully in co-owned and co-pending U.S. Ser. No. 09/315,114, filed May 19, 1999.

It may also be desirable to treat the platform surfaces to change the liquid contact angle for controlling capillary valving properties, as disclosed in co-owned and co-pending U.S. Ser. No. 08/910,726, filed Aug. 12, 1997, incorporated by reference.

Sample Dilution

One embodiment of an arrangement of microfluidics structure adapted for and arranged to accomplish dilution of a sample on the platforms of the invention is shown in FIGS. 14A through 14I. In this embodiment, sample reservoir 1201 is fluidly connected to input port 1202 and to air displacement channel 1203 and vent 1204. Sample reservoir 1201 has a volume of 1 nanoliter to 1 ml and dimensions in the platform of 50 microns to 5 mm. Sample reservoir 1201 is directly connected (i.e., without valving) to metering manifold 1205, having a volume of 1 nl to 1 ml. Metering manifold 1205 is connected to metering channel 1207 through reverse capillary junction 1206, which provides little to no resistance to flow in a direction away from the center of rotation, but prevents backfilling of the metering manifold. Metering channel 1207 has at its end distal to the axis of rotation a capillary valve 1208, which prevents fluid flow except when motivated by sufficient centrifugal force from rotation of the platform. Capillary valve 1208 is fluidly connected distally to the axis of rotation to mixing channel 1217, which is in turn fluidly connected to dilution reservoir 1218, having a volume of 1 nl to 1 ml. Metering manifold 1205 is also fluidly connected to overflow capillary junction 1212 and diluent capillary junction 1211, both of which prevent fluid flow except when motivated by sufficient centrifugal force from rotation of the platform. Overflow capillary 1212 is connected to overflow reservoir 1209, which is vented through vent 1210. In this arrangement, flow into the overflow reservoir 1209 is restricted by reverse capillary junction 1206, wherein fluid occupying metering channel 1207 does not drain into or toward the overflow reservoir and an air-liquid meniscus is formed at reverse capillary junction 1206. In some embodiments, there may exist a spacing 1283 that exists between the diluent capillary junction 1211 and the closest reverse capillary junction 1206. During the sample filling process, this volume may remain filled with air. Such an air bubble may interfere with the operation of the device from that point forward. Therefore, the introduction of a trap 1282 provides a place for the air bubble to reside to prevent it from interfering with device operation. To be effective, this trap need only appear at any location in the system where the air bubble will pass by.

Also arranged on the platform, proximal to the axis of rotation with respect to metering manifold 1205, is diluent reservoir 1213 having a volume of 1 microliter to 1 ml. Diluent reservoir 1213 is also fluidly connected to input port 1214, air displacement channel 1215 and vent 1216, and to diluent capillary junction 1211. In certain arrangements, diluent capillary junction 1211 permits diluent to flow into metering channel 1207 with adequate pressure to push sample fluid in metering channel 1207 through the meter capillary junction 1208, through mixing channel 1217 and into dilution reservoir 1218. Dilution reservoir 1218 is also connected to air displacement channel 1219, vent 1220 and diluent reservoir capillary junction 1221. In certain embodiments, dilution reservoir 1218 further comprises capillary junction 1222 that is fluidly connected to assay channel 1223. In these embodiments, capillary junction 1222 and assay channel 1223 are located on the disk distal to the axis of rotation from diluent reservoir capillary junction 1221.

The practice of the methods of the invention are illustrated for drug dilution in FIGS. 14A through 14I. Drug is loaded into the sample reservoir 1201 through input port 1202. Air that previously occupied the sample reservoir will vent through air displacement channel 1203 and vent 1204. The sample then fills metering manifold 1205. The sample preferentially fills metering manifold 1205 in a specific order. It first fills metering channel 1207 after passing through reverse capillary junction 1206, which has minimal to no resistance to flow in the direction from the metering manifold 1205 into the metering channel. The sample fills metering channel 1207 until reaching sample metering capillary junction 1208. The remainder of the metering manifold 1205 fills up to the diluent capillary junction 1211 and the overflow capillary junction 1212. Then, the remainder of the sample fluid exits the metering manifold through the overflow capillary junction 1212 into the overflow reservoir 1209, which is vented through vent 1210, flow being restricted by reverse capillary junction 1206 to prevent fluid occupying metering channel 1207 from draining into or toward the overflow reservoir and an air-liquid meniscus is formed at reverse capillary junction 1206.

After sample has been distributed on the disk, diluent is loaded into the diluent reservoir 1213 through input port 1214, and air vented through air displacement channel 1215 and vent 1216. In alternative and equivalent embodiments, diluent is loaded onto the disc into the diluent reservoir 1213 through input port 1214, and air vented through air displacement channel 1215 and vent 1216 prior to or concomitantly with sample loading. In these embodiments, capillary valve 1211 is configured to prevent diluent fluid flow through the valve at the disc rotation speeds used to motivate sample fluid flow into metering manifold 1205 and overflow reservoir 1209. Diluent enters metering manifold 1205 through diluent capillary junction 1211. Preferably, it first fills metering channel 1207 with adequate pressure to push the sample fluid in metering channel 1207 through the meter capillary junction 1208, through mixing channel 1217 and into dilution reservoir 1218. Air that previously occupied dilution reservoir 1218 is vented through air displacement channel 1219 and vent 1220. Diluent continues to flow into metering channel 1207, mixing channel 1217, and dilution reservoir 1218 until flow stops when liquid reaches diluent reservoir capillary junction 1221. At this point, the remainder of the diluent exits the metering manifold through overflow capillary junction 1212 into overflow reservoir 1209. As when the sample fluid exits into the overflow reservoir 1209, the air-water meniscus is located at reverse capillary junction 1206. The final diluted sample is now located in the volume occupied by dilution reservoir 1218 (which contains the majority of the volume) as well as the volume of mixing channel 1217 and metering channel 1207. In additional embodiments, the diluted sample may later exit these volumes through capillary junction 1222 and into assay channel 1223.

Figure 15A:
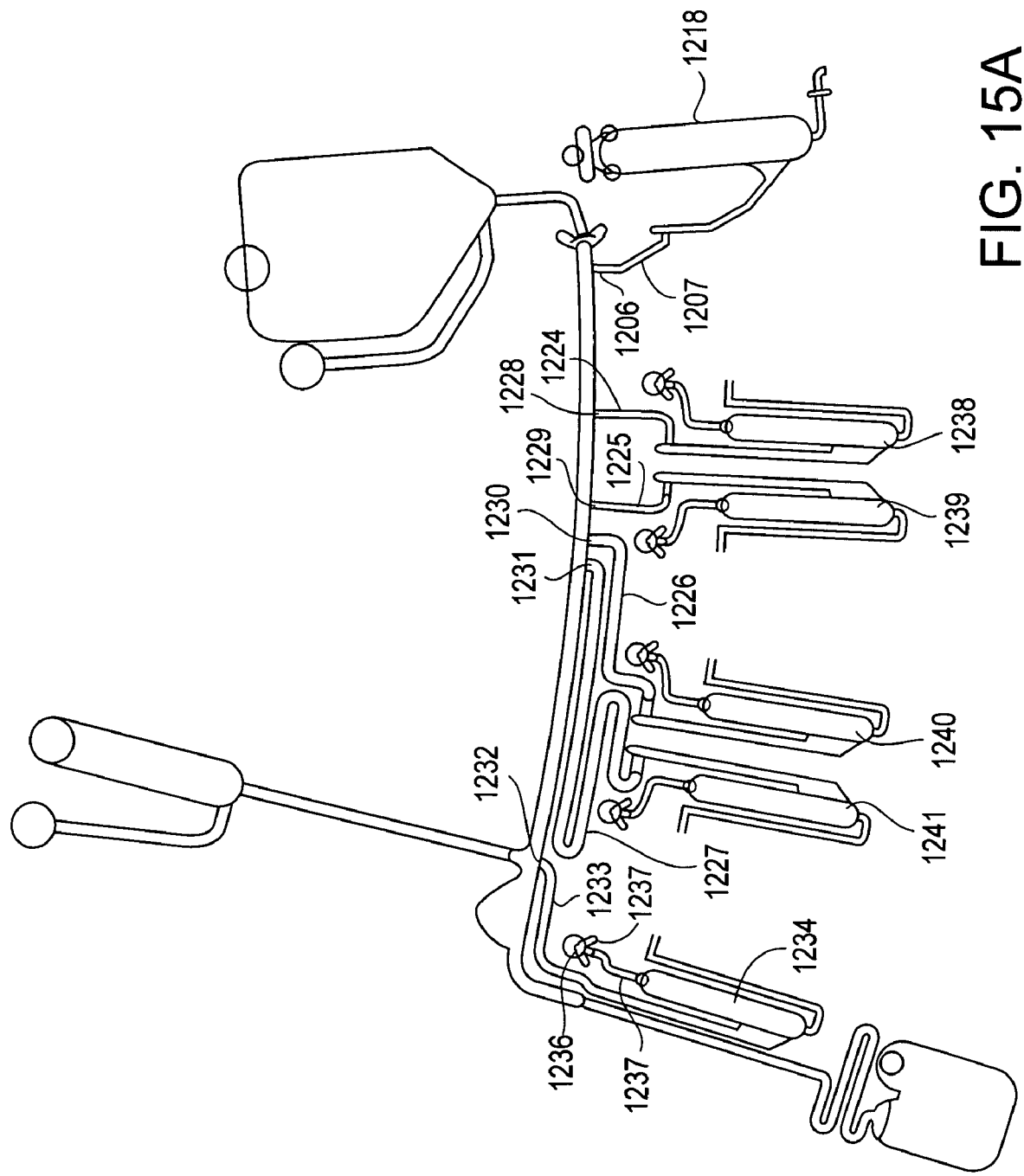
FIGS. 15A and 15B shows an arrangement of microfluidics structures on a disc of the invention for performing parallel dilution of a biological sample (e.g., a drug).
Figure 15B:
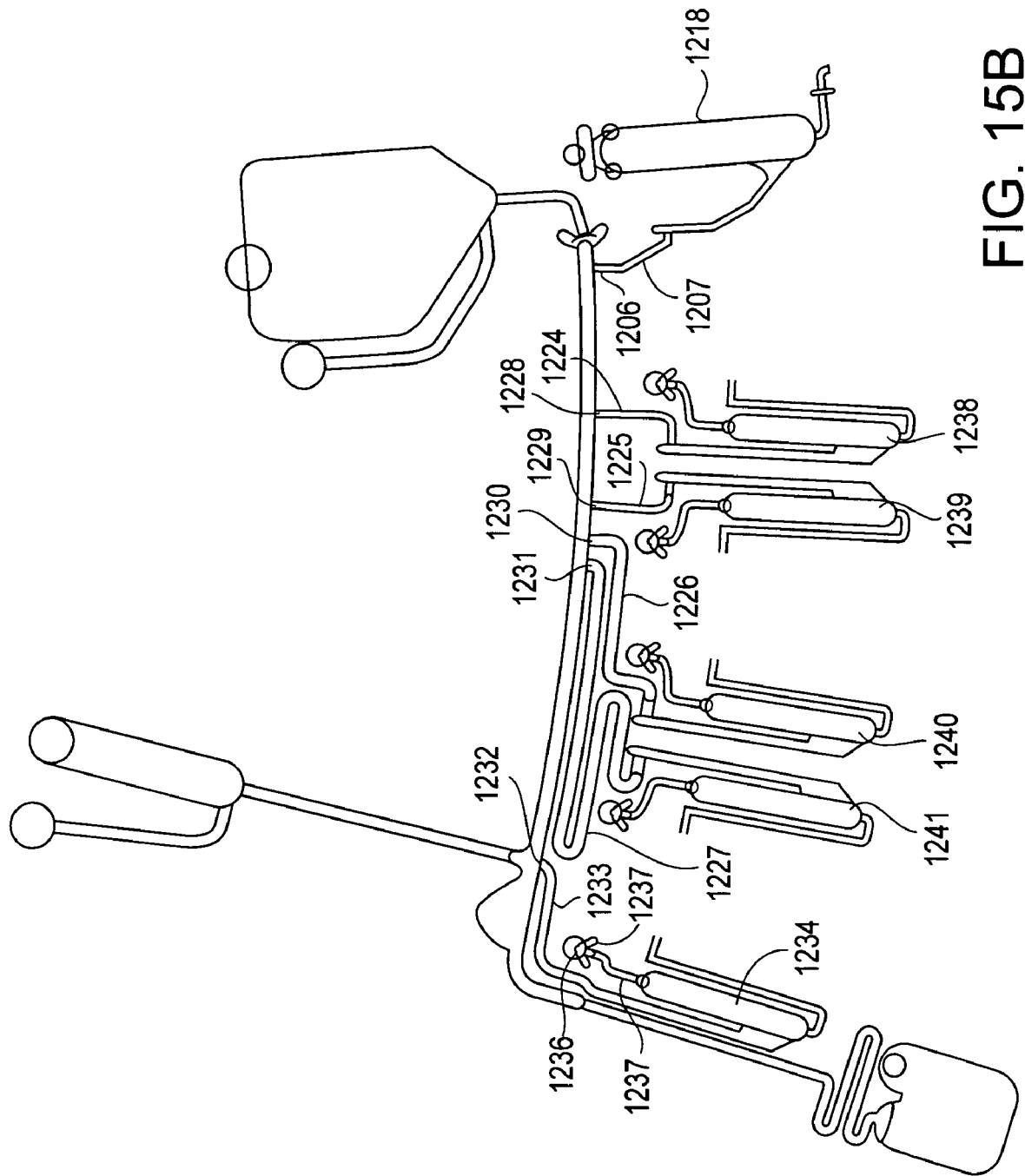

Alternative embodiments are arranged to provide parallel dilution of a multiplicity of samples on a single disc. One such arrangement is shown in FIGS. 15A and 15B. In these embodiments, a plurality of metering channels 1207, 1224, 1225, 1226, and 1227 are arranged and fluidly connected to sample reservoir 1201. Each of the metering channels 1207, 1224, 1225, 1226, and 1227 may have a different volume, depending on the desired dilution factor. Each metering channel 1207, 1224, 1225, 1226, and 1227 is preceded by a reverse capillary junction 1206, 1228, 1229, 1230, and 1231 and leads to a dilution reservoir 1218, 1238, 1239, 1240, and 1241. By varying the volume of the metering channels 1207, 1224, 1225, 1226, and 1227 but keeping the volume of the dilution reservoirs 1218, 1238, 1239, 1240, and 1241 the same, the dilution factor of the resulting fluid volume that fills each dilutions reservoir 1218, 1238, 1239, 1240, and 1241 will be different. For example, the volume of each dilution reservoir 1218, 1238, 1239, 1240, and 1241 may be 2 µl. The volumes of the metering channels 1207, 1224, 1225, 1226, and 1227 may be set to 0.25, 0.5, 0.75, 1 and 1.5 µl respectively. These will be the total volume of sample that will fill the dilution reservoirs 1218, 1238, 1239, 1240, and 1241, respectively. Therefore, the amount of diluent that will fill each of the dilution reservoirs 1218, 1238, 1239, 1240, and 1241 is 1.75, 1.5, 1.25, 1.0 and 0.5 µl, respectively. Thus, the ratio of original sample concentration to final diluted concentration in each of the dilution reservoirs 1218, 1238, 1239, 1240, and 1241, respectively, will be 0.125, 0.25, 0.375, 0.5, and 0.75. The operation of the apparatus and practice of the methods of the invention using these embodiments of the apparatus are as described above, wherein a multiplicity of different dilutions are performed on the same sample.

In another embodiment, varying dilution factors are achieved by keeping the volume of each of the metering channels 1207, 1224, 1225, 1226, and 1227 the same but varying the volume of the dilution reservoirs 1218, 1238, 1239, 1240, and 1241. For example, all metering channels 1207, 1224, 1225, 1226, and 1227 could have a volume of 1 µl. The dilution reservoirs 1218, 1238, 1239, 1240, and 1241 could have volumes of 2, 3, 4, 5 and 6 µl, respectively. The residual volume of each dilution reservoir 1218, 1238, 1239, 1240, and 1241 will fill with diluent. Therefore, the final dilution ratios (as defined herein) of the dilution reservoirs 1218, 1238, 1239, 1240, and 1241 will be 0.5, 0.333, 0.25, 0.2, and 0.167.

Additionally, the volumes of both the metering channels 1207, 1224, 1225, 1226, and 1227 and the dilution reservoirs 1218, 1238, 1239, 1240, and 1241 can be varied to achieve the desired array of dilution ratios. One particularly useful function of this embodiment is to provide adequate diluted volume when some of the dilution reservoirs 1218, 1238, 1239, 1240, and 1241 lead to a larger number of fluidic structures than others. For example, a scenario may require 2 µl of each dilution volume, therefore requiring that the dilution reservoirs 1218, 1238, 1239, 1240, and 1241 have a volume of at least 2 µl. However, if one of the diluted volumes is to be split between providing sample for an assay and some additional function (such as supplying initial sample to a second dilution array), a larger dilution volume is required. It may therefore be desirable in such a scenario to use a range of volumes of dilution reservoirs 1218, 1238, 1239, 1240, and 1241 of 2, 2, 2, 2, and 4 µl, respectively. As will be evident to those skilled in the art, many other final volumes may be desired for each dilution reservoir 1218, 1238, 1239, 1240, and 1241.

In some embodiments, it may be desirable to have one dilution reservoir that contains pure, undiluted sample. This is particularly desirable when performing an assay in which is desired to use sample at its highest possible (undiluted) concentration. In such a case, reverse capillary junction 1232 leads directly to metering channel 1233, where the absence of a mixing channel and dilution capillary junction results in pure diluent flowing through mixing channel 1233, thereby completely filling dilution reservoir 1234 during the initial sample distribution phase of filling. As with all volumes to be filled, there is associated air displacement channel 1235, vent 1236, and capillary valve 1237, as shown in FIG. 18B.

Conversely, in some embodiments it may be desirable to have one dilution reservoir that contains pure diluent without any sample present. In this case, the reverse capillary junction and dilution capillary junction are combined a single element, capillary junction 1242. The absence of a metering channel means that no sample will enter the channel and rather than the entire dilution reservoir 1234 will fill with diluent through mixing channel 1243.

Figure 16A:
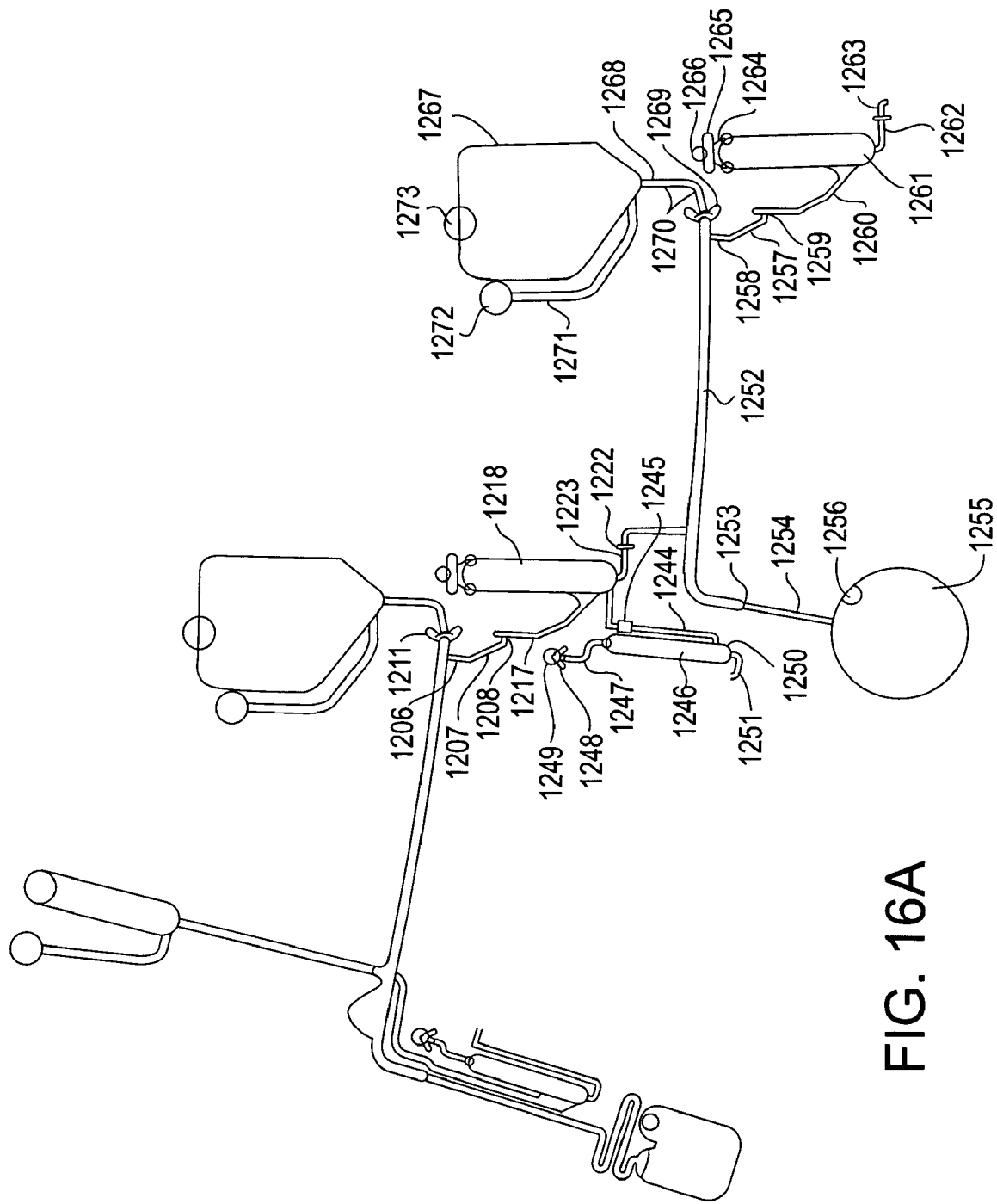
FIGS. 16A through 16C shows an arrangement of microfluidics structures on a disc of the invention for performing serial dilution of a biological sample (e.g., a drug).
Figure 16B:
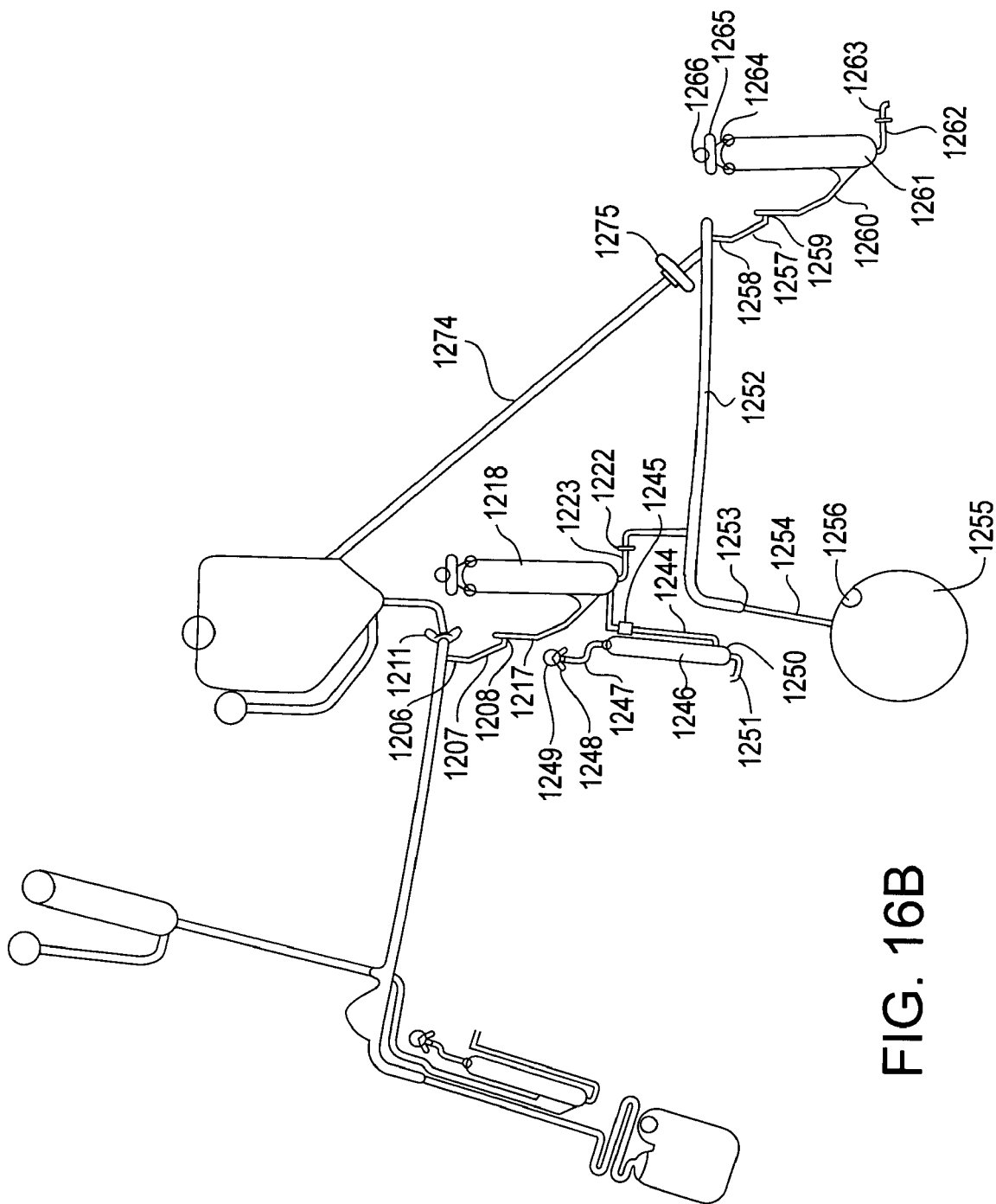
Figure 16C:
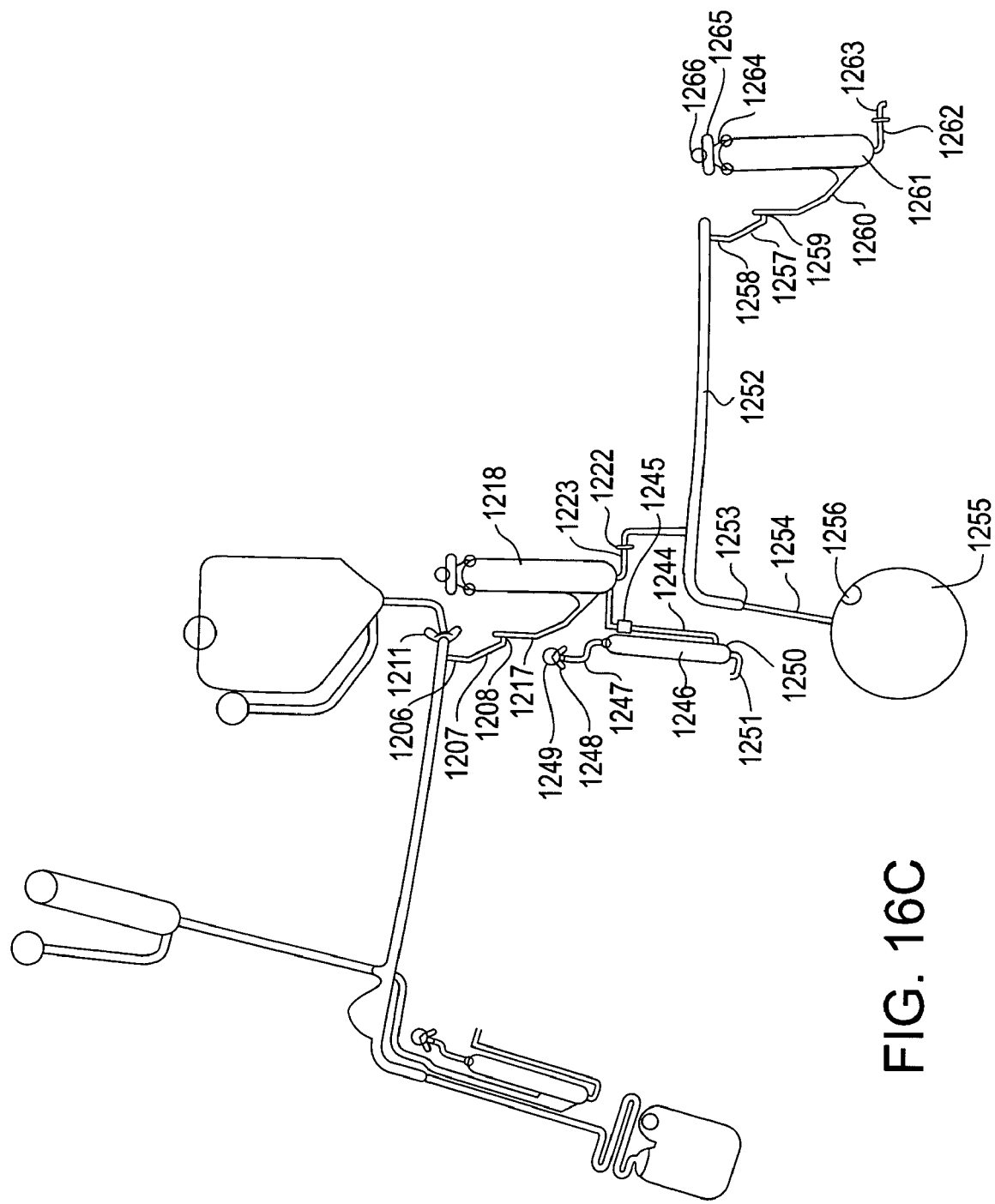

In yet further alternative embodiments, microfluidic structures are arranged to provide serial dilution of samples on a single disc. These structure arrangements are shown in FIGS. 16A through 16C. In these embodiments, dilution reservoir 1218 is fluidly connected to two different microfluidic structures. Dilution reservoir 1218 is connected to feed channel 1244, passing through capillary junction 1245, and connected to dilution reservoir 1246. Dilution reservoir 1246 is connected to air displacement channel 1247, capillary junction 1248, and vent 1249. Dilution reservoir 1246 is further equipped with an assay channel 1250 and capillary junction 1251 for using this dilution volume in an assay or other operation. Dilution reservoir 1218 is also fluidly connected to connecting channel 1223, capillary junction 1222, and metering manifold 1252. Metering manifold 1252 is fluidly connected to metering channel 1257 through reverse capillary junction 1258. Metering manifold 1252 is also fluidly connected to overflow channel 1254 and overflow reservoir 1255 through overflow capillary junction 1253. Overflow reservoir 1255 is further connected to vent 1256. The platform in these embodiments further comprises diluent reservoir 1267, fluidly connected to input port 1273, air displacement channel 1271 and vent 1272. Diluent reservoir 1267 is fluidly connected to channel 1268, capillary junction 1269, and channel 1270, and then to metering manifold 1252. Metering channel 1257 is fluidly connected to dilution reservoir 1261 through capillary junction 1259 and mixing channel 1260. Dilution reservoir 1261 is further connected to air displacement channel 1264, capillary junction 1265, and vent 1266.

In certain embodiments, dilution reservoir 1261 further comprises capillary junction 1263 that is fluidly connected to assay channel 1262. In these embodiments, capillary junction 1263 and assay channel 1262 are located on the disk distal to the axis of rotation from diluent reservoir capillary junction 1261.

Alternatively (as shown in FIG. 16B), diluent may be provided to the second stage of dilution through secondary diluent channel 1274 and capillary valve 1275, connected directly to metering manifold 1252. In other alternative embodiments (shown in FIG. 16C), diluent can be provided to the second stage of dilution through the first diluent reservoir 1213, with diluent traveling through all of the intermediate microfluidic structures to reach dilution reservoir 1261.

In the practice of the serial dilution methods of the invention, after dilution reservoir 1218 is filled, diluent first enters feed channel 1244, passing through capillary junction 1245, and fills dilution reservoir 1246. Air in any or all of these microfluidics structures is vented through air displacement channel 1247, capillary junction 1248, and vent 1249. The remainder of the volume contained in dilution reservoir 1218 flows into connecting channel 1223, passed through a capillary junction 1222, and enters a metering manifold 1252. The filling process is identical to that described above. Sample fills the metering manifold 1252 and enters a metering channel 1257 through a reverse capillary junction 1258. The remainder of sample then passes through overflow capillary junction 1253, into overflow channel 1254, and overflow reservoir 1255. Air escapes the overflow reservoir through vent 1256. Next, diluent is provided from diluent reservoir 1267, which was loaded through input port 1273, utilizing air displacement channel 1271 and vent 1272. Diluent flows through channel 1268, capillary junction 1269, and channel 1270, and then enters metering manifold 1252. Dilution reservoir 1261 is then filled by a mixture of sample and diluent through dilution capillary junction 1259 and mixing channel 1260, and air is displaced through air displacement channel 1264, capillary junction 1265, and vent 1266. Assay channel 1262 and capillary junction 1263 are used for removing fluid from dilution reservoir 1261 for an assay or other purpose. Alternatively, diluent can be provided for the second stage of dilution through secondary diluent channel 1274 and capillary valve 1275, which connects directly to metering manifold 1252. Alternatively, diluent can be provided to the second stage of dilution through the first diluent reservoir 1213, with diluent traveling through all of the intermediate microfluidic structures to reach dilution reservoir 1261.

The invention also provides embodiments of such serial dilution arrangements comprising a plurality of such serial dilution stages, all connected in a serial fashion. In these embodiments, volumes taken from each serial dilution stage (such as in the dilution reservoir 1246) can be used for several subsequence operations, including further dilution. In addition, parallel dilution can be further performed using any or all of the serial dilution stages such that multiple dilutions are formed during any or all of the dilution stages. Such an arrangement microfluidic structures illustrating these embodiments is shown in FIG. 17, having a first dilution stage with 6 parallel dilutions. The sixth such parallel dilution provides the input for the sample reservoir of the second dilution stage, which itself performs 5 dilutions. Note that this Figure also illustrates other reagent reservoirs 1301-1310 that contain a second assay component to be mixed with each dilution.

An example of such embodiments as shown in FIG. 17 are microfluidic platforms that integrate aqueous drug dilution into a disc design comprising a 96-well cuvette format. This design advantageously permits dilution to be performed in the disc, rather than, for example, using off-disc microtitre plates or other dilution fluidics. One advantage of such integration of sample dilution on the disc is an increase in experimental throughput due to the elimination of off-disc serial dilution processed and also the reduction in significant disc loading times. Further advantages are the ability to meter and distribute extremely small volumes ($\leq$15 nl) of sample without the need for complex liquid handling systems, therefore increasing the reliability of the data at high dilution.

The initial drug solution is loaded onto the disc and subsequently fills a distribution manifold, which then leads to the filling of various defined 'metering' volumes, as described above. It is the volume of the metering chamber (along with the volume of the subsequent intermediate cuvette) that defines the dilution ratio for that step. Since the metering volumes are independent of each other, these structures in this arrangement avoids propagation of error that can result from microtitre plate-based serial dilution methods. Any dilution errors that arise using the microsystem platforms in this embodiments of the invention will be due to production errors in defining the metering chamber volume and any errors in filling or emptying the chamber, all of which can be minimized by quality control measures.

Figure 17A:
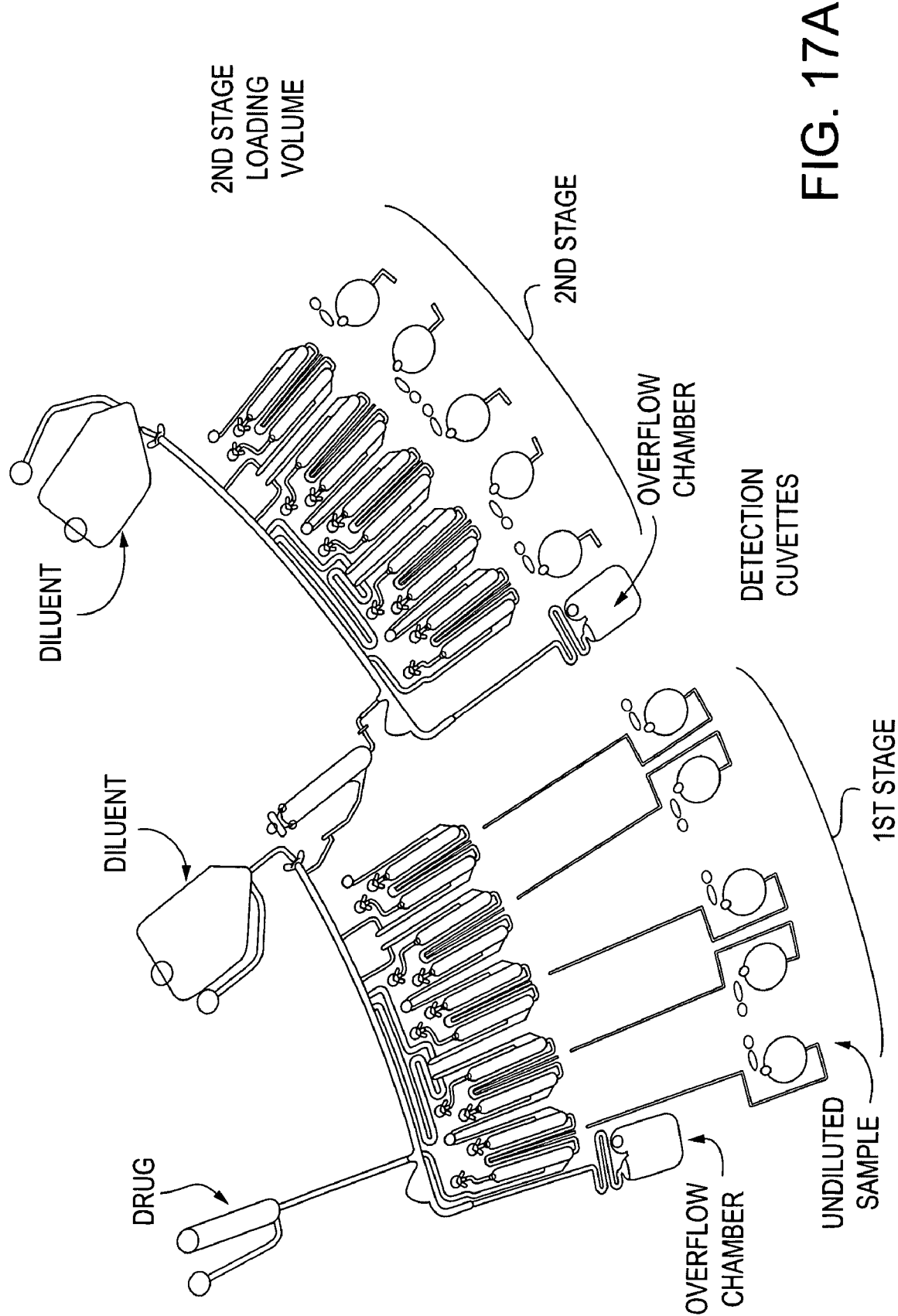

Dilution microfluidics structures are arrayed to perform dilution in two stages, schematically shown in FIG. 17A. This Figure illustrates structures useful in the practice of microsystems platforms equivalent to a 96-well microtitre plate format. This format requires 2 µl final drug sample volumes, and for this volume it is near impossible to meter volumes small enough to obtain anything close to 5 logs (100,000-fold) of dilution in a single stage. Therefore, the first stage performs 5 dilutions in half log increments for a total of 2.5 logs of dilution plus one volume that is undiluted. The 2.5 log dilution point is then the inlet reservoir for the $2^{nd}$ stage, which is a repeat of the first stage in that an additional 4 half log increments of dilution are performed plus one volume that is undiluted (the 2.5 log dilution concentration from the $1^{st}$ stage). This results in a 4.5 log (~32,000) dilution, plus one volume for the originally loaded drug sample.

Figure 18:
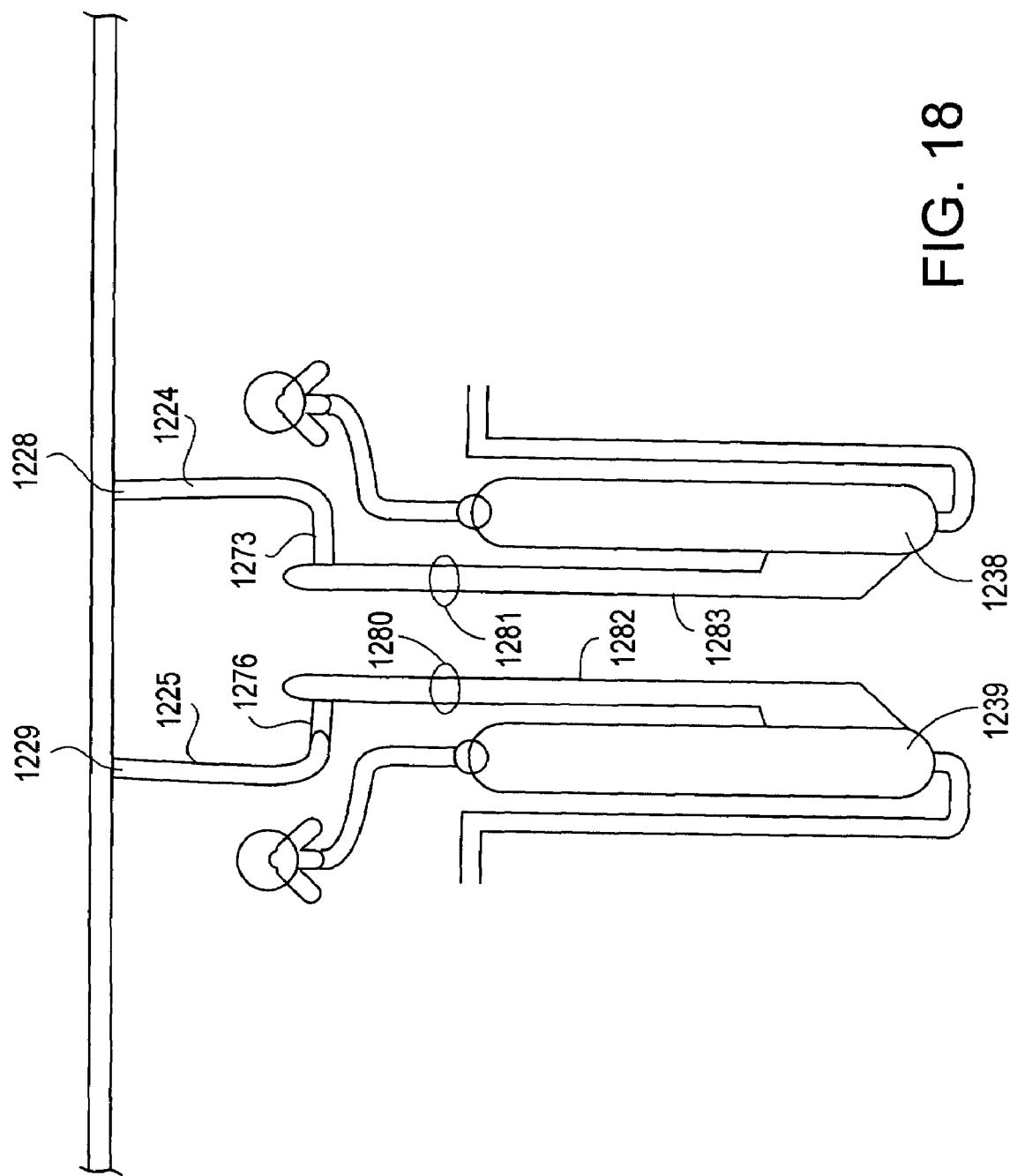
FIG. 18 is an enhanced view of a structure for a mixing element that can be included in the dilution configuration of the microfluidics structures of the platforms of this invention.
Figure 15A:
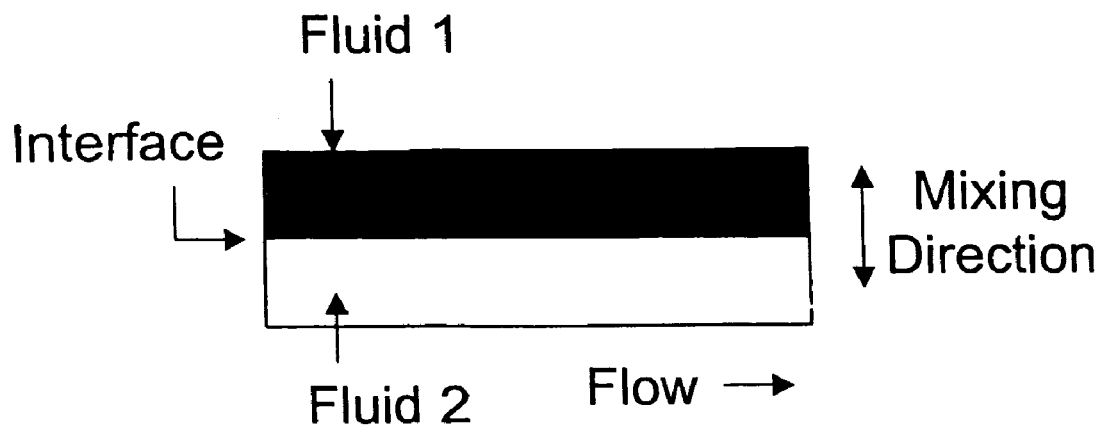
Figure 15B:
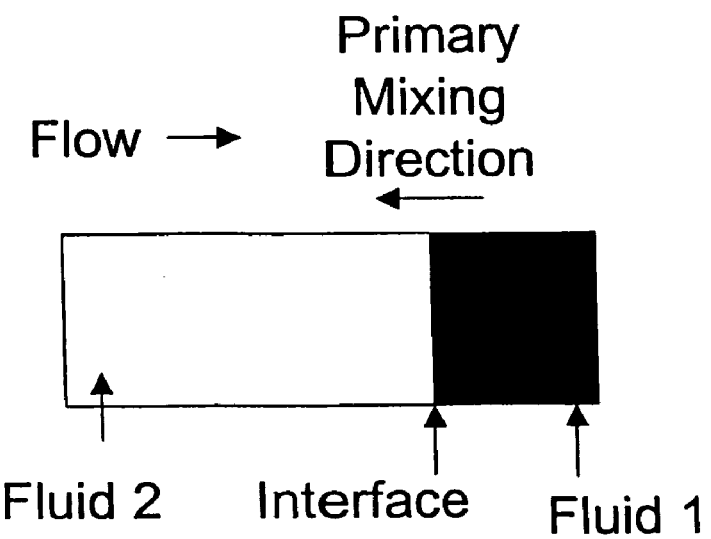

FIG. 18 shows a close-up view of a portion of the dilution structure shown in FIG. 17. Specifically, FIG. 18 shows an additional component a mixing element 1281 that can be located within mixing channel 1279. This mixing element may help ensure that the sample and diluent components are more fully mixed as the fluids are processed through the dilution apparatus. Specifically, when both fluids reach the dilution reservoir 1238, it is preferable that they be fully mixed before any further fluid flow occurs.

Dilution of the original drug sample occurs over the steps depicted in FIG. 17B. Drug and diluent are loaded into the sample reservoir and diluent reservoir(s), respectively. Next, upon initiation of the spin profile, the drug sample fills the distribution manifold, the channel to the overflow reservoir, the metering chambers, and the intermediate cuvette. As the drug fills the manifold, it will trap an air bubble in the diluent valve. Once the metered volumes are filled with the drug sample, the valve holding the diluent reservoir breaks. Then the bubble trapped in the diluent valve pushes down the manifold while the trailing diluent washes out the drug sample from the manifold and into the overflow reservoir (the drug sample remains in the metering chambers). The bubble, when at the end of the manifold gets trapped in the bump-out in the manifold near the drug inlet. This prevents the bubble from blocking the channel leading to the overflow chamber. Next, the rotation rate of the disc is increased and the exit valve to the metered chambers breaks and the corresponding drug samples are diluted by the diluent as the fluids fill individual intermediate cuvettes. The exits to the intermediate cuvettes are valved. Finally, the remaining diluent and drug flow out of the manifold and into the overflow chamber, thus breaking the fluid trail above each dilution volume. This process is repeated for the second stage, while the diluted drug samples remain in the intermediate cuvettes of the first stage.

The degree of dilution, or dilution ratio, DR, can be theoretically predicted based on the volume of the metered chamber, $V_{meter}$, and the volume of the intermediate cuvette, $V_{int}$, that the fluid enters according to the following formula $$DR = \frac{V_{meter}}{V_{meter} + V_{int}}$$

As provided herein, the mixing element is any means that performs mixing on the fluids. In some cases, mixing may be thorough mixing while in other cases it may be only partial mixing. There are numerous microfluidic structures that can act as a means for performing mixing. Some mixers are transverse, in the sense that fluid elements are mixed in a transverse fashion relative to the flow direction. In other cases, mixing is axial, in the sense that fluid elements are mixed along the direction of flow. These different mixing alternatives are illustrated schematically in FIGS. 19A and 19B.

Figure 20:
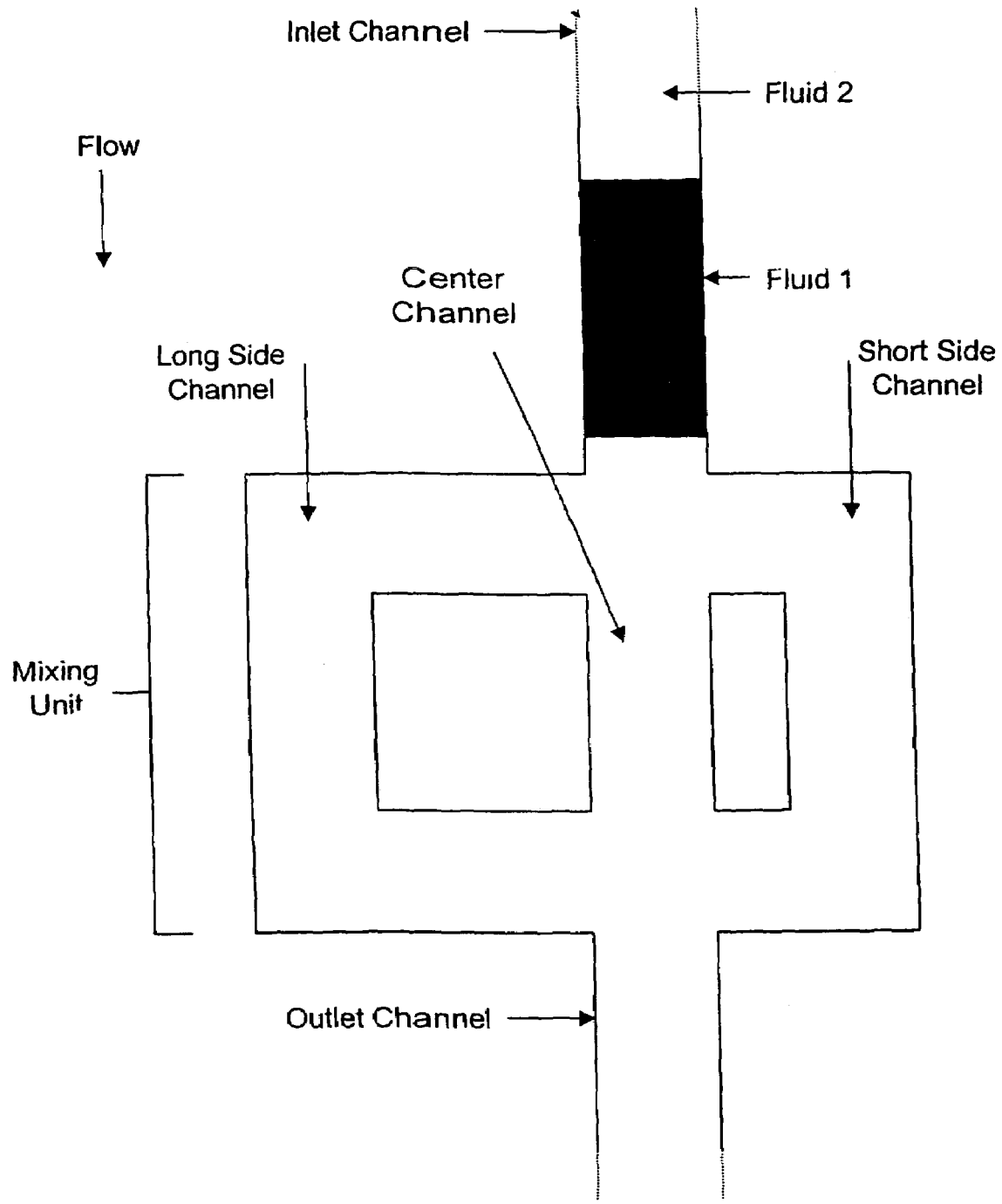
FIG. 20 shows a mixing microchannel comprising a center channel and two side channels.
Figure 21:
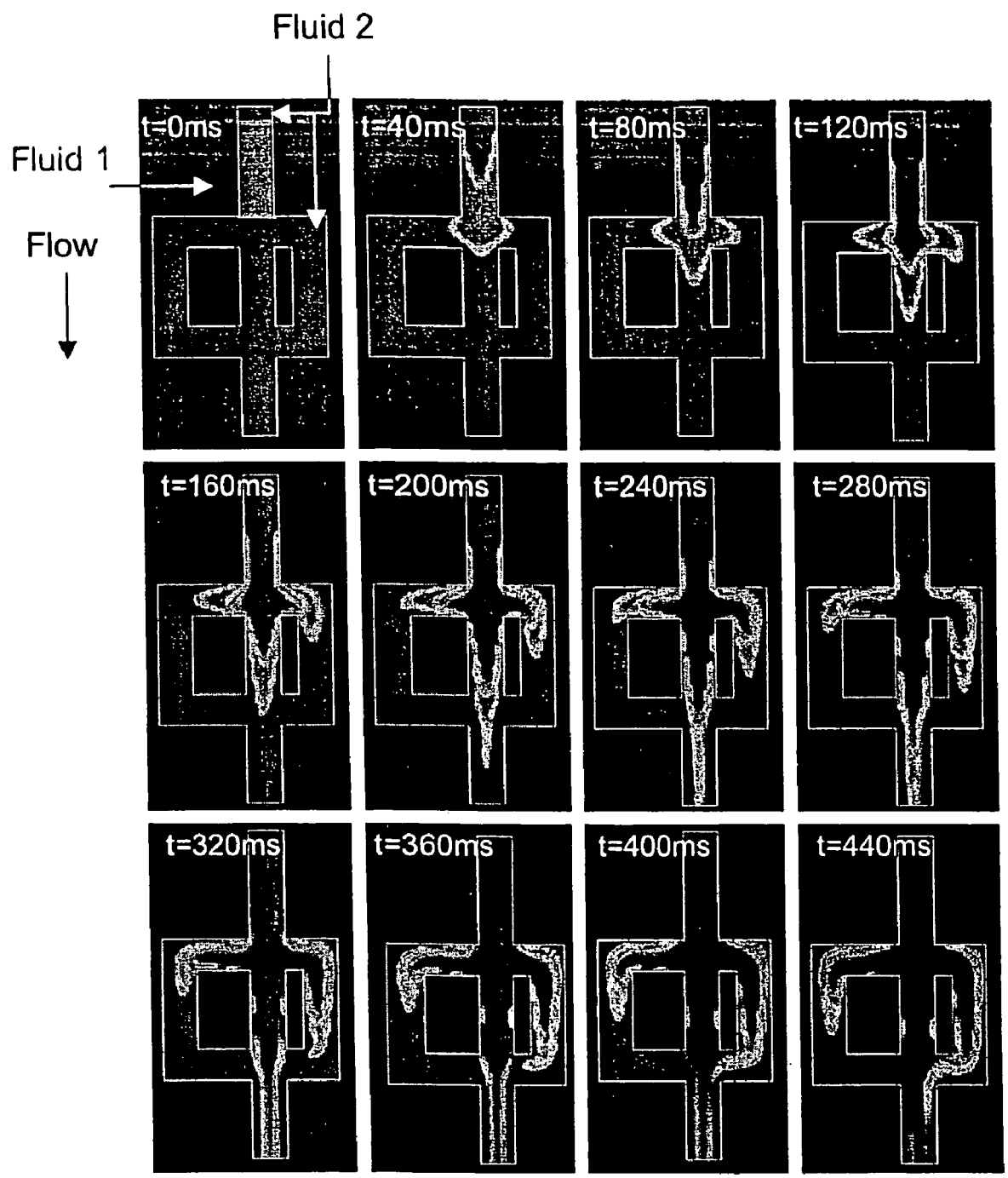
FIG. 21 is a stop-action photograph of fluid mixing using the mixing microchannel illustrated in FIG. 20.

In certain embodiments, the mixer is a mixer described in co-owned U.S. provisional patent application Ser. No. 60/436335 (filed Dec. 24, 2002, incorporated by reference). The structure of this mixer is shown in FIG. 20. This mixer is primarily an axial mixer, although it has a transverse component as well. The mixer can be placed in line with any microfluidic channel and provides three paths for fluid to flow, some with different residence times. As will be evident to those skilled in the art, such a mixing element could be comprised of as few as 2 channels or a substantially larger number of channels, from about 4 to 100. The differing flow residence time of the legs of this mixing element is shown in FIG. 21.

Another in-line mixer element is one that splits and then recombines fluid flow. In some instances, flow is spilt into smaller channels so that diffusion distances to achieve mixing are shorter, thereby decreasing the time or flow distance for mixing (see Bessoth et al., 1999, *Anal. Comm.* 36: 213-215). In other cases, bends or turns are introduced into the microchannel to induce rotation and/or helical flow in the fluids to increase mixing (see Liu et al., 2000, *J. Microelectromechanical Systems* 9: 190.). In other cases, grooves or other non-uniformities are introduced into the microchannel to induce ebbing, rotation, and/or helical flow (see Stroock et al., 2002, *Science* 295: 647).

All of the above mixers can be used separately or in combination to provide some degree of in-line mixing. Numerous examples of these types of mixers are illustrated in FIG. 22-34.

FIG. 22 shows the structure of a single-level split-mixer, wherein each of two fluids enter through their own respective ports, and combine together in co-parallel laminar flow. The main channel, which has cross-sectional dimensions of 250 µm by 250 µm, is periodically interrupted by bifurcations, where half of the flow in the main channel is directed to each branch of the bifurcation. The flow then recombines into a merged portion of the main channel.

FIG. 23 shows the structure of a double-level split-mixer, wherein each of two fluids enter through their own respective ports, and combine together in co-parallel laminar flow. The main channel, which has cross-sectional dimensions of 250 µm by 250 µm, is periodically interrupted by bifurcations, where half of the flow in the main channel is directed to each branch of the bifurcation. In this case, the thickness of each branch of the bifurcation is halved at approximately the halfway point of the length of each bifurcation branch. Because the narrower half of each bifurcation branch is located in a different level, one branch has its narrow channel in the upper level, while the other branch has its narrow channel in the lower level. The flow then recombines into a merged portion of the main channel. At the next bifurcation, the arrangement of narrowed channels is reversed such that the channel narrowings are located in the opposite layer than in the previous bifurcation.

FIG. 24 shows an alternate design of the double-level split-mixer that is identical to that of FIG. 23 except that the channel narrowing are not alternated, such that the narrow channels on either side of the main channel are always located in either the top or bottom layer, respectively.

FIG. 25 shows a double-level split-mixer design of FIG. 23 extended to show 6 consecutive subunits of the mixer.

FIG. 26 shows a fork split-mixer, wherein each of two fluids enter through their own respective ports, and combine together in co-parallel laminar flow. The main channel, which has cross-sectional dimensions of 125 µm by 250 µm, is interrupted by a single bifurcation, where half of the flow in the main channel is directed to each branch of the bifurcation. Each branch is fluidly connected to a second main channel, where the fluid from the two branches recombines in a serial format. This differs from the examples shown in FIGS. 22-25 in that those examples show recombinations that occur in a parallel format. The second main channel represents a second subunit, where flow is later bifurcated again.

Figure 28:
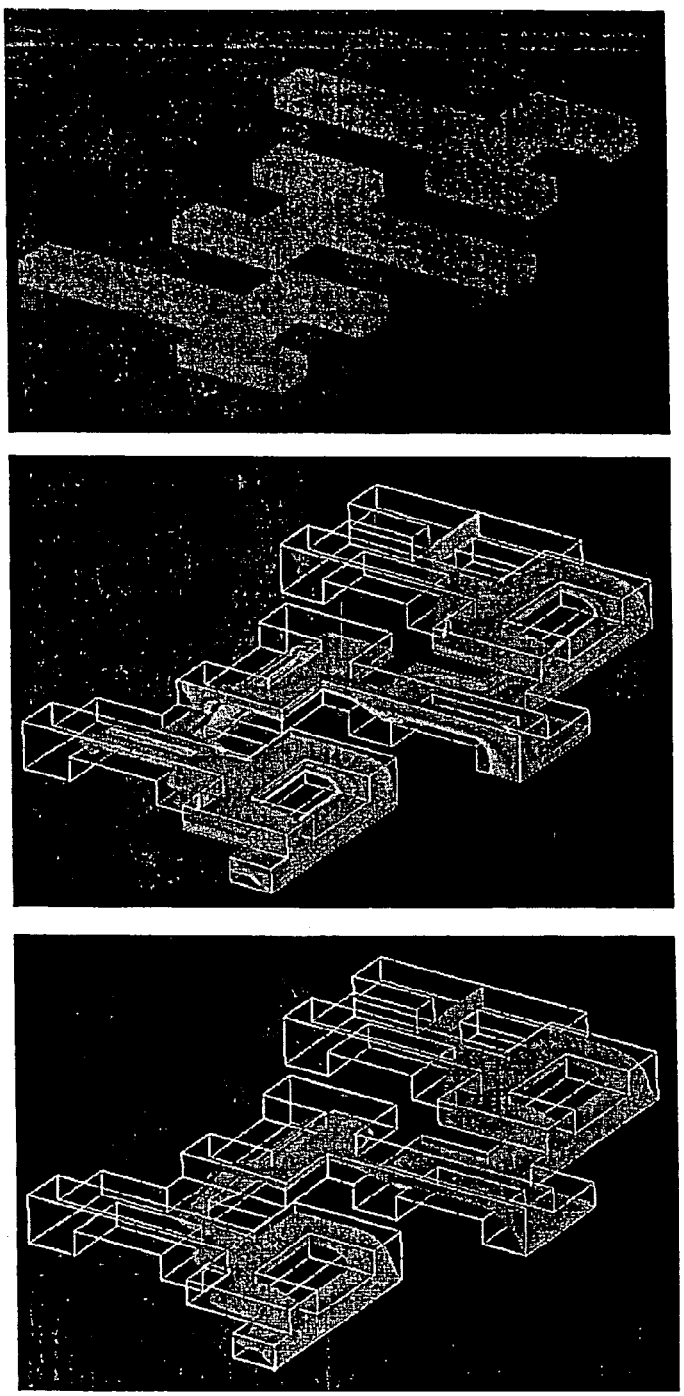
FIG. 28 shows the arrangement of microfluidic structures in a two-level, six-split design fork mixing microchannel.

FIG. 27 shows the structure of a split-mixer is identical to the example in FIG. 26 except that the main channel cross-sectional dimensions are 50 µm by 250 µm, and FIG. 28 shows the structure of 6 subunits of the mixer shown in FIG. 26.

Figure 29:
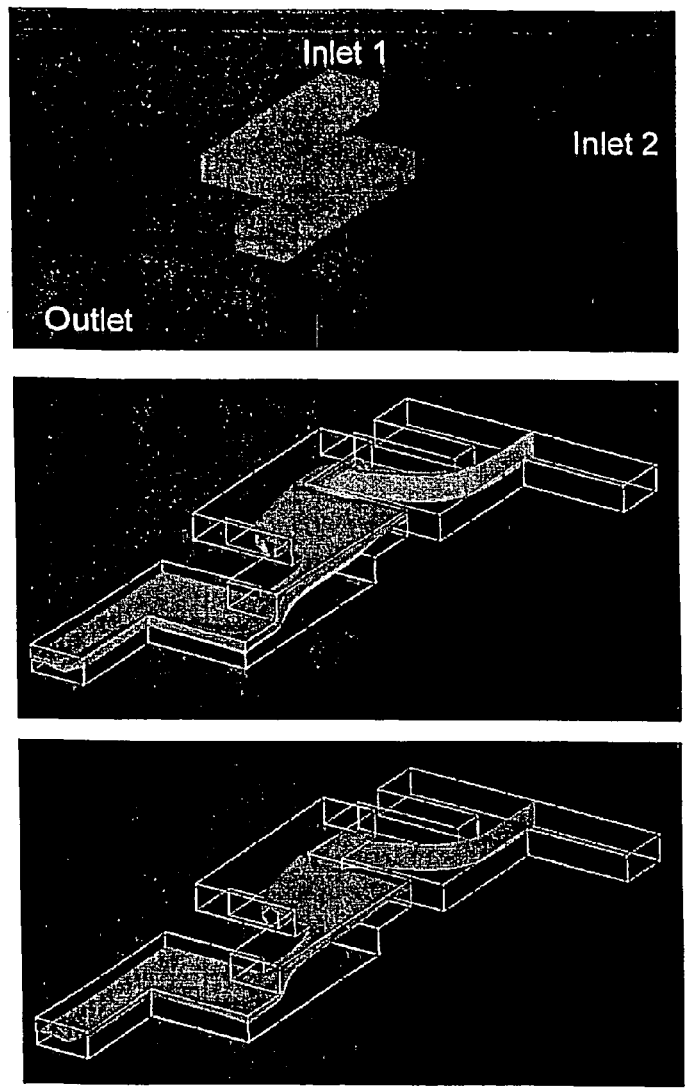
FIG. 29 shows the arrangement of microfluidic structures in a two-level, two-split shuffle mixer design of a mixing microchannel.

FIG. 29 shows the structure of a shuffle-mixer, wherein each of two fluids enter through their own respective ports, and combine together in co-parallel laminar flow. The main channel, which has cross-sectional dimensions of 125 µm by 250 µm, connects fluidicly to an S-shaped channel located in the other layer. The end of this S-shaped channel connects to a second S-shaped channel located in the original layer. The overall affect is a spiral-like pathway that caused the fluid to take sequential turns in different directions.

Figure 30:
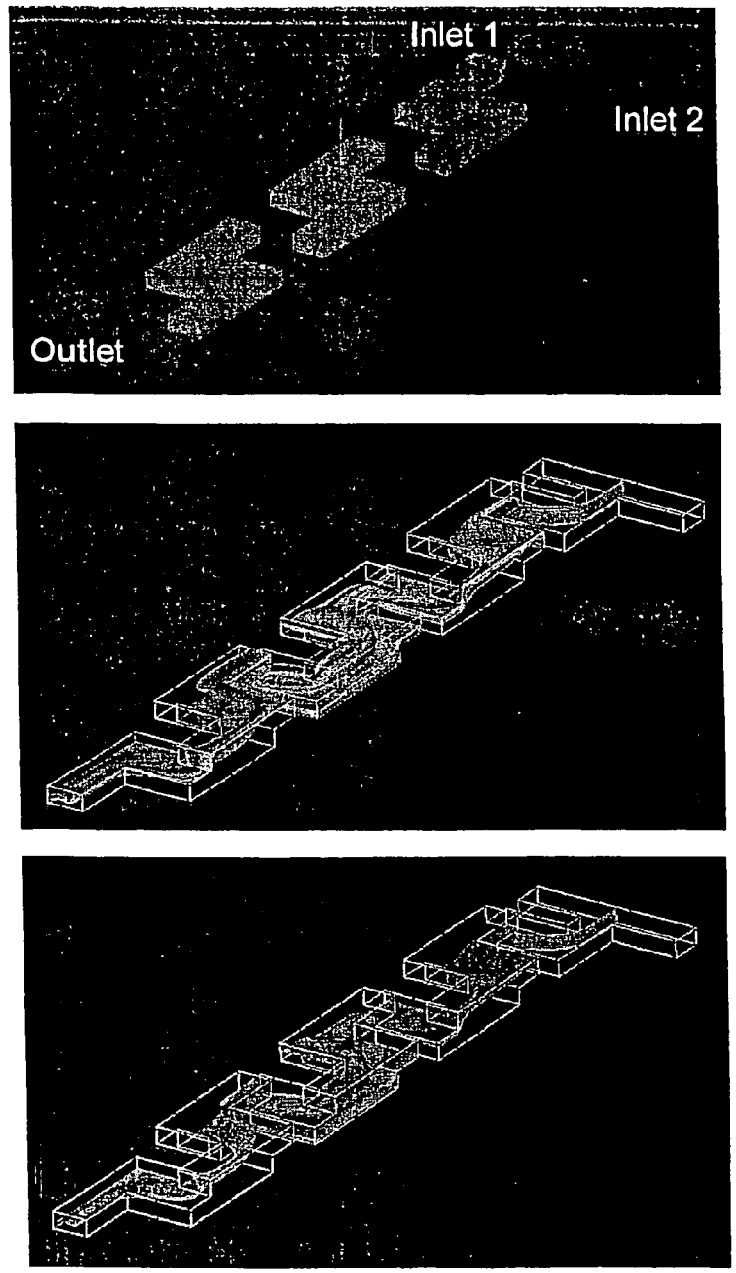
FIG. 30 shows the arrangement of microfluidic structures in a two-level, six-split shuffle mixer design of a mixing microchannel.

FIG. 30 shows the structure of 6 subunits of the mixer shown in FIG. 29.

Figure 31:
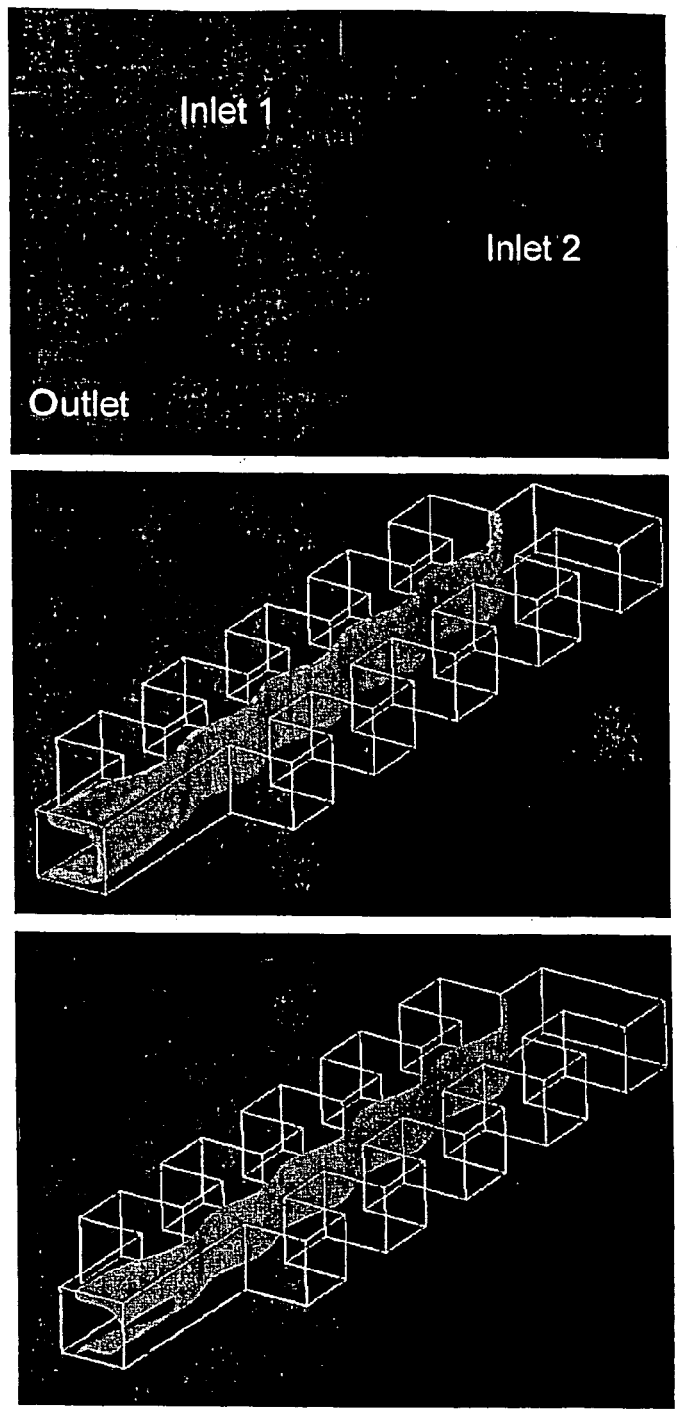
FIG. 31 shows the arrangement of microfluidic structures in a single-channel, comb mixer.

FIG. 31 shows the structure of a single-channel comb mixer, wherein each of two fluids enter through their own respective ports, and combine together in co-parallel laminar flow. The main channel, which has cross-sectional dimensions of 50 µm by 50 µm, has associated chambers located on either side of the main channel in alternating fashion. Such features increase the average residence time inside the device, while also causing a spatial shift in the fluids that promotes mixing.

FIG. 32 shows the structure of a modification of the mixer in FIG. 31, where the main channel thickness has been increased to 100 µm.

Figure 33:
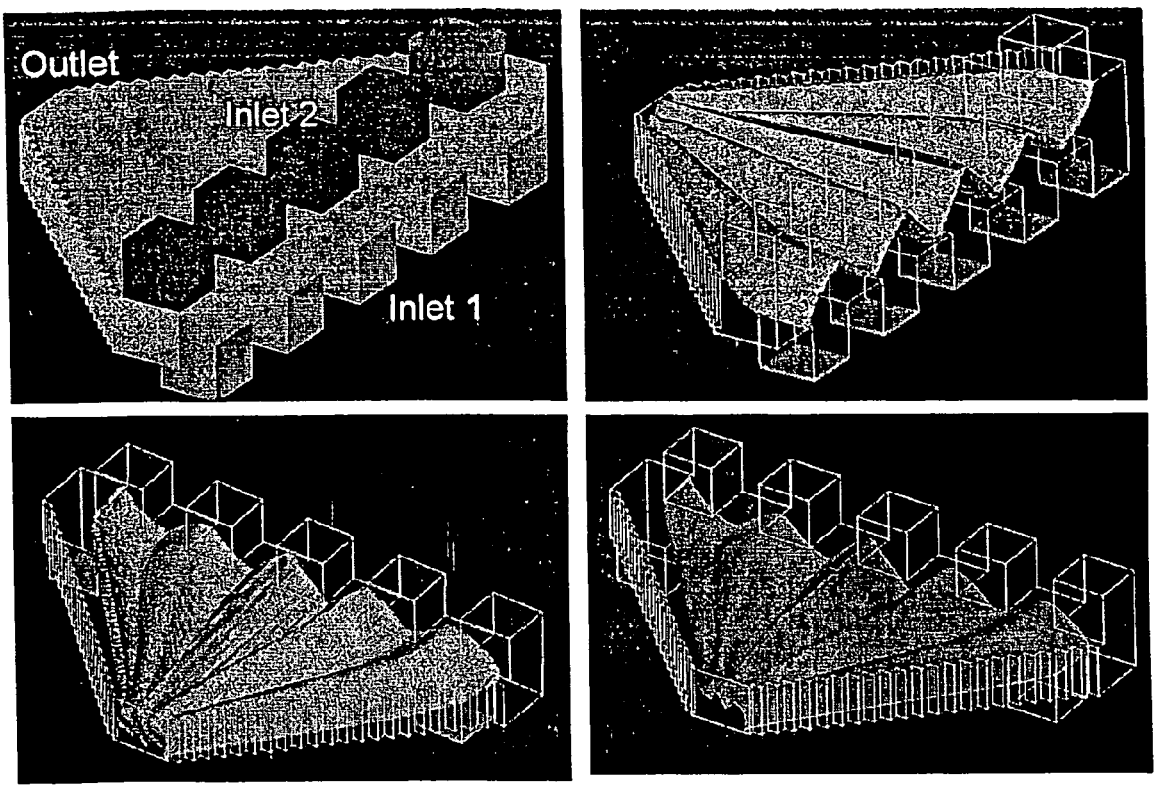
FIG. 33 shows an alternative embodiment of an arrangement of microfluidic structures in a single-channel, comb mixer.
Figure 34:
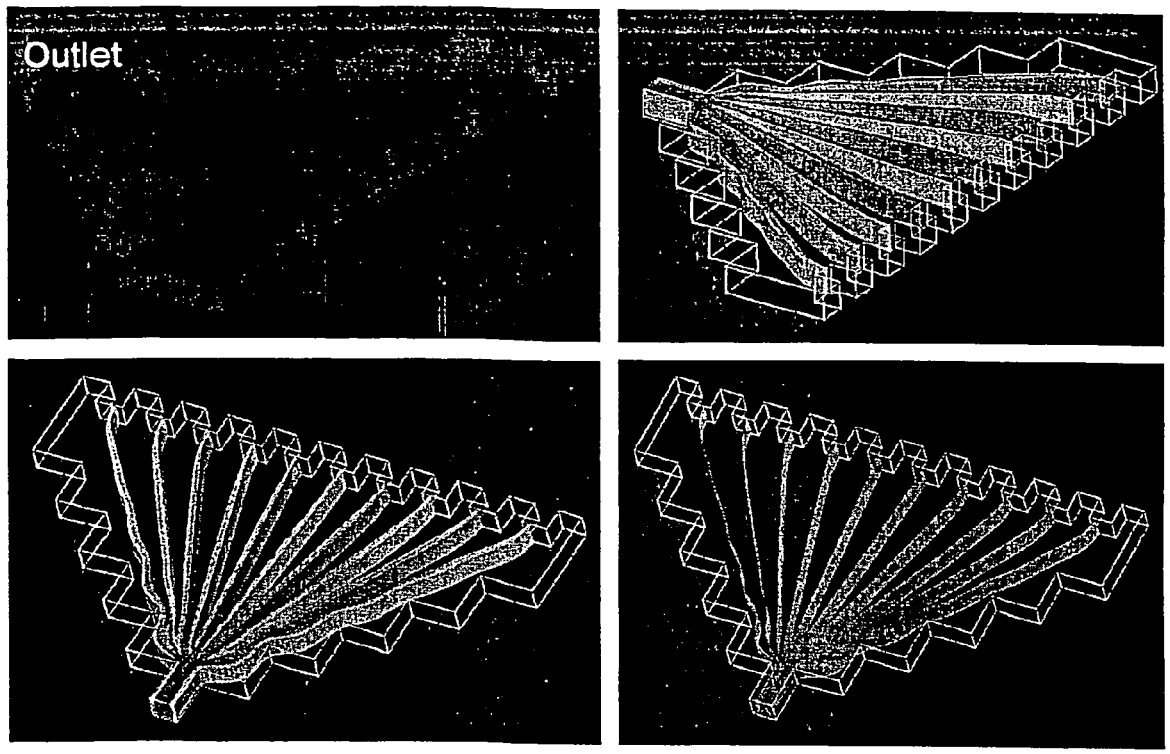
FIG. 34 shows an alternative embodiment of an arrangement of microfluidic structures in a single-channel, comb mixer.

FIG. 33 shows the structure of a top-bottom inlet design of the comb mixer, wherein each fluid enters through multiple, spaced inlet ports. Each of the ports for at least one fluid are on the top side of the device, while each of the ports for another fluid are located on the bottom side of the device. Each inlet port has cross-sectional dimensions of 50 µm by 50 µm. Ultimately, all of the fluid segments merge into a laminar flow field that enters the main channel. The main channel converges in one dimension in step-wise fashion, resulting in a triangular-shaped planar channel. FIG. 34 shows the structure of a flat comb mixer, wherein all of the input fluids enter in a single plane, rather than from the op or the bottom. In this case, multiple input ports are arranged in a linear array, with each fluid entering through alternating input ports. All of the input fluids merge in a laminar flow field that enters the main channel. As in the example in FIG. 33, the main channel converges in one dimension in step-wise fashion, resulting in a triangular-shaped planar channel.

It will be recognized by those with skill in the art that a plurality of such arrangements of microfluidic structures can be fabricated on a platform disk according to the invention, permitting parallel dilution series of a plurality of different samples to be performed simultaneously or on the same platform.

The following Examples are intended to further illustrate certain preferred embodiments of the invention and are not limiting in nature.

EXAMPLE 1

Simultaneous Enzyme Inhibition Assays

Figure 11:
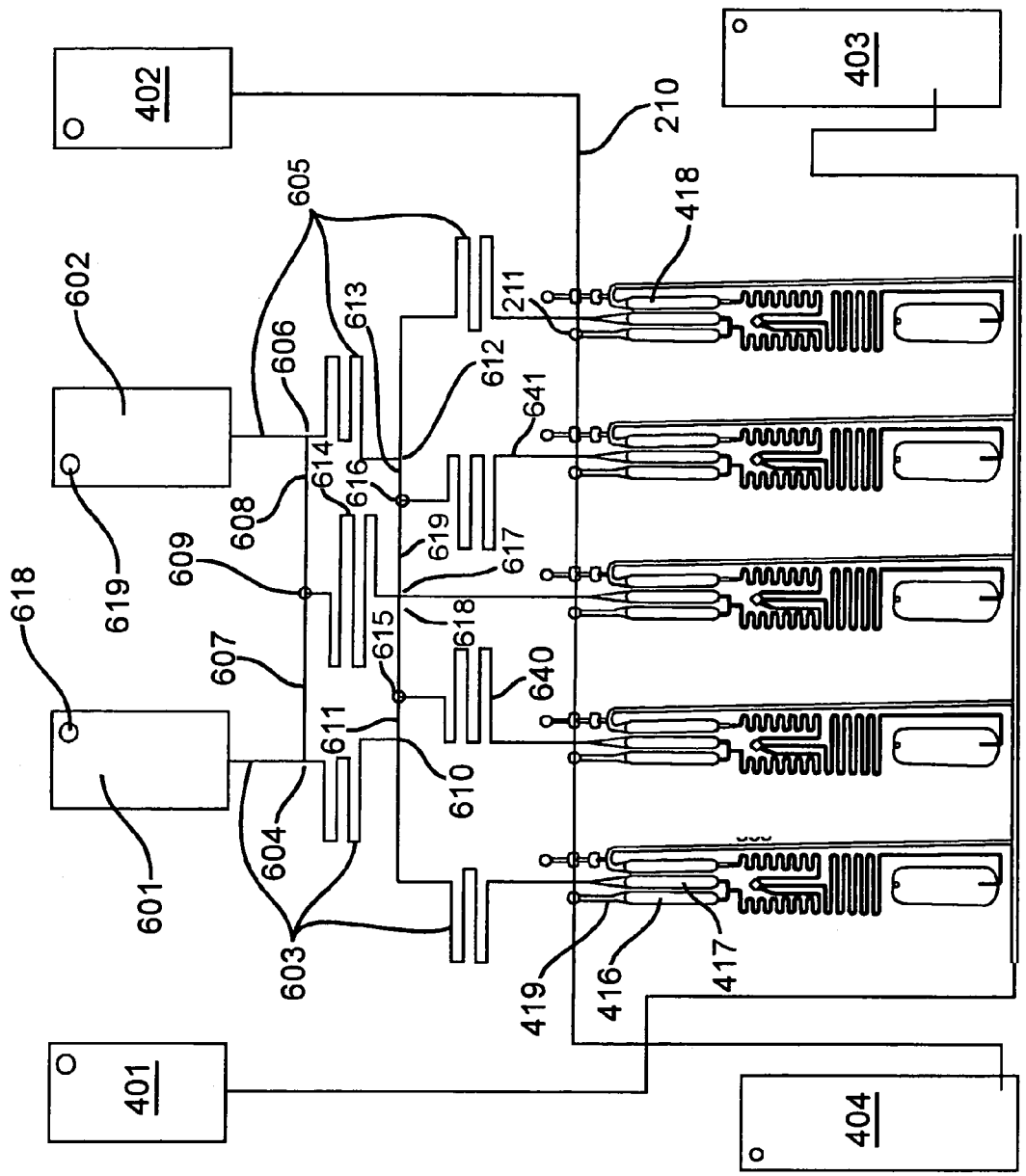
FIG. 11 illustrates a third alternative construction of the microsystems platform in which a series of mixtures of two reagents are delivered to the assay structures of the device.

A platform depicted in the FIG. 11 was used in this example. The platform of FIG. 11 is functionally identical to that of FIGS. 1-8, the only significant difference being that that of FIG. 11 is designed for the performance of 24 assays, while that of FIGS. 1-8 is designed for the performance of 96 assays.

The platform was prepared as follows. The microfluidic reservoir layer 201 was manufactured through machining of acrylic using computer/numerical code machining using a Light Machines VMC5000 milling machine running Light Machines "Benchman" software (Light Machines Corporation, Manchester, N.H.).

The sealing film of as shown in FIG. 3 was made by applying a double-sided tape to a thin sheet of heat-stabilized polyester (mylar). A section of mylar bonded to tape was cut from the combined sheet to the correct shape, leaving one adhesive face of the tape for application to the macrofluidic layer.

The microfluidics layer was manufactured as follows. A microfluidics structure such as the structure shown in FIGS. 5a through 5d was designed using in a computer aided design package such as AutoCAD (Autodesk, San Rafael Calif.) and Freehand (Macromedia Inc., San Francisco, Calif.). This design was converted into a photomask by printing at high resolution (3386 dpi) on a transparent plastic sheet. A 125-mm diameter silicon wafer was coated with a layer of negative photoresist (SU-8(50)) and spun on a spin-coater (Chemat Technology, Northridge, Calif.) at a speed sufficient (200 to 8000 rpm) to give a desired thickness between 5 μm and 500 μm. The silicon wafer was baked to have a smooth surface and then the photoresist partially cured. The silicon wafer was exposed to ultraviolet (UV) light using a conventional UV source and mask aligner. The photoresist was then developed in propylene glycol methyl ether acetate and non-crosslinked photoresist removed through washing in dichloromethane. The resulting relief was then passivated by exposure to a vapor of tridecafluoro- 1,1,2,2-tetrhydrooctyl-1-trichlorosilane and used as a mold for microfabrication (Duffy et al., 1998, *Anal. Chem.* 70: 4974-4984).

A 10:1 mixture of polydimethylsiloxane (PDMS) oligomer and crosslinking agent (Sylgard 184, Dow Corning) was poured onto the mold after degassing under vacuum. PDMS is a clear material; by adding 1 wt % liquid pigment (containing $TiO_2$), the disc was made white for reflectance optical measurements and black for fluorescence measurements. The poured elastomer was then cured at 65° C. for 1 hour. The resulting microfabricated PDMS part was peeled from the mold. The mold could then be re-used to fabricate additional copies of the microfluidics layer.

The microplatform was assembled in the following way. Sealing film with adhesive exposed was first applied to the upper surface of the macrofluidic layer so that it completely covered the holes and channels 207, 208, 211, 218. Final assembly was completed by forming a reversible, conforming seal between the PDMS microfluidics layer and the bottom surface of the microfluidic reservoir layer 201 made through simple physical contact of the two components. This seal is based on physical adhesion forces alone—van der Waals attraction forces and potentially static electrical charge present on the surfaces—and was sufficient to seal the disc against leakage due to the centripetally-induced pressures used.

The platform shown in FIG. 11 and prepared as described herein was used to perform simultaneously and in parallel 24 enzyme inhibition assays. Fluids were deposited in the reservoirs formed in reservoir layer 201 when reservoir layer is mated or bonded with microfluidics layer 500. Platform 100 is then rotated using a rotational profile designed to drive fluids through the channels within the macrofluidic disc 201 and the microfluidic disc 500.

The platform shown in FIG. 11 possesses the same features as that shown in FIGS. 1 through 6, and reference to features will be made those on the latter figures. It was used to perform 24 simultaneous enzyme inhibition assays as model homogeneous assays. In an enzyme inhibition assay, the effect of a compound present in a first fluid ("A") upon the capacity of an enzyme present in a second fluid (fluid "B") to catalyze a reaction, typically of a substrate in a third fluid ("C") is determined. The reaction was chosen to give a change in a readily-measured parameter of the fluid, such as its optical density, or to produce a fluorescent moiety. When no inhibitor was present in fluid A, mixing solution A with enzyme solutions had no effect: The enzyme activity detected in this assay was the maximum detected and provided the largest change in the measured parameter. However, if an inhibitor was present in fluid A, mixing fluid A with fluid B will, after a sufficient time resulted in a chemical reaction or other change induced by the inhibitor in most or all of the enzyme molecules, rendering them incapable of catalyzing the desired reaction. If this solution was mixed with the substrate solution, little or no change in the measured parameter was seen.

The system chosen to model homogeneous assays consisted of theophylline as inhibitor, alkaline phosphatase as the enzyme, and p-nitrophenol phosphate (PNPP) as the substrate. In the presence of alkaline phosphatase, PNPP, which is colorless, is converted to p-nitrophenol (PNP), which absorbs in the blue and therefore appears yellow. Theophylline was used in concentrations of 0.01 mM to 100 mM to provide a standard dose-response curve in the inhibitor. Alkaline phosphatase was used in a 1 mg/mL solution. PNPP was used as a 0.5 mM solution. All solutions were made in a buffer of 0.1 M glycine and 0.5 mM $MgCl_2$ in deionized water.

The dimensions of the platform used for these assays were as follows. The overall platform diameter was 12 cm. The macrofluidic disc was about 1.6 mm thick. The diameter of the sample entry ports through-holes 204 was 0.5 mm; the depression 203 was conical, with an outer diameter of 2 mm and a depth of 1 mm, allowing the cones to "guide" the placement of pipette tips when loaded manually. The common reagent entry ports consisted here of only through holes 215 and 217, also of diameter 0.5 mm. The air ports 205 and 206 were also 0.5 mm in diameter. The reagent manifold through-hole 207 was also 0.5 mm in diameter, and the exit channel 208 was of larger diameter and depth of 0.43 mm.

The exit channel narrowed to join the channel 209 of width 0.45 mm. The manifold 210 was also 0.43 mm deep and 0.45 mm wide. The vias 211 were 0.45 mm in diameter and penetrated through the macrofluidic disc from the top surface to the bottom surface. The terminal via 218 had a diameter of 0.53 mm and penetrated to the bottom surface of the layer.

The dimensions of the features on the lower face of the macrofluidic disc were as follows. The common reagent reservoirs 401 and 402 had a depth of 1.14 mm. The radial positions of the ends of these reservoirs most proximal to the center of the disc were 1.59 cm and that of the ends most distal from the center of the disc were 3.4 cm. The volume allowable in reagent reservoir 402 was 1 mL, and that of reservoir 401 was 1 mL. Entry passageway 406 was 0.25 mm deep and 0.25 mm wide. Channel 408 was 0.25 mm wide×0.25 mm deep, as was manifold 409. Overflow reservoir 403, corresponding to reagent reservoir 402, had an outer radius of about 5.6 cm and an inner radius of about 4.3 cm and a depth of 1.5 mm. The angle subtended by the reservoir was chosen to accommodate a volume of 30 microliters. Similarly, overflow reservoir 404, corresponding to reagent reservoir 401, had an outer radius of about 5.6 cm and an inner radius of about 4.3 cm and a depth of 1.5 mm. The angle subtended by the reservoir was chosen such that it could accommodate a volume of 30 microliters. Air holes 410 had a diameter of 0.5 mm.

Referring to FIG. 4d, the features of the individual assay structures were as follows. Entry channels 411 were 0.25 mm wide×0.25 mm deep; their lengths varied according to the relative positions of the reservoir 417 and entry port 204 that each channel connected, from about 12 mm to about 27 mm. Channel 411 preferably opens at its connection to reservoir 417 such that acute angles are not presented within the plane of the disc that might impede fluid flow. The inner radii of reservoirs 416, 417, and 418 were about 4.1 cm and outer of reservoirs 416, 417, and 418 were about 4.5 cm. Both inner and outer ends of the reservoirs were rounded with radii of 0.5 m to prevent fluid from both "stopping" at the inner end during loading due to capillary forces and being retained as the reservoirs emptied. Reservoirs 416, 417, and 418 were about 0.57 mm, 0.57 mm, and 1.14 mm deep, respectively. Each reservoir was 0.6 mm in width. The lengths, depths, and widths of the reservoirs were chosen such that the volumes contained within 416 and 417 were 0.91 microliters while that contained with aliquotted reagent reservoir 418 was twice that volume, 1.82 microliters. Detection reservoirs 420 were constructed of optically-transparent material and had an outer radius of about 5.7 cm and an inner radius of about 5.2 cm, were 0.7 mm deep, and had a subtended angle of 3.2° and were thus designed to accommodate the combined volumes of reservoirs 416, 417, and 418 (approximately 3.6 microliters). Distribution manifold 409 is connected to aliquotted reagent reservoir 418 via a filling channel 415 which as 0.25 mm wide×0.25 mm deep; the end of 415 was also enlarged at its connection to aliquotted reagent reservoir 418. Capillary channel 414 was 0.13 mm wide×0.13 mm deep. The capillary junctions 413 were 0.25 mm deep×0.5 mm wide; they were formed so that the opening of 414 into 414 formed a backward angle of 45°, thus increasing the capillary stopping power of the junction. The connection to reservoir 416 is via passageway 419, which was about 0.25 mm deep and widened by 0.25 mm wide to 0.6 mm wide at its joining with 416.

The microfluidics layer 500 was also 12 cm in diameter and had a thickness between 1 and 2 mm (although the thickness is not important) and was composed of white PDMS. The depth of all microfluidic structures (that was determined by the height of the SU-8 relief) was 100 µm. The width of the entrance to the mixing channels, 505, 506, and 512, was 200 µm. The channels narrowed to 100 µm before reaching the capillary junction at 508. The width of the junction 508 was 120 µm. Similarly, the entrance 512 narrowed to 100 µm prior to the junction 513 that was 200 µm. The widths of channels 509 and 514 was 100 µm. The lengths of the mixing channels was chosen to provide sufficient time for mixing via diffusion with liquids of moderate diffusion constant ($5 \times 10^{-6}$ cm$^2$/s) as fluids are pumped through them under the influence of centripetal acceleration. The lengths of channels 509 and 514 was about 17 mm. These channels narrowed to 50 µm at 510 and 515 before joining the junction 511, which was about 0.4 mm square. Channel 516 was 100 µm wide and about 38 mm long. These dimensions resulted in the fluids taking $\geq 2$ sec to transit the mixing microchannels.

Also on the microfluidic layer are the overflow structures 503 and 504. The entry 518 was 0.4 mm×1.8 mm, while the capillary passageway 519 was 120 µm wide. Enlargement 520 was about 200 µm wide by 200 µm long, and 521 was also 100 µm long.

The assays were run as follows. 1 µL aliquots of theophylline solutions having the concentrations set forth above were loaded into entry ports 203+204 using a pipette. Alkaline phosphatase was loaded into reservoir 402 through entry port 217, and PNPP solution was loaded into reservoir 401 through entry port 215. The platform was placed on the spindle of an instrument containing a diffuse reflectance optical head capable of three-color measurements. FIGS. 7 and 8 illustrate the sequence of fluid flows in the vicinity of the reservoirs of microfluidic assay elements. The platform was first rotated at 300 rpm for 30 seconds. At this rotation rate, the theophylline solutions were driven completely through channels 411 into the reservoirs 417, where it was retained by capillary junctions 508. Also at this rotation rate, the alkaline phosphatase solutions were driven through hole 207 into manifold 210. As the alkaline phosphatase solution traveled 210, it flowed through the vias 211 into passageways 419 and finally reservoirs 416, where it was retained by capillary junctions 508. Also at this rotation rate, the PNPP solution was driven through channel 408 and manifold 409 to the fill channels 415. The PNPP solution was driven through 414 to the aliquotted reagent reservoirs 418; PNPP solution also entered capillary 414 and was stopped at capillary junction 413 and at capillary junction 513. The rotational rate was then increased to 500 rpm. At this speed, the overflow capillary valves formed by 519 and 520 on the overflow structures released. The alkaline phosphatase solution in manifold 210 then flowed into the overflow reservoir 403, leaving behind solution in the reservoirs 416. At the same time, the draining of excess PNPP solution into the overflow reservoir 402 exerted an inward "pull" on the solution at the capillary junctions 413. The tension in the fluid in channel 415 so created was relieved through the introduction of air via channel 413; this effectively separated the draining PNPP solution in 415+ 409 from the solution in the aliquotted reagent reservoirs 418. The speed was increased to 600 rpm, at which point the capillary junctions at 508 and 513 allowed fluid to flow. The fluids from reservoirs 505 and 506 flow through channel 509 and were halted at the junction 510; similarly, the fluid flowing through 514 was halted at the junction 515. At 700 RPM, the capillary junctions at 511 allowed the fluids to flow. The mixed fluids were then pumped into the detection reservoir 420. In the case of the junctions 507 and 511, whichever fluid flows first is forced to wet the exit capillary of the other fluid in the capillary junction, thereby inducing it to flow as well.

An important feature of mixing in the device is made possible through the narrowness of microchannels 509, 514, and 516. The resistance to flow due to rotationally-induced pressure of a channel that is denoted by $R_H$ is given by $$Q = \frac{P}{R_H}$$

$$R_H = C \frac{l}{(d^H)^4}$$

where Q is a flow-rate, P is the induced pressure, C is a constant, l is the length of the channel through which the fluid flows and $d^H$ is the hydraulic diameter. Because the diameter of microchannels 509, 514, and 516 are much narrower than that of the reservoirs 416, 417, and 418, resistance to flow is dominated by the microchannels, and hence the pressure drop across the flowing fluid is sustained almost exclusively over the length of the mixing microchannels. This insures that the fluids flowing from reagent reservoirs into mixing channels do so in a strict, known ratio. In particular, assume that fluid begins to flow from one reservoir into the mixing channel at a rate faster than the fluid flows from the other reservoir. The resulting pressure drop from the meniscus of the fluid at the inner edge of the reservoir to the point where the fluids mix for the fluid that flowed faster will be less than that of the other fluid, because the rotationally-induced pressure is proportional to the radial extent of the fluid (ΔR discussed earlier). Because a higher pressure now exists across the fluid that moved more slowly, it is induced to flow more rapidly. This process of feedback provides a pressure-equalization phenomenon that results in the inner meniscuses of fluids in reservoirs 416, 417, and 418 progressing outward at the same radial velocity (same distance in the radial direction per unit time). As a result, the ratio of the alkaline phosphatase and theophylline flow-rates as a function of time in mixing microchannel 509 is given exactly by where $A_A$ and $B_B$ are the cross-sectional area of the reservoirs 416 and 417 as a function of time, or alternately, radial position of the meniscus as fluid is removed from the reservoirs. If it was desired that the ratio of flows is constant (as was the case here), it was sufficient to maintain a constant ratio of cross-sectional areas as a function of radial position. Note that this does not imply that the cross sections are constant, just that their ratio is. The ratio expressed in the equation can be manipulated by altering the ratio of cross-sectional areas of the reservoirs, as disclosed more fully in co-owned U.S. Pat. No. 6,063,589, issued May 16, 2000 and incorporated by reference.

This equation and analysis also accurately describes the significance of the ratio of the three fluids in mixing microchannel 516. Because microchannel 509 and 516 are long and the flow rates can be controlled by rotational rate, the co-flowing streams are present in those channels for a time sufficient enough for diffusion across the interface between these streams to effect complete mixing of the solutions.

After fluid was delivered to the detection reservoirs 420, reflectance optics was used to measure the reflected radiation at an off-specular (diffuse) angle at two wavelengths, 430 nm (absorbing for the expected reaction product, PNP) and 630 nm. As there is no absorbance from reaction product PNP at 630 nm, this wavelength can be used to correct for optical imperfections in the platform, stray scattering, or unintended air bubbles in the optically-transparent chamber. The optical system also advantageously contained a beam-splitter that sent a fraction of the incident light to a reference photodiode. Two detectors used in this optics system were the assay detector, which measured diffusely-reflected light; and the reference detector, which measured a fraction of the incident light. Measurements at each detector were made when both the 430 nm and 630 nm light sources were active as well as when they were "dark" or off. The measured voltages were thus:

$V_D^D$ dark measurement in assay detector $V_R^D$ dark measurement in reference detector $V_D^1$ measurement at absorbing wavelength $\lambda_1$ (430 nm) in assay detector $V_D^2$ measurement at non-absorbing wavelength in $\lambda_2$ (660 nm) assay detector $V_R^1$ measurement in reference detector at absorbing wavelength $\lambda_1$ (430 nm)

$V_R^2$ measurement in reference detector at non-absorbing wavelength $\lambda_2$ (660 nm)

The absorbance at 430 nm is calculated from $$K = \frac{\left(\frac{V_D^1 - V_D^D}{V_R^1 - V_R^D}\right)}{\left(\frac{V_D^2 - V_D^D}{V_R^2 - V_R^D}\right)}$$

$$A = -\log(K) \propto c_{PNP}$$

Here, $C_{PNP}$ is the concentration of yellow product, p-nitrophenol; this concentration is inversely related to the concentration of theophylline in the initial solution.

Figure 12:
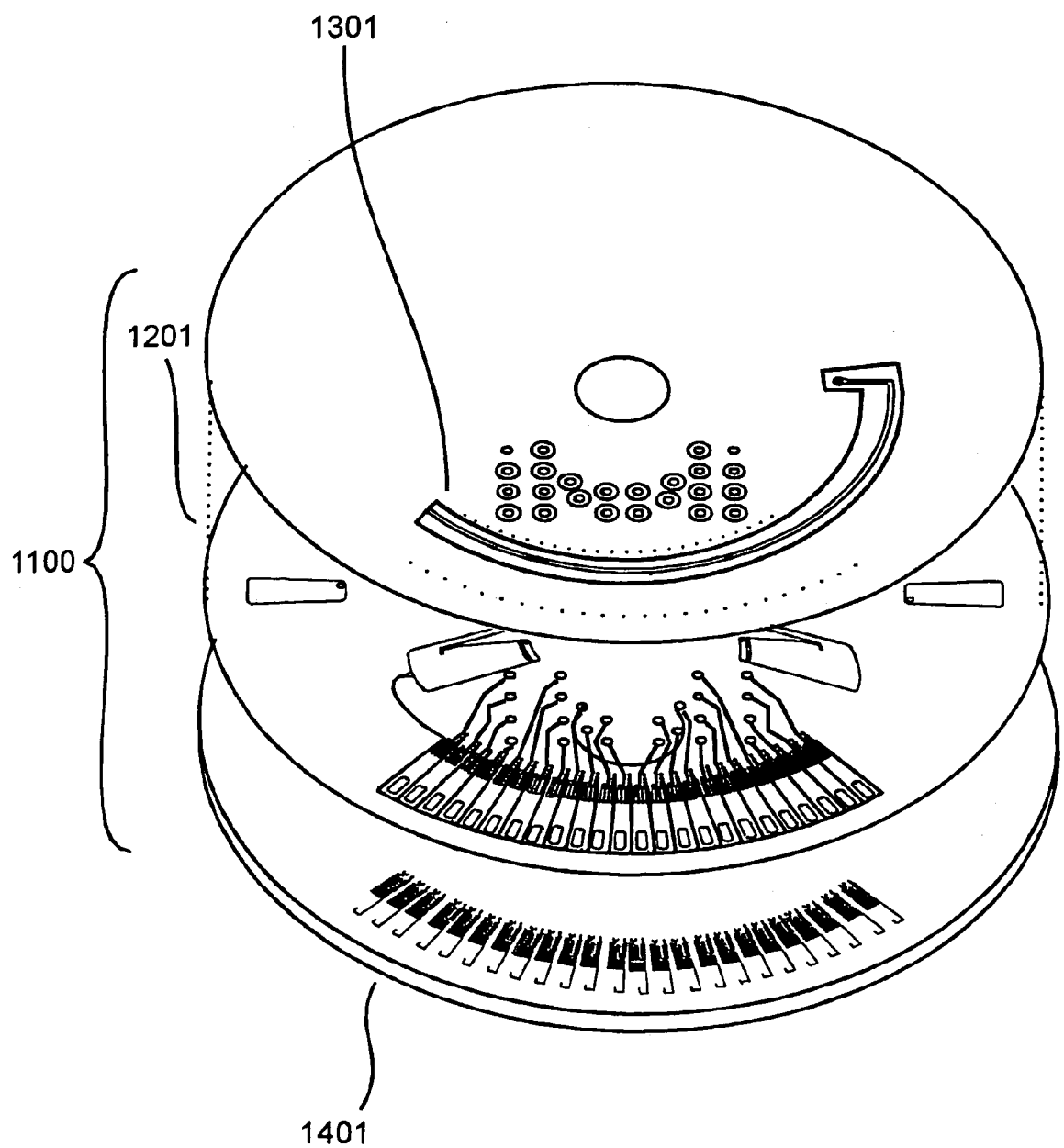
FIG. 12 shows a device developed for the performance of 24 parallel assays.
Figure 13:
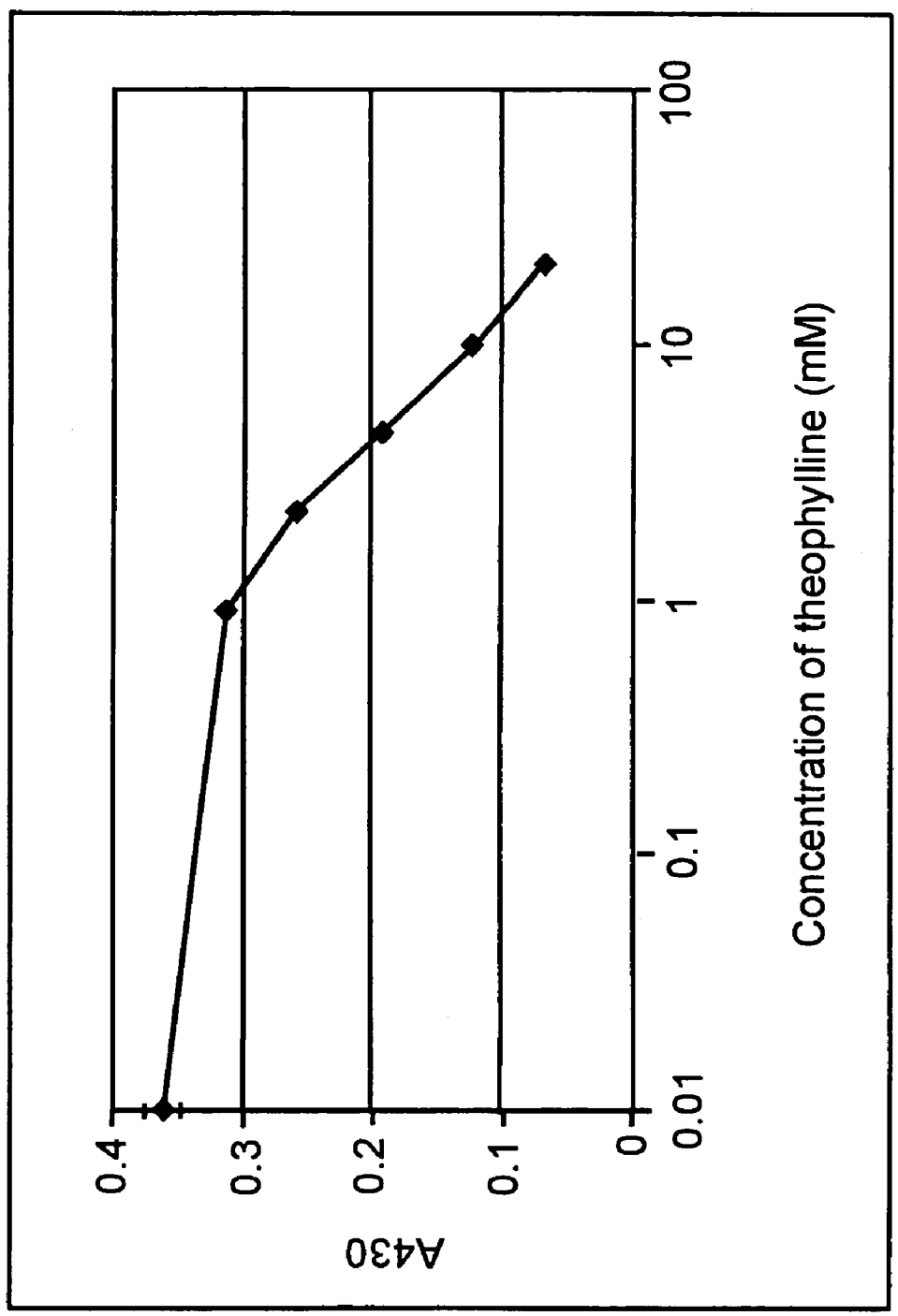
FIG. 13 shows a dose-response curve illustrating enzymatic activity as a function of inhibitor concentration for enzymatic inhibition assays performed with the devices of the invention, as disclosed in Example 1 and illustrated in FIG. 12.
Figure 14A:
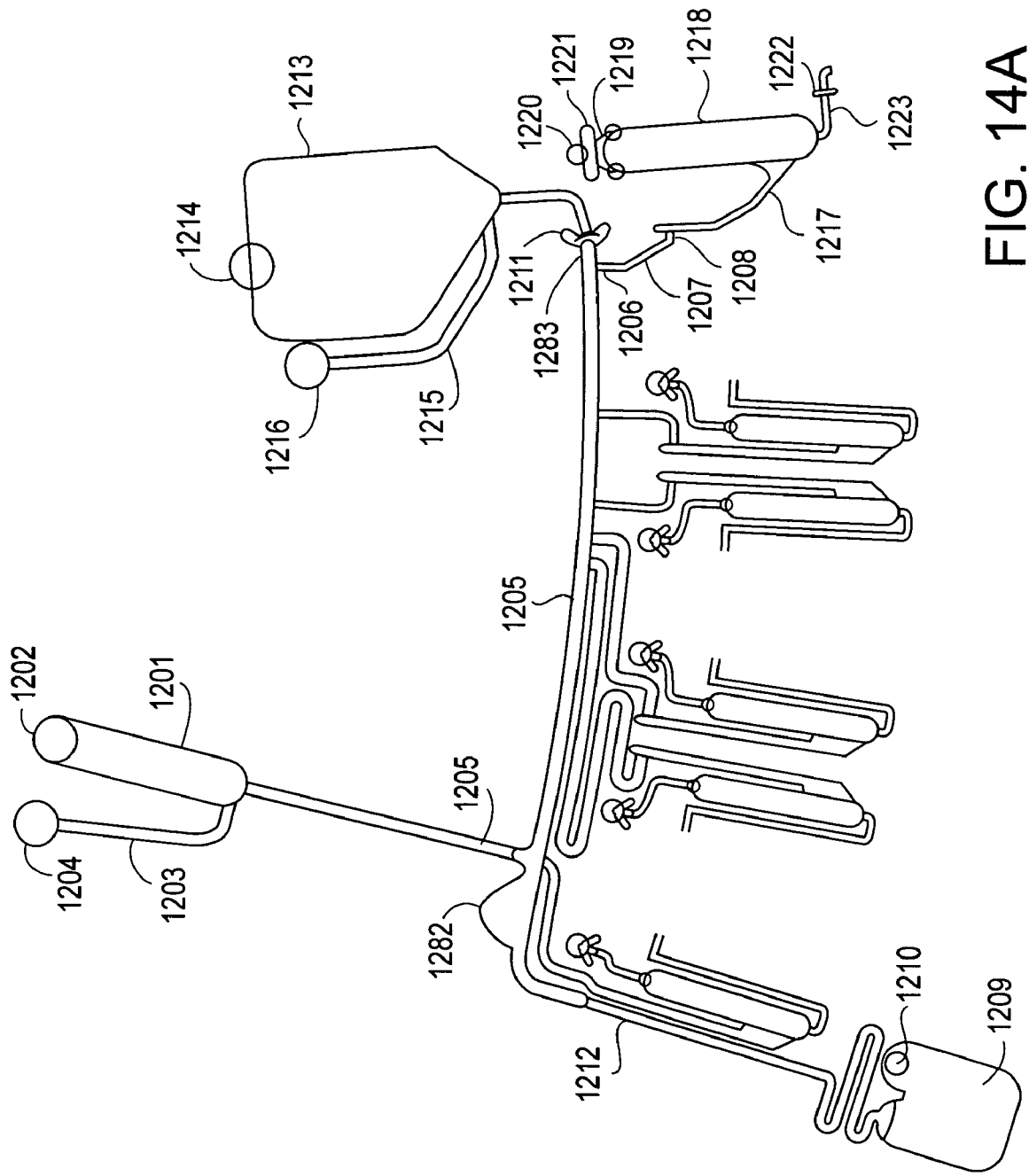
FIGS. 14A through 14I shows an arrangement of microfluidics structures on a disc of the invention for performing dilution of a biological sample (e.g., a drug).
Figure 14B:
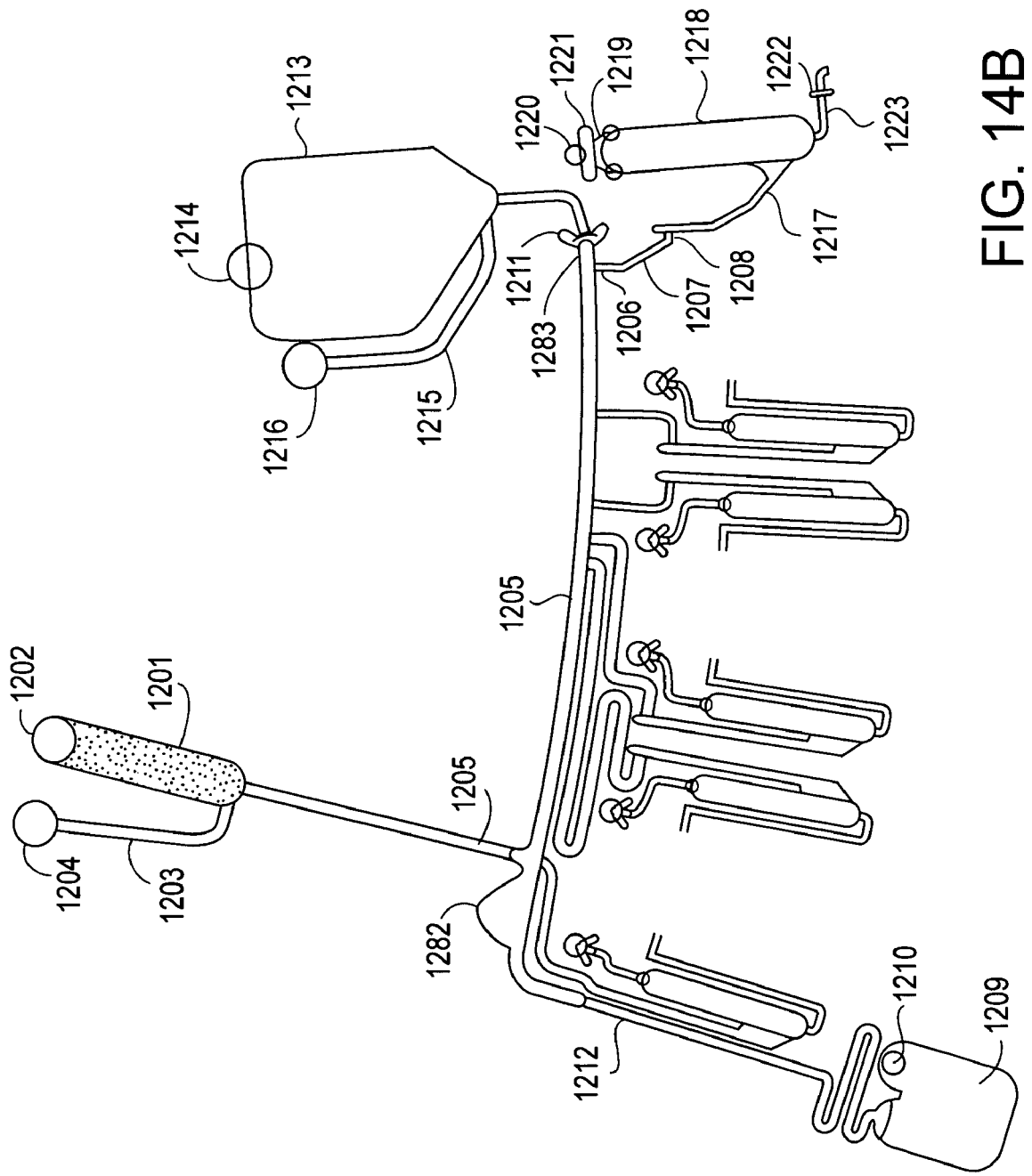
Figure 14C:
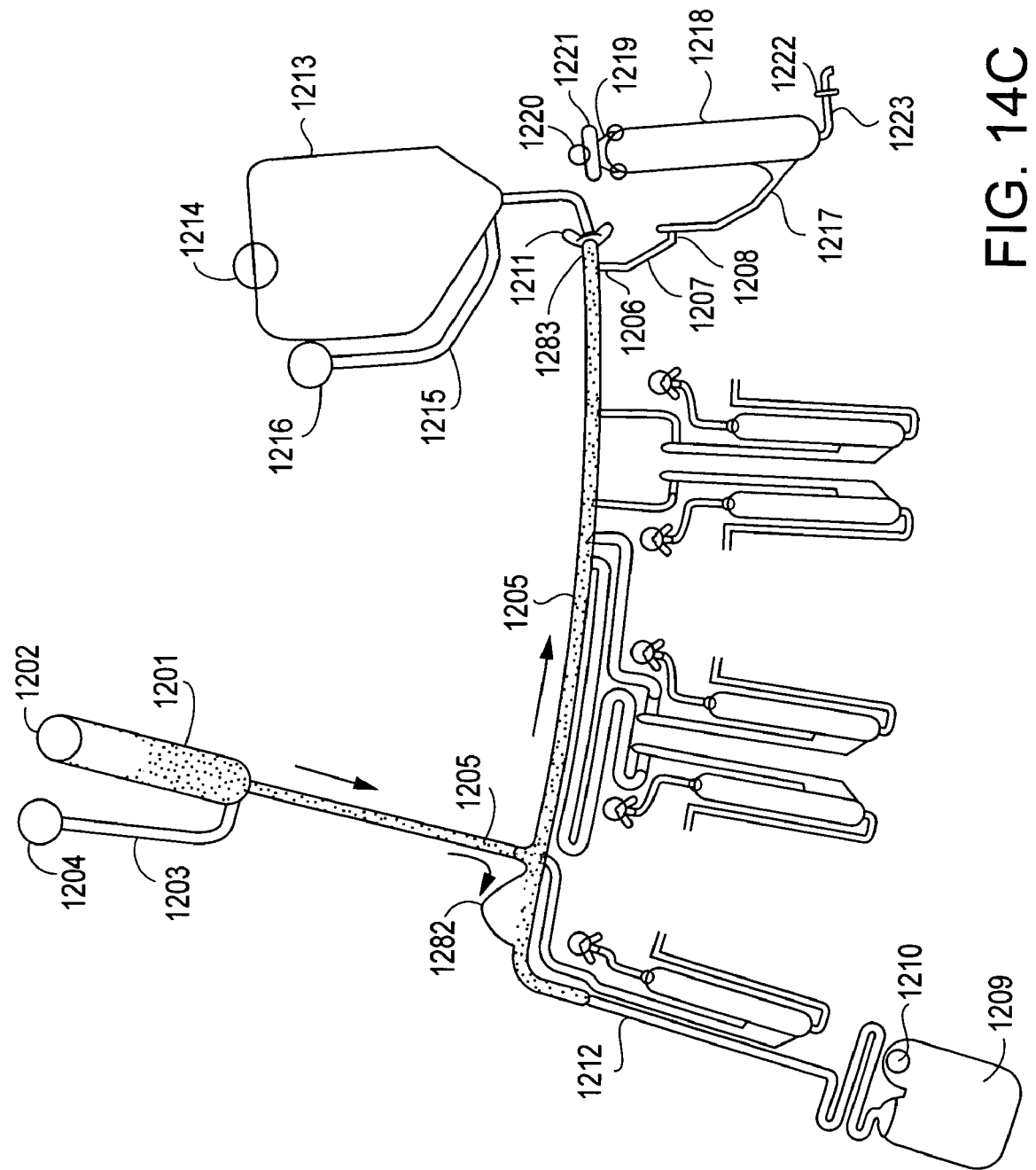
Figure 14D:
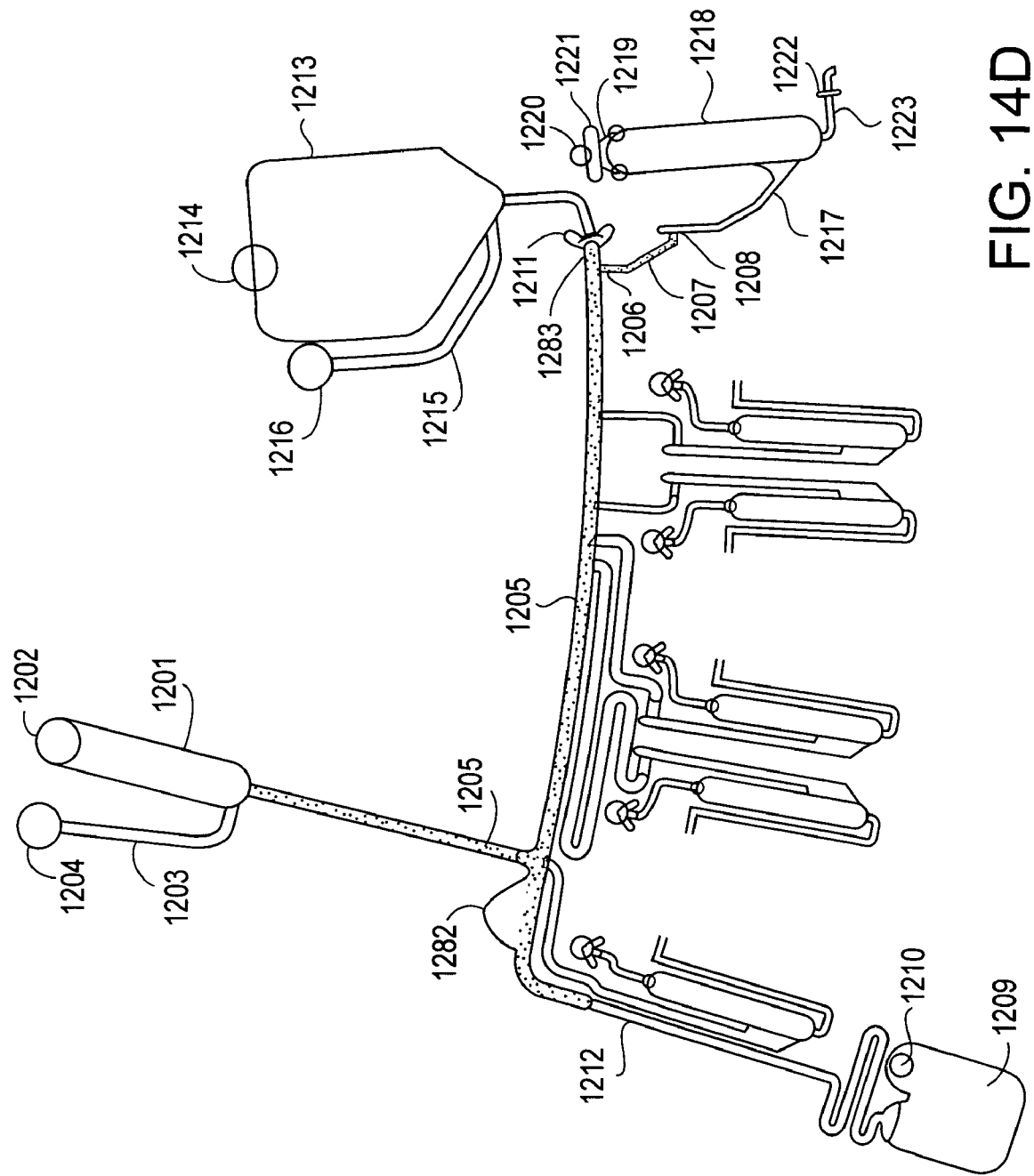
Figure 14E:
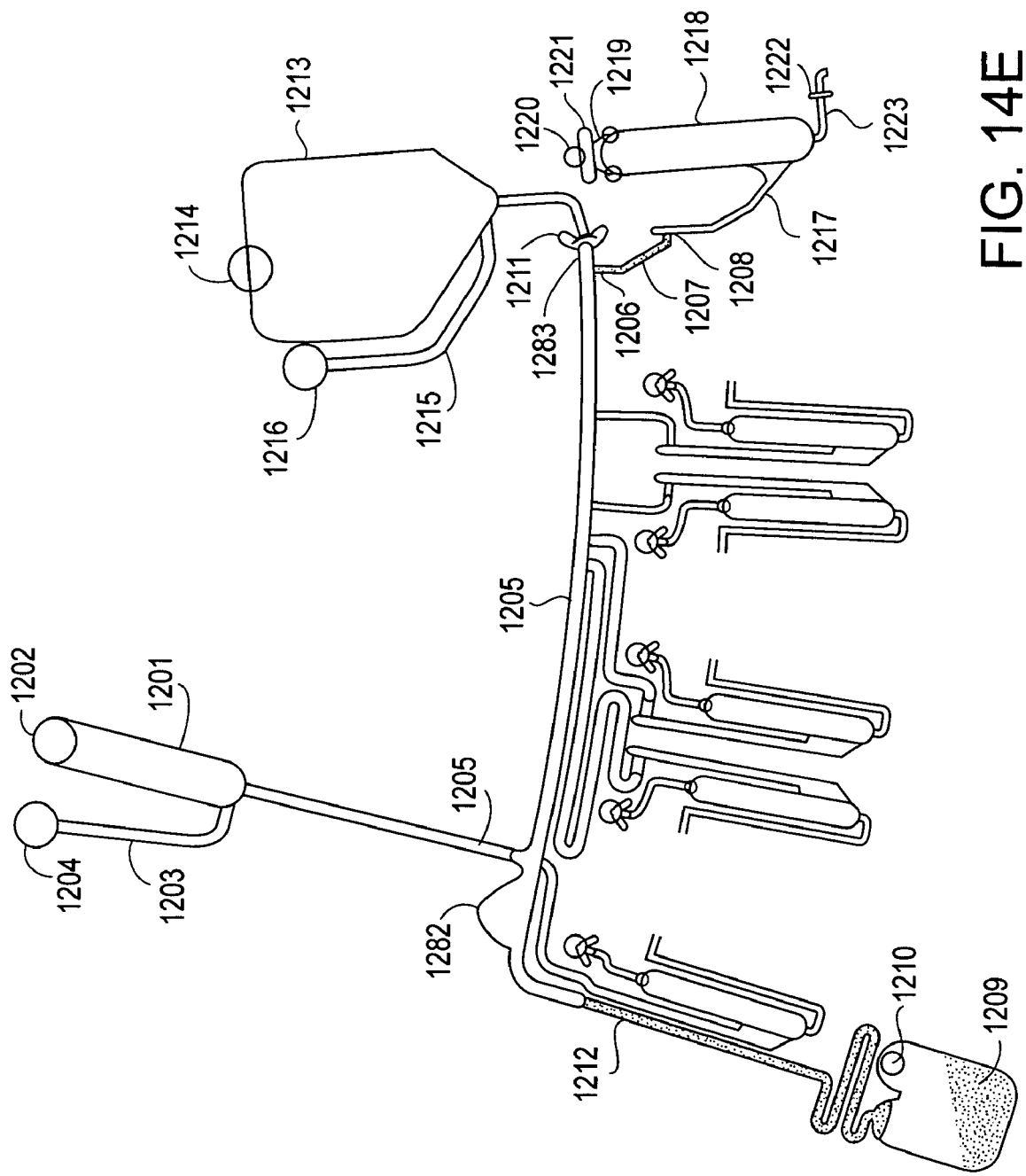
Figure 14F:
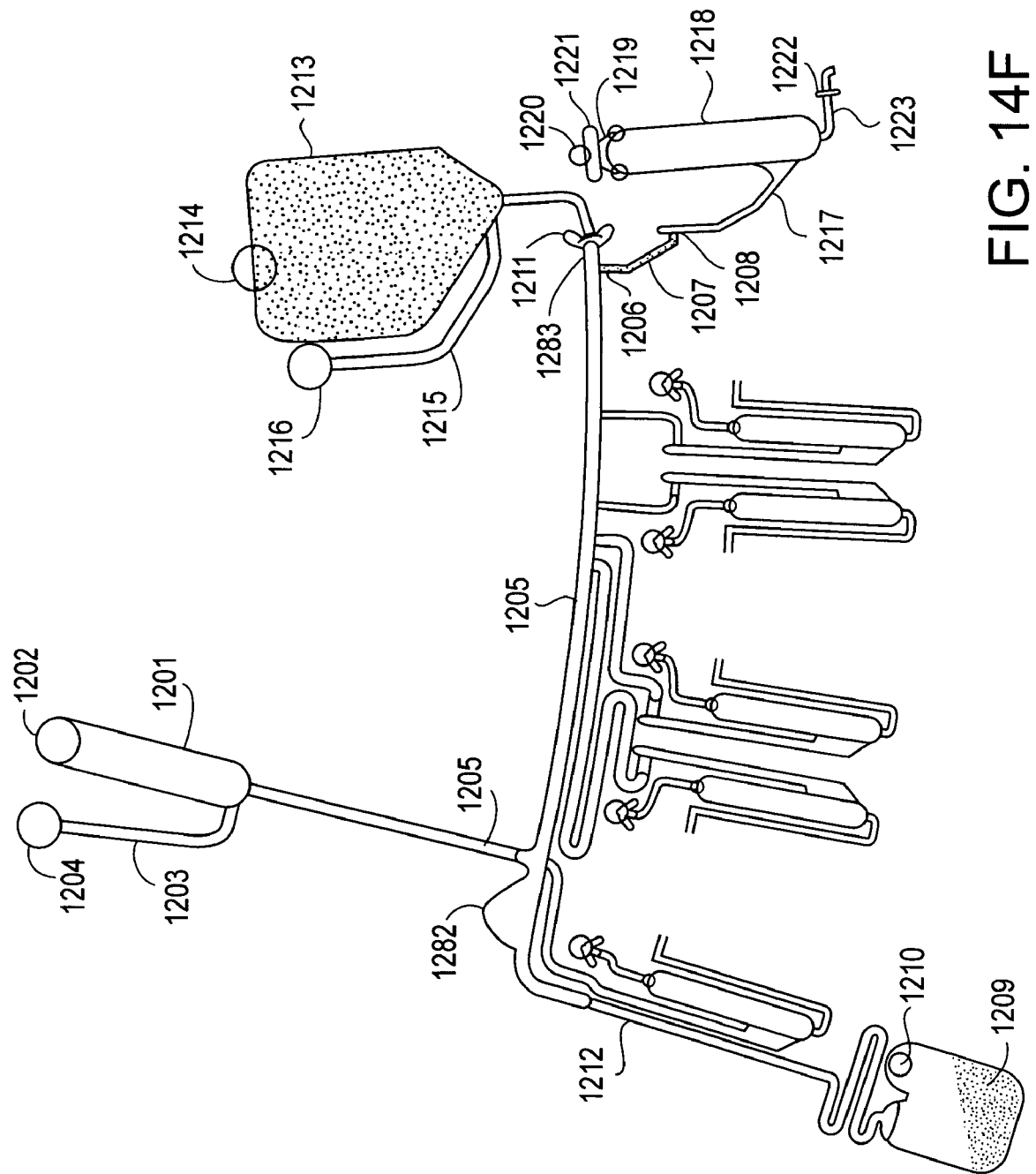
Figure 14G:
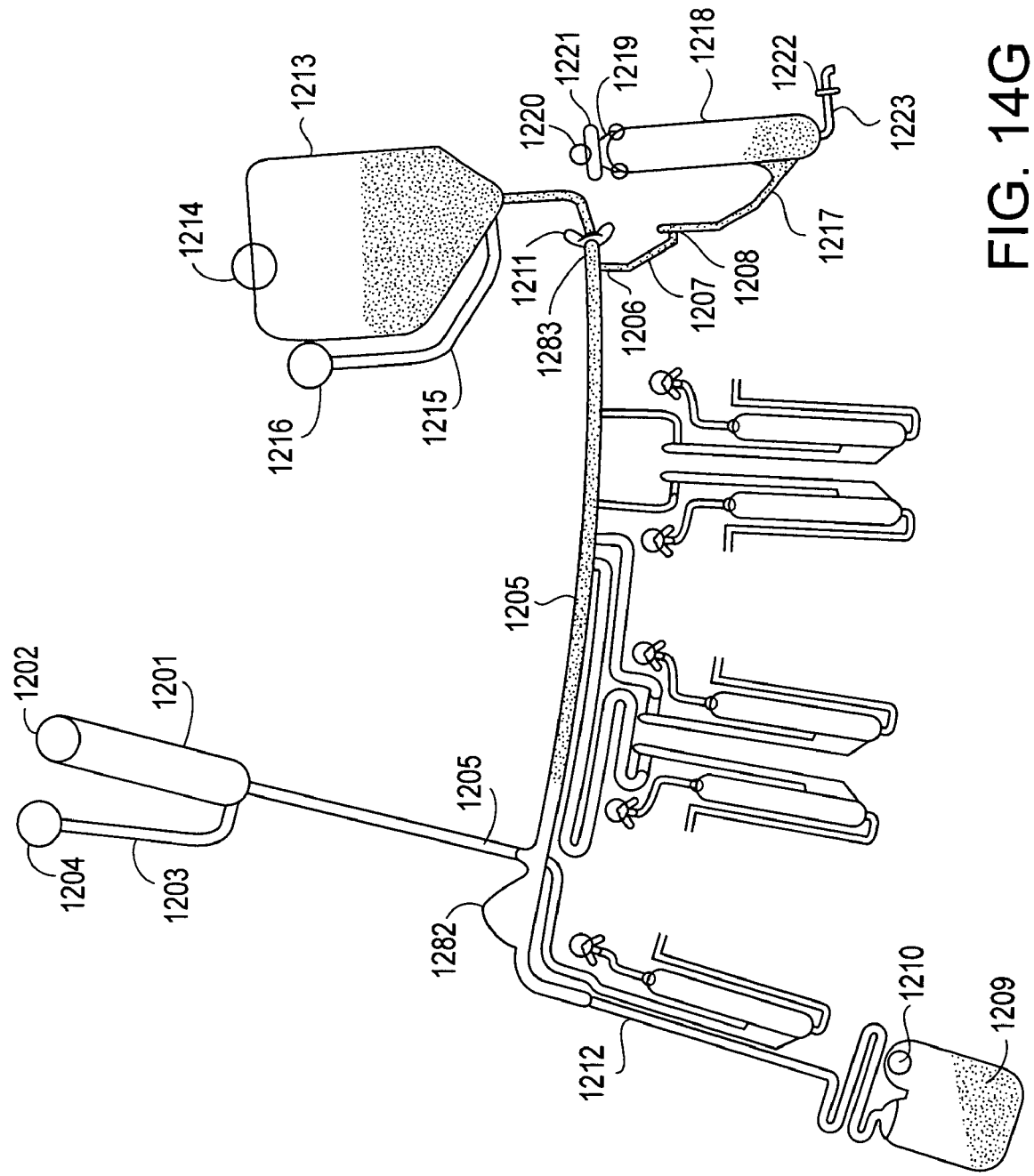
Figure 14H:
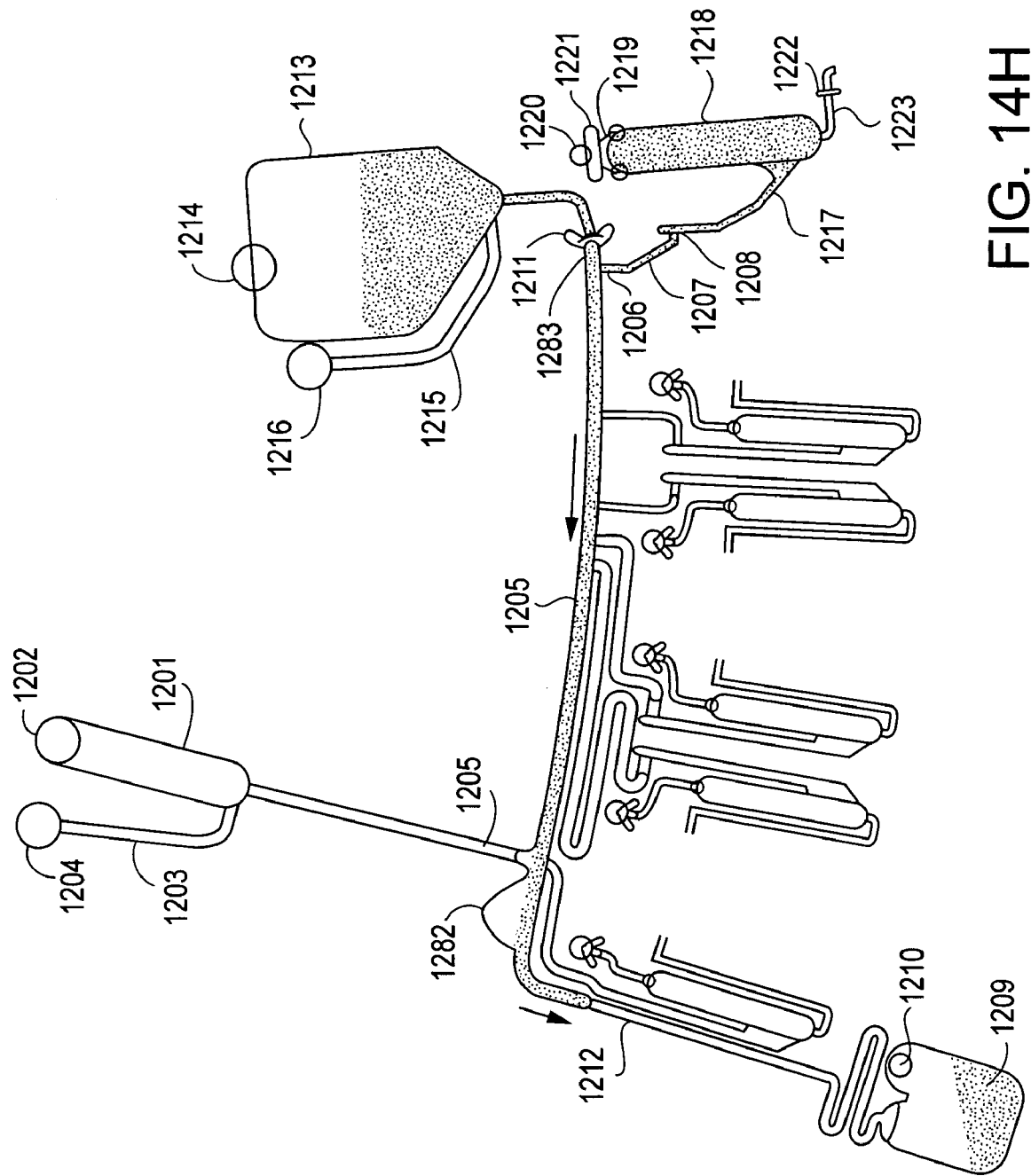
Figure 14I:
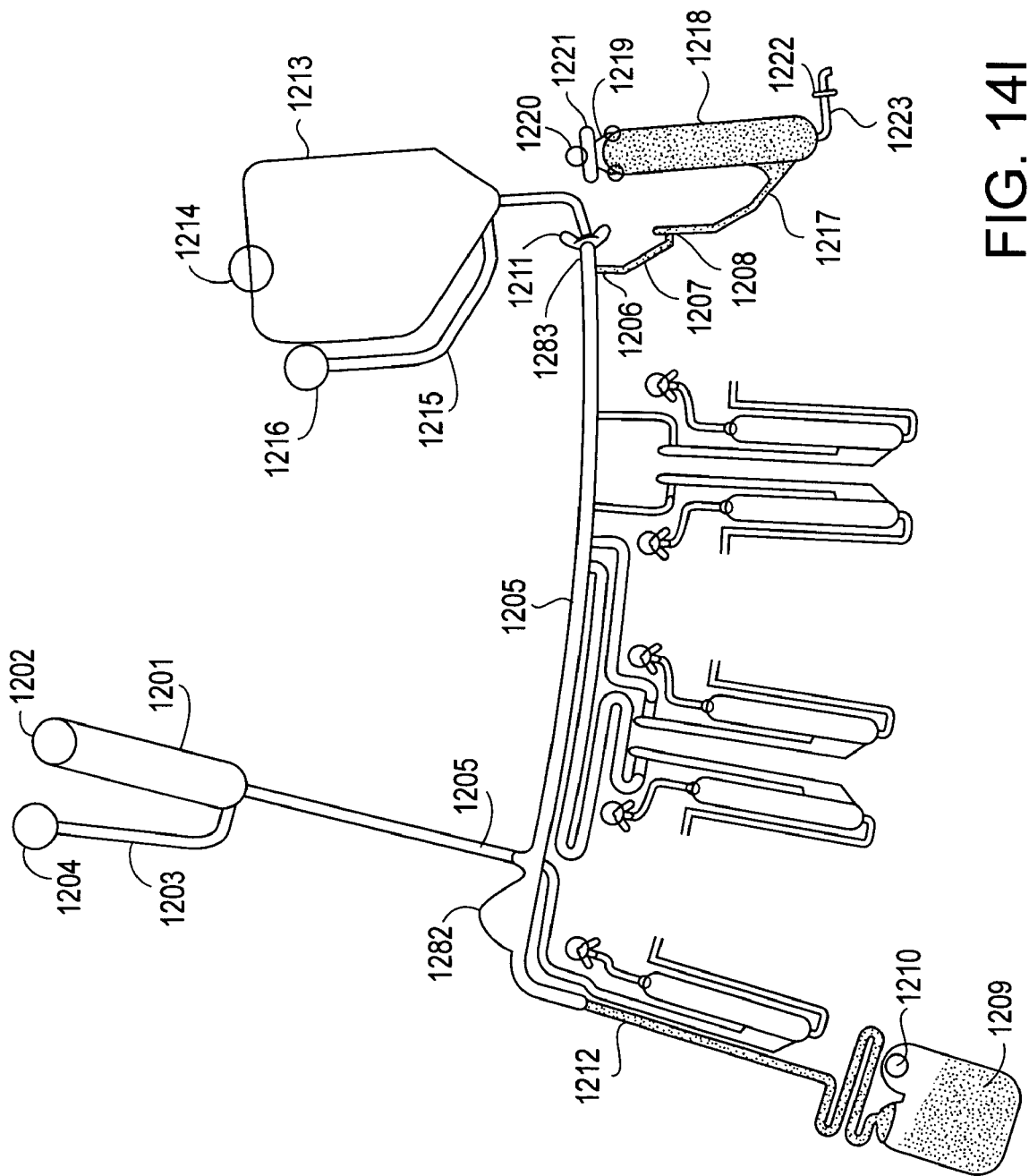

Data was collected continuously as the platform was rotated at 60 or 100 rpm. Because data can be taken continuously, the kinetics of the chemical reactions could be observed. FIG. 12 shows data for 24 assays run simultaneously on the platform, representing four-fold replicates for each of six theophylline concentrations ranging from 0 to 10 mM. The data are consistent with those generated on the laboratory bench using absorbance and that contained in co-owned and co-pending U.S. application Ser. No. 09/595,239, filed Jun. 16, 2000, incorporated by reference herein.

These results demonstrated that microplatform systems according to the invention can be used as a substitute for conventional 96-well microtiter plates for performing enzyme assays to determine enzymatic activity thereof.

EXAMPLE 2

Dilution Methods

A microsystem platform as shown in FIG. 17 was used to dilute a fluorescein-containing sample. This test was performed in two stages. First 1 mM fluorescein in DMSO was used to assess the performance of the first stage. Next 20 mM fluorescein in DMSO was used to assess the performance from the 4$^{th}$ dilution to the 9$^{th}$. The 20 mM fluorescein experiments were necessary to resolve the concentrations at the higher dilution range, which were not detectable using 1 mM fluorescein.

Meter chamber and intermediate cuvette volumes as well as theoretical dilution ratios for 1$^{st}$ stage dilution structures are shown in Table 1.

TABLE I

1st Stage characteristics

|  | Non-metered | 1st Dilution | 2nd Dilution | 3rd Dilution | 4th Dilution | 5th Dilution/Reservoir |
|---|---|---|---|---|---|---|
| Meter (μl) | 0.0 | 0.6357 | 0.2147 | 0.0671 | 0.0210 | 0.0153 |
| Meter Dimensions L × W × D (μm) |  | 10888 × 200 × 288 | 3926 × 200 × 261 | 1582 × 200 × 190 | 1847 × 127 × 85 | 1652 × 127 × 71.5 |
| Intermediate (μl)* | 2.0 | 1.3687 | 1.7911 | 1.9364 | 1.9844 | 5.1439 |
| Theoretical Dilution Ratio | 0.0 | $3.17 \cdot 10^{-1}$ | $1.07 \cdot 10^{-1}$ | $3.35 \cdot 10^{-2}$ | $1.05 \cdot 10^{-2}$ | $2.97 \cdot 10^{-3}$ |

The intermediate cuvette volumes varied so that the combined $V_{meter}+V_{int}=2.0$ μl. This ensured a 1:1 mixture.

Since the second stage structure is the same as the $1^{st}$ stage, and assuming that the solution in the $5^{th}$ dilution/reservoir is fully mixed prior to feeding the $2^{nd}$ stage (i.e. no error propagation), the dilution ratios for the $2^{nd}$ stage are shown in Table II.

TABLE II

2nd Stage characteristics

|  | Non-metered/ 5th Dilution | 6th Dilution | 7th Dilution | 8th Dilution | 9th Dilution |
|---|---|---|---|---|---|
| Theoretical Dilution Ratio | $2.97 \cdot 10^{-3}$ | $9.40 \cdot 10^{-4}$ | $3.18 \cdot 10^{-4}$ | $9.93 \cdot 10^{-5}$ | $3.11 \cdot 10^{-5}$ |

The dimensions of the valving structures used in this disc were as follows:

Valve Dimensions

| Valve Location | Valve Dimensions (Depth × Width, μm) |
|---|---|
| Dilution 1-3 meter valve | 75 × 200 |
| Dilution 4 meter valve | 85 × 200 |
| Dilution 5 meter valve | 71.5 × 154 |
| Dilution 6-8 meter valve | 150 × 150 |
| Dilution 9 meter valve | 150 × 200 |
| Intermediate Cuvette bottom exit | 35 × ~80 |
| Intermediate Cuvette top exit | 45 × ~80 |
| Dilution 5 Intermediate bottom exit | 45 × ~80 |
| Dilution 5 Intermediate top exit | 250 × 400 |
| Diluent Valve - 1st stage | 250 × 200 |
| Diluent Valve - 2nd stage | 35 × ~80 |

The following pattern of disc acceleration (the "spin profile") was used to perform dilution of fluorescein using microfluidics structures as shown in FIG. 17 and the sizes and volumes set forth in Tables I and II: The platform was loaded at platform rest (rpm=0) and then the disc accelerated to 300 rpm. At this speed the fluid comprising the fluorescein solution was motivated from the sample reservoir and into the manifold. Thereafter, disc speed was increased to 535 rpm, at which speed the non-metered intermediate cuvette and the metered chambers were filled. As the speed was increased to 560 rpm the capillary valve at the overflow chamber was overcome and excess fluorescein solution passed into the overflow chamber. Concomitantly, the diluent chamber valve was overcome and the bubble created in the microfluidics motivated to the transverse manifold and entered the bubble capture region. The speed was increased a final time to 900 rpm, and capillary valves controlling all metered chambers were overcome and all intermediate cuvettes filled. Disc speed was then reduced to 600 rpm to prevent intermediate exit valve from breaking prematurely and to permit time for the manifold to drain of excess diluent and fluorescein solution.

$2^{nd}$ Stage

The spin profile for the second stage was commenced manually once the manifold from the first stage completely drained (~15 sec). Disc speed was increased to 1125 rpm to overcome the valve retaining the diluted fluorescein solution from the fifth dilution reservoir; disc speed was controlled to be no greater than 1125 rpm, since higher speeds could result in the capillary valves controlling the first stage intermediate exit valves being overcome. Once the fluid exits the $5^{th}$ dilution reservoir, disc speed was reduced to 500 rpm, at which speed the non-metered volume and the metered chambers were filled. Thereafter, disc speed was again increased to 650 rpm, to overcome the capillary valve at the overflow chamber and to overcome the capillary valve controlling the diluent reservoir for the second stage. The disc speed was then sequentially increased to 775 rpm to overcome the capillary valve controlling the 9th dilution meter, then to 850 rpm to overcome the capillary valve controlling the $7^{th}$ and $8^{th}$ meter valves, then to 900 rpm to overcome the $6^{th}$ dilution meter valve, and finally to 1000 rpm to overcome the capillary valve controlling the capillary valve controlling the overflow chamber. Rotation of the disc at 1000 rpm was continued to drain the remaining fluid in the manifold into the overflow chamber.

Filling the Detection Cuvettes

To empty the intermediate cuvettes and fill the detection cuvettes the disc speed (rpm) were increased from 1000 rpm to 2500 rpm at 500 rpm/s The results of these experiments are shown in Table III. These results are a combination of 3 discs for each of first, the $1^{st}$ stage results and second the results for the $4^{th}$ dilution to the $9^{th}$. The results are presented in terms of normalized fluorescein concentration, therefore the first non-metered detection cuvette will have a concentration, $C_1$, of unity, while the additional detection cuvettes should theoretically follow $C_i=DR_i* C_1$, where, i refers to the $i^{th}$ dilution.

As seen in Table III, the experimental results are very similar to the theoretical predictions, therefore signifying that the disc is working according to the design.

TABLE III

Summary of fluorescein dilution experiments on 5-log dilution disc

| Detection Cuvette | Theoretical Concentration | Experimental Concentration |
|---|---|---|
| 1 | $1.00 \cdot 10^{-0}$ | $1.00 \cdot 10^{-0}$ |
| 2 | $3.17 \cdot 10^{-1}$ | $2.72 \cdot 10^{-1}$ |
| 3 | $1.07 \cdot 10^{-1}$ | $0.88 \cdot 10^{-1}$ |
| 4 | $3.35 \cdot 10^{-2}$ | $2.71 \cdot 10^{-2}$ |
| 5 | $1.05 \cdot 10^{-2}$ | $0.95 \cdot 10^{-2}$ |
| 6 | $2.97 \cdot 10^{-3}$ | $2.68 \cdot 10^{-3}$ |
| 7 | $9.40 \cdot 10^{-4}$ | N.D.* |
| 8 | $3.18 \cdot 10^{-4}$ | $3.09 \cdot 10^{-4}$ |
| 9 | $9.93 \cdot 10^{-5}$ | $10.8 \cdot 10^{-5}$ |
| 10 | $3.11 \cdot 10^{-5}$ | $4.11 \cdot 10^{-5}$ |

*N.D. = Not determined

These results are also depicted graphically in FIGS. 35A and 35B.

The experimental fluorescein concentration from the dilution disc was determined using results from an experimentally determined calibration curve of concentration vs. fluorescence signal. There is a slight curvature to the calibration curve for fluorescein concentrations above ~5 μM, and the curve is essentially linear below this concentration. Therefore the concentrations in the $2^{nd}$ stage were determined using a linear relationship. No background subtraction was performed.

Based on the experimental dilution factors shown in Table I, a well-characterized CYP assay (CYP3A4/DBF/Ketoconazole, as described in Kobayashi et al., 2003, *Drug Metab Dispos*. 31:833-6; Margolis & Obach, 2003, *Drug Metab Dispos*. 31:606-11; Shou et al;., 1994, *Biochemistry* 33: 6450-5; Remmel & Burchell, 1993, *Biochem Pharmacol* 46:559-66) was next performed to assess the performance of the dilution disc. The results, from a combination of data obtained from three independently produced and tested microsystems platforms demonstrated the expected degree of dilution of the assay components on the disc.

It should be understood that the foregoing disclosure emphasizes certain specific embodiments of the invention and that all modifications or alternatives equivalent thereto are within the spirit and scope of the invention.

What is claimed is:

1. A centripetally-motivated microsystems platform comprising:
    a) one or a plurality of sample reservoirs,
    b) an overflow reservoir,
    c) one or a plurality of diluent reservoirs,
    d) one or a plurality of dilution reservoirs,
    e) a metering manifold, wherein the metering manifold is fluidly connected to each of the plurality of dilution reservoirs and the manifold is further fluidly connected to the overflow reservoir, and
    f) a plurality of microchannels embedded in the microsystems platform and in fluidic contact with each of the sample reservoirs, the metering manifold, each of the diluent reservoirs, and each of the dilution reservoirs,
    wherein rotation of the platform motivates flow of a sample from the sample reservoir and a diluent from the diluent reservoir through the metering manifold and into one or a plurality of dilution reservoirs,
    wherein the platform is rotated about an axis of rotation,
    wherein the sample is diluted from a first concentration in the sample reservoir to a lesser, more dilute sample concentration in the one or plurality of dilution reservoirs,
    wherein the microsystems platform further comprises a means for mixing fluidly connected to the metering manifold or the dilution reservoir, wherein sample and diluent are mixed,
    wherein the means for mixing comprises one or a plurality of side microchannels running substantially parallel to a main microchannel that is fluidly connected to the one or a plurality of dilution reservoirs and to the metering manifold, wherein the side microchannels are fluidic contact with the main microchannel, each side microchannel having first and second openings to the main microchannel,
    wherein the second opening is at a position in a main microchannel wall distal from the center of the axis of rotation compared with the first opening,
    wherein fluid movement in the main microchannel at each of the first openings of the side microchannels splits fluid flow into each of the side microchannels, and continued fluid flow recombines the fluid from each of the side microchannels into the main microchannel at the position of the second opening of each of the side microchannels.

2. A microsystems platform rotated about an axis of rotation comprising:
    a) a main microchannel having a length embedded in the microsystems platform and comprising
        i) an inlet channel,
        ii) a center channel, and
        iii) an outlet channel; and wherein the platform further comprises
    b) a mixing unit, comprising one or a plurality of side microchannels positioned substantially parallel to the main microchannel,
        wherein each of the side microchannels are in fluidic contact with the main microchannel, each side microchannel being in fluidic contact with the main microchannel by first and second openings in the main microchannel,
        wherein the second opening is at a position in a main microchannel wall distal from the center of the axis of rotation compared with the first opening,
        wherein fluid movement in the main microchannel at each of the first openings of the side microchannels splits fluid flow into each of side micro channels, and continued fluid flow recombines the fluid from each of the side microchannels into the main microchannel at the position of the second opening of each of the side microchannels.

3. The microsystem platform of claim 2 wherein the main microchannel further comprises a sample input port.

4. The microsystem platform of claim 2 wherein the main microchannel further comprises a sample output port.

5. The microsystem platform of claim 2 comprising multiple mixing units fluidly connected in series.

6. The microsystem platform of claim 2 wherein two or a plurality of the side microchannels are the same length.

7. The microsystem platform of claim 2 wherein at least one side microchannel is longer than the other side microchannels.

8. The micro system platform of claim 7, wherein the other side microchannel is longer than the center channel.

9. The microsystem platform of claim 2 wherein all of the side microchannels are the same length as the center channel.

10. The microsystem platform of claim 2 wherein the side microchannels are longer than the center channel.

11. The microsystem platform of claim 2 wherein the side microchannels have the same channel width and depth as the main microchannel.

12. The microsystem platform of claim 11 wherein the channel width and depth is 200 .mu.m.

13. The micro system platform of claim 2 wherein at least one of the side microchannels has a smaller cross sectional area than the center channel.

14. The microsystem platform of claim 2 wherein at least one of the side microchannels have a larger cross sectional area than the center channel.

15. The microsystem platform of claim 2, wherein the microsystem platform is constructed of an organic material, an inorganic material, a crystalline material, or an amorphous material.

16. The microsystem platform of claim 15, wherein the microsystem platform further comprises silicon, silica, quartz, a ceramic, a metal or a plastic.

* * * * *